US009012497B2

(12) United States Patent
Meyer et al.

(10) Patent No.: US 9,012,497 B2
(45) Date of Patent: Apr. 21, 2015

(54) CYCLOHEXYL CARBAMATE COMPOUNDS AS ACTIVE ANTI-CELLULITE INGREDIENTS

(75) Inventors: Imke Meyer, Bodenwerder (DE); Heiko Oertling, Lausanne (CH); Nadine Hillebrand, Steinheim (DE); Claudia Gömann, Golmbach-Warbsen (DE); Rahim Brodhage, Höxter (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/699,487

(22) PCT Filed: May 25, 2010

(86) PCT No.: PCT/EP2010/057112

§ 371 (c)(1), (2), (4) Date: Feb. 5, 2013

(87) PCT Pub. No.: WO2010/097479

PCT Pub. Date: Sep. 2, 2010

(65) Prior Publication Data

US 2013/0137710 A1 May 30, 2013

(51) Int. Cl.

| | |
|---|---|
| ***A61K 8/44*** | (2006.01) |
| ***A61K 31/00*** | (2006.01) |
| ***A61Q 19/06*** | (2006.01) |
| ***A61K 31/27*** | (2006.01) |

(52) U.S. Cl.

CPC . *A61K 8/44* (2013.01); *A61K 31/00* (2013.01); *A61Q 19/06* (2013.01); *A61K 31/27* (2013.01)

(58) Field of Classification Search

CPC ......... A61K 31/00; A61K 31/27; A61K 8/44; A61Q 19/06

USPC ............ 514/479, 484, 490; 560/115, 162, 29, 560/32

See application file for complete search history.

(56) References Cited

U.S. PATENT DOCUMENTS

| | | | | |
|---|---|---|---|---|
| 5,892,100 | A * | 4/1999 | Yamanaka et al. | 560/157 |
| 2003/0050318 | A1 | 3/2003 | Shirley | |
| 2003/0119900 | A1 | 6/2003 | Kroetz et al. | |
| 2003/0134885 | A1 | 7/2003 | Bernardon et al. | |
| 2008/0255178 | A1 | 10/2008 | Schrimpf et al. | |
| 2009/0214680 | A1 * | 8/2009 | Giuliano et al. | 424/728 |
| 2010/0034657 | A1 | 2/2010 | Hunt et al. | |

FOREIGN PATENT DOCUMENTS

| | | | |
|---|---|---|---|
| DE | 2934355 | A1 | 3/1981 |
| GB | 1058381 | A * | 2/1967 |
| JP | 6-199740 | | 6/1986 |
| JP | 2003-535915 | A | 12/2003 |
| JP | 2004501950 | A | 1/2004 |
| JP | 2004346060 | A | 12/2004 |
| JP | 2006511484 | A | 4/2006 |
| JP | 2006523244 | A | 10/2006 |

(Continued)

OTHER PUBLICATIONS

Barrett et al. "A structural screening approach to ketoamide-based inhibitors of cathepsin K" Bioorganic & Medicinal Chemistry Letters, 2005, vol. 15, pp. 2209-2213.*

Radwan et al. "Potential of some monoterpenoids and their new N-methyl carbamate derivatives against snail vector, *Biomphalaria alexandrina*" Ecotoxicology and Environmental Safety, 2008, vol. 71, pp. 889-894.*

Szekacs et al. "Optimization and validation of an enzyme immunoassay for the insect growth regulator fenoxycarb" Analytica Chemica Acta, 2003, vol. 487, pp. 15-29.*

(Continued)

*Primary Examiner* — Kendra D Carter

(74) *Attorney, Agent, or Firm* — Novak Druce Connolly Bove + Quigg LLP

(57) ABSTRACT

The present invention relates to the cosmetic, dermatological or therapeutic use of certain cyclohexyl carbamate compounds of formula (I) given below, preferably as anti-cellulite actives. The invention further relates to compositions and cosmetic, dermatological or therapeutic products comprising such compounds of formula (I), which are preferably suitable for the prophylaxis (prevention) and cosmetic treatment (combating) of cellulite in human beings, corresponding methods and novel compounds of formula (I)

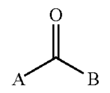

(I)

wherein A denotes

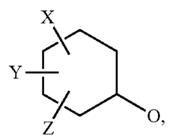

wherein X, Y and Z independently of one another denote hydrogen, C1-C4-alkyl or C2-C4-alkenyl, wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms, B denotes $NR^1R^2$, wherein $R^1$ denotes hydrogen or an organic radical having 1 to 14 carbon atoms, $R^2$ denotes an organic radical having 1 to 14 carbon atoms, and wherein optionally $R^1$ and $R^2$ are covalently bonded to one another, preferably so that B is a 3 to 8 membered ring.

22 Claims, No Drawings

(56) References Cited

FOREIGN PATENT DOCUMENTS

| | | | |
|---|---|---|---|
| JP | 2007503392 A | | 2/2007 |
| JP | 2008120729 A | | 5/2008 |
| JP | 2009144179 A | | 7/2009 |
| JP | 2013511543 A | | 4/2013 |
| JP | 2013511544 A | | 4/2013 |
| WO | WO-9721678 A1 | | 6/1997 |
| WO | WO-02/02071 A2 | | 1/2002 |
| WO | WO 2004033422 A2 | * | 4/2004 |
| WO | WO-2009144179 A1 | | 12/2009 |

OTHER PUBLICATIONS

International search report with references cited and written opinion under Rule 43 PCT attached to the search report, International Application No. PCT/EP2010/057112, filed May 25, 2010.

Notification of the First Office Action with English translation, issued in parallel Chinese Application No. 201080068221.2 on Dec. 24, 2013.

Office Action from the European Patent Office issued in parallel European Application No. 10 721 157.5, dated Jul. 18, 2014.

Office Action from the Chinese Patent Office issued in Chinese Patent Application No. 201080068221.2, dated Aug. 7, 2014, along with English translation of Office Action.

* cited by examiner

CYCLOHEXYL CARBAMATE COMPOUNDS AS ACTIVE ANTI-CELLULITE INGREDIENTS

CROSS-REFERENCE TO RELATED APPLICATIONS

This application is a national stage application (under 35 U.S.C. §371) of PCT/EP2010/057112, filed May 25, 2010, which is incorporated herein by reference in its entirety.

The present invention relates to the cosmetic, dermatological or therapeutic use of certain cyclohexyl carbamate compounds of formula (I) given below, preferably as anti-cellulite actives. The invention further relates to compositions and cosmetic, dermatological or therapeutic products comprising such compounds of formula (I), which are preferably suitable for the prophylaxis (prevention) and cosmetic treatment (combating) of cellulite in human beings, corresponding methods and novel compounds of formula (I).

Cellulite is also known under the synonyms protrusio cutis and colloquially as orange peel skin. It is a cosmetic-aesthetic problem which is accompanied by the formation of dimples and indentations of the skin and nodule formation of the subcutaneous fat tissue. Cellulite can occur on any part of the human body, but the outer side and the back of the thighs as well as the buttocks are most frequently affected. Breasts, lower stomach, upper arms or neck are also sometimes affected by cellulite.

Cellulite may be regularly found on parts of the human body with excessive fat deposits, but overweight is not a prerequisite for its occurrence. Slim women increasingly also have pronounced cellulite symptoms. However, there is probably a correlation between the severity of the cellulite and the percentage of fat in the tissue.

The gender-specific anatomic structure of the skin of human beings (humans) has a great influence on the development of cellulite. Thus, for example, cellulite can only seldom be observed in men, while, on the other hand, about 80%-90% of all women are affected, in particular Caucasian women. The structure of the dermis, in particular, has an effect on the skin relief. Thus, the fat chambers in men, when the skin is pressed together, are held back by intersecting connective tissue septa and the clamp-like enclosure of the fat cells connected therewith. On the other hand, in women, the fat chambers separated from one another in a tubular manner, which are enclosed by actinomorphically extending connective tissue septa, bulge up when being pressed together.

In addition, the visible pattern of the cellulite is based on an increase in fat cushions in the subcutis and a reduction in the circulation conditions in the blood and lymph vessels. The cause is therefore partly a predisposed weakening of the connective tissue with simultaneous occurrence of enlarged fat cell chambers with stress, sports activity, smoking, pregnancies and female hormones (oestrogen and progesterone) playing a part, in addition to genetic factors.

Cellulitis is to be clearly separated and distinguished from the cosmetic phenomenon of cellulite. Cellulitis is a bacterial infection of the subcutaneous tissue, which in many cases may be a serious illness, and in contrast to cellulite, has to be treated therapeutically.

As mentioned above, even healthy women are affected by cellulite. It should be stressed that cellulite itself is not an illness and thus its treatment is not to be regarded as therapy. Light or moderate cellulite, which is considered as healthy skin, is not a condition or blemish that requires medication and is not regarded as a pathological state. In contrast thereto, heavy cellulite may be accompanied by side or after effects like pain or other medical symptoms. Medical specialists can clearly distinguish between light or moderate cellulite and heavy cellulite and medical specialists also decide whether a treatment of cellulite in the medical sense is advisable or needed.

In the context of the present invention, a cosmetic use or a cosmetic method is free of any therapeutic (side) effects.

In the context of the present invention, a therapeutic or pharmaceutical use or method is considered as medical treatment, optionally with cosmetic (side) effects.

The conventional treatment methods for cellulite attempt to encourage the blood circulation of the relevant skin parts and to positively influence the connective tissue structure, for example by massage, lymph drainage, diet, sport, magnetic fields or else liposuction (removing fat by suction).

In the literature, the use of several cosmetic products is described for the prophylaxis and treatment of cellulite. But their effectiveness is often very limited because of the very complex mechanism of fat cell metabolism. It is not sufficient to focus on one mechanism involved in the storage of lipids in adipose tissue.

Fat metabolism in the fat tissue of humans, in order to reduce the stored lipid quantity, can in principle be regulated by three Routes:

Route (i): Inhibition of the Differentiation of Preadipocytes

The differentiation of the precursor cells of the fat cells called preadipocytes to the real fat cells, called adipocytes, which may store triglycerides, can be inhibited. Expressed more simply, an inhibition of Route (i) prevents the build up of cellulite in that the number of fat cells does not increase. This process of differentiation from preadipocytes to adipocytes is called adipogenesis.

Route (ii): Inhibition of the Lipogenesis in Adipocytes

The storage of triglycerides in the adipocytes (also called lipogenesis) can be prevented or inhibited. Expressed more simply, an inhibition of Route (ii) prevents the storage of further triglycerides (fats) in the cell and existing fat cells do not store any new fat. Owing to the natural fat metabolism, when Route (ii) is inhibited, the fat content in the cell decreases.

Route (iii): Stimulation of Lipoylsis in Adipocytes

An augmented/increased hydrolysis of lipids already stored in the adipocytes—also called lipolysis—is possible by targeted stimulation. Expressed more simply, stimulation of Route (iii) increases the breakdown of the fats already present in the cell while an inhibiting, i.e. antagonistic effect with respect to Route (iii) on the other hand inhibits or prevents the breakdown of fat.

The differentiation of cells is the changing of the control of the gene activity of a cell so that various protein stores are provided in the cells by means of transcription and protein biosynthesis and the cells differ according to appearance and function. Thus, adipocytes only express enzymes, which are necessary for the storing of fats, after differentiation. In their precursor cells, the undifferentiated preadipocytes, these enzymes are not expressed or only to a very small extent.

Cosmetic preparations which have the prophylaxis and treatment of cellulite as a goal have already been proposed in the literature. They mostly influence adipose tissue or adipocytes by a specific activity.

EP 1 234 572 describes a cosmetic preparation of at least one isoflavone aglycone, in particular genistein and/or daidzein, for treating cellulite. The isoflavone aglycone is in this case combined with an algae extract. Genistein is described there as an active ingredient, which inhibits the multiplication of precursor fat cells and in addition the enzyme phosphodiesterase.

A cosmetic preparation of certain biochinones and isoflavonoids, preferably genistein, are described for the prophylaxis of cellulite in DE 10 2004 032 837. It is maintained that the effect of this preparation takes place by means of an improvement in the cell metabolism. It cannot be seen there which mechanism of the cell metabolism is improved. It can also not be inferred there whether the fat tissue is influenced by the cosmetic preparation.

Preparations containing certain isoflavones are also described in DE 100 09 423, the isoflavones being described as materials with an anti-oestrogen effect and used because of this effect. Daidzein, genistein, glycitein, formononetin and others are preferred isoflavones there.

WO 2006/063714 teaches compositions for topical administration, containing a PDE3 inhibitor as active ingredient, for use in the treatment of cellulite and proposes pharmaceutical compositions comprising drugs like anagrelide, cilostazol, pimobendan, milrinone, aminone, olprinone, enoximone, cilostamide, vesnarinone and trequinsin.

The effectiveness of the substances proposed in the prior art so far is often very limited.

Cellulite and adipocyte metabolism is a very complex mechanism which needs the alteration of different pathways within the fat metabolism to be effective. Influencing only one of the different pathways is generally not effective in humans because in parallel other pathways are influenced which in their turn lead to an increase of stored lipid quantity, leading to an adverse effect.

It was therefore the object of the invention to disclose active ingredients and corresponding preparations which show a, preferably improved, activity with respect to the prophylaxis and treatment of cellulite.

It has surprisingly been found that this object can be achieved by using compounds of formula (I) or a cosmetically acceptable salt of a compound of formula (I) or a mixture containing two or more of these compounds or the salts thereof (i) for the cosmetic prevention, treatment or reduction of cellulite, and/or (ii) for the cosmetic (non-therapeutic)

reduction of the lipid quantity contained in subcutaneous fat tissue, and/or stimulation of lipoylsis in adipocytes, and/or inhibition of the differentiation of preadipocytes, and/or inhibition of the lipogenesis in adipocytes, and/or (iii) as cosmetic anti-cellulite active, (I)

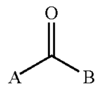

wherein

A denotes

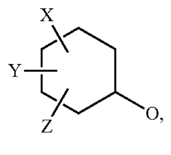

wherein X, Y and Z independently of one another denote hydrogen, C1-C4-alkyl or C2-C4-alkenyl, wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms, B denotes $NR^1R^2$, wherein $R^1$ denotes hydrogen or an organic radical having 1 to 14 carbon atoms, $R^2$ denotes an organic radical having 1 to 14 carbon atoms, and wherein optionally $R^1$ and $R^2$ are covalently bonded to one another, preferably so that B is a 3 to 8 membered ring.

The compounds of formula (I) thus are cyclohexyl carbamates (Carb-I)

(Carb-I)

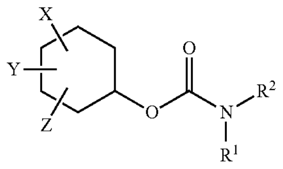

wherein $R^1$, $R^2$ and X, Y and Z have the meaning indicated hereinbefore or hereinafter.

As common in the art, in the context of the present invention, the substituents X, Y, and Z can in each case occupy—as indicated in the different structural formulae—any position in the cyclohexyl ring, i.e. in ipso, ortho, meta or para position to the cyclohexyl-carbon atom bonded to the oxygen of group A.

It is thus evident that two of the substituents X, Y, and Z—with exception of the ipsoposition—can be bonded to the same carbon atom of the cyclohexyl ring of group A.

The compounds of formula (I) show a pronounced effect in the treatment of cellulite, recognisably by means of echographic determination of the subcutis layer thickness, in particular to prevent the increased formation of fat stores in the skin and/or cellulite, in that the lipid content in the human subcutaneous fat tissue is reduced. The invention therefore relates to cosmetic preparations (compositions) containing a corresponding effective quantity of one or more compounds of formula (I), in particular for the topical treatment and prevention of increased formation of fat stores in the skin and/or cellulite.

The compounds of formula (I) structurally belong to the group of cyclohexyl carbamates. Some of these compounds have been described in the prior art.

As common in the art, in the context of the present invention, abbreviations for certain chemical groups are used, for example Me=methyl, Et=ethyl, Pr=propyl, Bu=butyl, Ph=phenyl.

For the sake of clarity, it is emphasized that the present invention does not relate to substances as such or mixtures of substances as such which have been described or disclosed in the prior art.

The following compounds of formula (I) and more specifically of formula (Carb-II-R1H) as defined below have been described in the literature.

WO 2007/16441, WO 2008/051514 and WO 2008/051475 mention

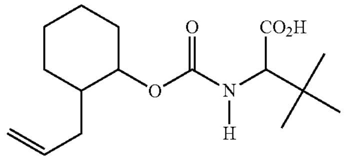

-continued

WO 2008/051514 discloses

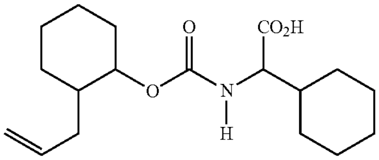

Bioorganic & Medicinal Chemistry Letters (2005), 15(9), 2209-2213 describes

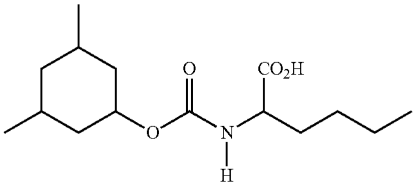

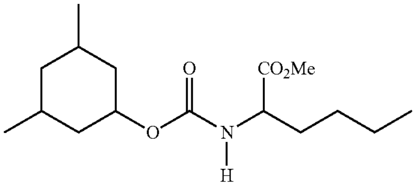

Organic Preparations and Procedures International (2004), 36(2), 141-149 discloses

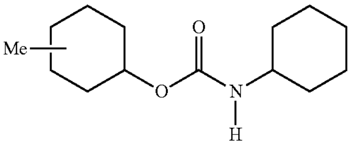

, i.e.

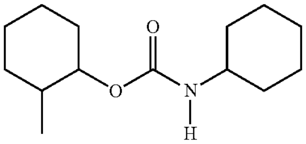

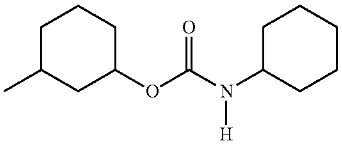

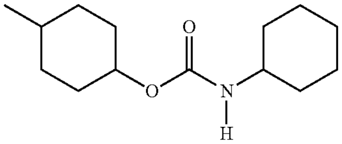

U.S. Pat. No. 5,892,100 mentions

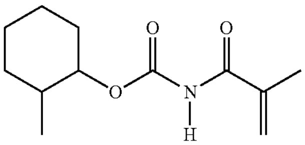

JP06-072036-A discloses

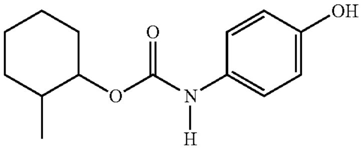

-continued

JP04-029964-A describes

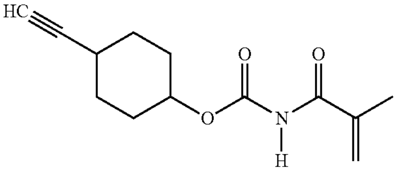

U.S. Pat. No. 5,260,474 mentions

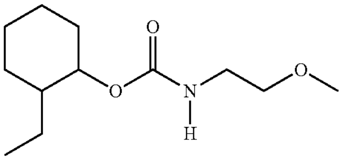

Doklady - Akademiya Nauk Azerbaidzhanskoi SSR (1980), 36(2), 63-66 describes

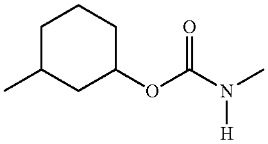

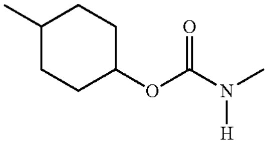

FR 2 259 589 mentions

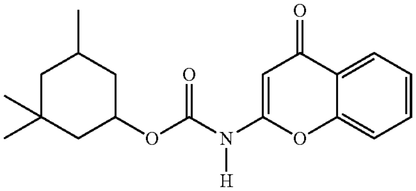

DE 20 500 87 discloses

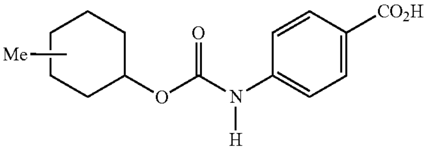

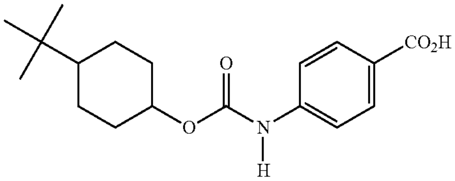

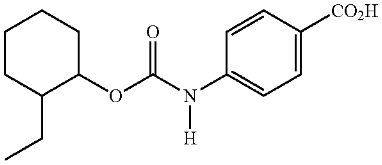

Journal of Agricultural and Food Chemistry (1967), 15(6), 1022-1029 describes

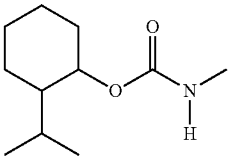

-continued

Izvestiya Akademii Nauk SSSR, Seriya Khimicheskaya (1966), (5), 922-924 discloses

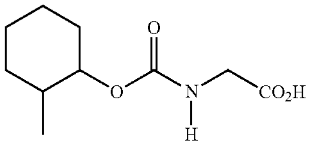

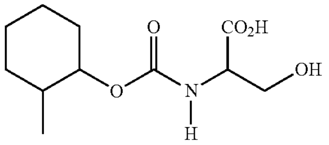

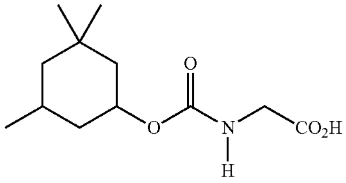

FR 1 401 219 mentions

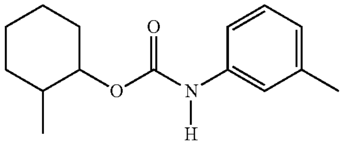

Collection of Czechoslovak Chemical Communications (1965), 30(2), 585-598 and 599-604 describe

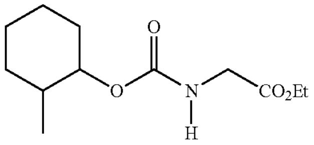

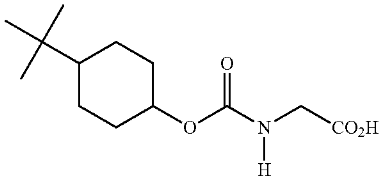

Annales Pharmaceutiques Francaises (1958), 16, 408-13 and Journal of Organic Chemistry (1958), 23, 1590-1591 disclose

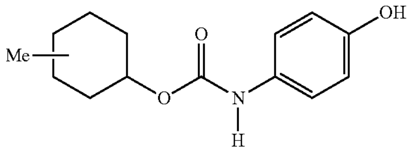

Annales Pharmaceutiques Francaises (1958), 16, 408-13 mentions

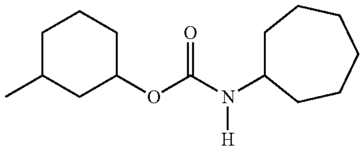

Azarbaycan Neft Tasarrufati (1933), (No. 3), 66-75 discloses

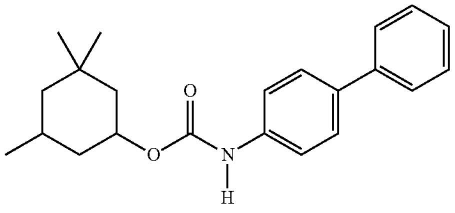

-continued

Synthetic Communications 2001, 31(24), 3759-3773 discloses

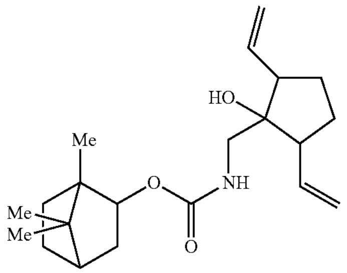

Journal of Medicinal Chemistry 1983, 26(9), 1215-18 discloses

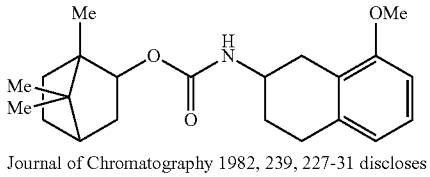

Journal of Chromatography 1982, 239, 227-31 discloses

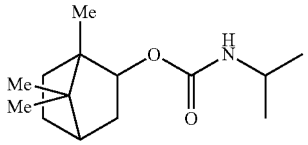

Ecotoxicology and Environmental Safety 2008, 71(3), 889-894 discloses

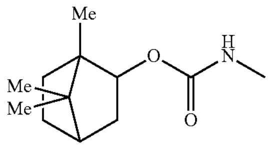

Chirality 2010, 22(2), 267-274 discloses

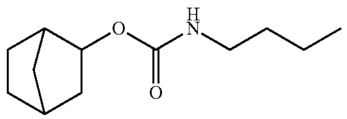

Synthesis 1989, (2), 131-132 discloses

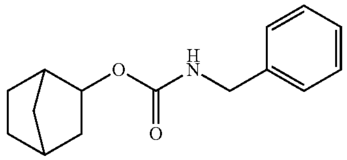

Various menthyl-carbamates of formula (M-H) have been described in the prior art

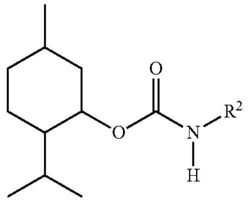

(M-H)

wherein $R^2$ has the respective meaning indicated hereinbefore or hereinafter as defined for formula (I) and more specifically as defined for (Carb-II-R1H) given below.

Also, several compounds of formulae (I), (Carb-II) and (Carb-II-R1H) in which X, Y, and Z each denote H have been disclosed in the prior art.

Further, several compounds of formulae (I), (Carb-II) and more specifically of formula (Carb-II-R1H) as defined below wherein $R^2$ denotes phenyl or naphthyl have been described in the prior art.

Additionally, some bicyclic carbamates of formulae (Carb-II) and (Carb-II-R1H) as defined below wherein two of the radicals X, Y and Z are covalently bonded to one another under formation of a bicyclic ring system in which $R^2$ contains a —COOH and/or a =CH2 group have been described in the prior art.

WO 2004/033422 relates to compounds inhibiting fatty acid amide hydrolase (FAAH). Methods are described therein to control appetite and treat appetite disorders by administering FAAH inhibitors, thereby reducing body fat or body weight. WO 2004/033422 discloses a very broad generic chemical formula of carbamates which also embraces a vast number of substituted or unsubstituted cyloalkyl carbamates. The only specific compounds disclosed in WO 2004/033422 of relevance in the context of the present invention are the following:

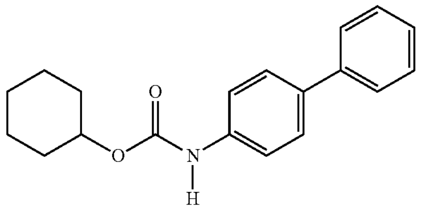

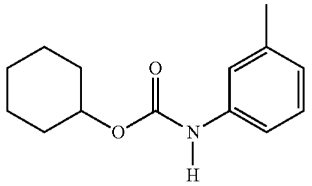

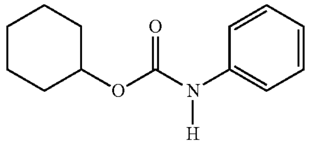

International Journal of Obesity (22 Dec. 2009) doi: 10.1038/ijo.2009.262 investigated the effect of FAAH deficiency in mice on the energy storage and the appetite. It was shown that appetite and food intake did not change with FAAH deficiency. The authors also measured an enhanced body weight, fat content and insulin resistance in FAAH deficient mice compared to wildtype mice at the same caloric intake. An increased lipogenesis in FAAH deficient mice is given therein as reason for this observation.

WO 2004/033422 does not relate to combating or preventing cellulite. There is not link between FAAH inhibition and the reduction of appetite described in WO 2004/033422 and the prophylaxis and cosmetic treatment of cellulite in human beings.

EP 1 284 145 describes the use of N-2-(3,4-dihydroxyphenyl)ethyl-substituted carbonic acid derivatives as radical scavengers and antioxidants. EP 1 284 145 further describes cosmetic preparations containing said carbonic acid derivatives. The effect of these compounds on the metabolism of fat cells or the body weight of humans was not investigated there. The only explicitly mentioned compound in EP 1 284 145 of relevance in view of formula (I) of the present invention is N-[2-(3,4-dihydroxyphenyl)ethyl-O-(1R,3R,4S)-menthyl] carbamate. According to EP 1 284 145, preparations for nutrition or pleasure may additionally comprise bitter substances, such as caffeine.

In a preferred embodiment, a cosmetic or pharmaceutical preparation according to the present invention is free of N-[2-(3,4-dihydroxyphenyl)ethyl-O-(1R,3R,4S)-menthyl]carbamate. In another preferred embodiment, compounds of formula (I) according to the present invention, more specifically compounds of formula (Carb-II-R1H), are excluded in which $R^2$ denotes a 2-(3,4-dihydroxyphenyl)ethyl-radical. In another preferred embodiment, compounds of formula (I) according to the present invention, more specifically compounds of formula (Carb-II-R1H), are excluded in which $R^2$ denotes a radical containing a 3,4-dihydroxyphenyl-group. In another preferred embodiment, cosmetic or pharmaceutical preparations according to the present invention are free of compounds of formula (I) according to the present invention, more specifically of compounds of formula (Carb-II-R1H), in which $R^2$ denotes a 2-(3,4-dihydroxyphenyl)ethyl-radical. In another preferred embodiment, cosmetic or pharmaceutical preparations according to the present invention are free of compounds of formula (I) according to the present invention, more preferably of compounds of formula (Carb-II-R1H), in which $R^2$ denotes a radical containing a 3,4-dihydroxyphenyl-group.

There is no indication hitherto that the compounds used in accordance with the present invention are suitable for the prophylaxis and (preferably cosmetic) treatment of cellulite in humans.

Compounds of formula (I) and preparations (compositions) according to the invention, comprising one or more compounds of formula (I) influence cellulite with regard to the stored lipid quantity, in that the lipid content in humans is reduced.

Thus, in accordance with the present invention, cellulite is prevented, treated or reduced by a preparation (composition) containing one or more compounds of formula (I) by influencing the above described Routes (i) and/or (ii) and/or (iii), most preferably by influencing the above described Routes (i) and (ii) and (iii).

The (preferred) compounds of formula (I) stimulate lipolysis (Route (iii)).

Preferred compounds of formula (I) according to the present invention influence at least two, preferably all three above mentioned Routes (i), (ii) and (iii).

Thus, preferred anti-cellulite active compounds of formula (I) stimulate lipolysis (Route (iii)) and additionally exhibit activity in Route (i) and/or (ii).

To determine whether a compound exhibits an activity in the sense of the present invention corresponding to Routes (i) and/or (ii) and/or (iii), preferably tests are performed in accordance with Examples 2, 3.2, and 4.1 given below:

Route (i): inhibition of adipogenesis (differentiation of preadipocytes) is preferably tested by using the assay as described in Example 2, below.

Route (ii): inhibition of the lipogenesis in adipocytes is preferably tested by using the assay as described in Example 3.2, below.

Route (iii): stimulation of lipoylsis in adipocytes is preferably tested by using the assay as described in Example 4.1, below. More preferably, additionally stimulation of lipoylsis in adipocytes is tested using the assay as described in Example 4.2, below.

In our investigations it was found that compounds of formula (I) in which X, Y and Z each denote hydrogen were less effective regarding the effects to be achieved in the context of the present invention. Compounds of formula (I) in which X, Y and Z each denote hydrogen inhibit adipogenesis (Route (i)) and stimulate lipolysis (Route (iii)) but are no or very weak inhibitors of lipogenesis (Route (ii)). Thus, compounds of formula (I) wherein one, two or all substituents X, Y and Z are not hydrogen, are preferred.

One regulation mechanism of preadipocytes and adipocytes is inter alia the expression of SIRT1 (sirtuin 1), a $NAD^+$ (nicotinamide adenin dinucleotide)-dependent histone deacetylase which regulates senescence and metabolism as well as modulates life span. It is generally known (see Picard, F., M. Kurtev, et al. "Sirt1 promotes fat mobilization in white adipocytes by repressing PPAR-gamma", Nature 2004, 429, 771-6) that SIRT1 influences adipocyte metabolism by inhibiting adipogenesis, the above mentioned Route (i), and stimulates lipolysis, the above mentioned Route (iii). Thus, by stimulating SIRT1 expression, Route (i) and Route (iii) are influenced resulting in a prevention and reduction of cellulite.

Surprisingly it was found that the compounds of formula (I) stimulate SIRT1 expression which inter alia influences the above mentioned Route (i) and Route (iii).

Advantageous for anti-cellulite actives is also an inhibition of proliferation. By inhibiting proliferation of preadipocytes the number of precursor cells is reduced and the process of adipogenesis (Route (i)) is indirectly reduced resulting in a lower number of adipocytes. Surprisingly it was found that the compounds of formula (I) inhibit the proliferation of preadipocytes.

The compounds according to the invention of formula (I), depending on the meaning of X, Y, Z, $R^1$ and $R^2$, may exist in different stereoisomeric forms and may be used in the context of the present invention as stereoisomers, enantiomers, diastereomers, syn-/anti-isomers, endo-/exo-isomers, cis-/trans-isomers or epimers.

As common in the art, a "flat" structural formula, i.e. a structural formula which does not convey any stereochemical information, includes and encompasses all stereoisomers of said structural formula.

The compounds of formula (I) can be used in the context of the present invention in the form of the pure cis- or trans-, syn- or anti-diastereomer or in the form of any mixture of diastereomers. The compounds of formula (I) can also be used in the context of the present invention in the form of the pure enantiomers or in the form of any mixture of enantiomers, in the latter case racemates being preferred.

In case $R^1$ does not denote hydrogen, $R^1$ and $R^2$ independently of one another preferably denote an optionally substituted radical selected from the group consisting of alkyl, heteroalkyl, cycloalkyl, cycloalkylalkyl, alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl.

In case $R^1$ does not denote hydrogen, $R^1$ and $R^2$ independently of one another more preferably denote an optionally substituted radical $C_1$-$C_{14}$-alkyl, $C_1$-$C_{14}$-heteroalkyl, $C_3$-$C_{14}$-cycloalkyl, $C_4$-$C_{14}$-cycloalkylalkyl, $C_2$-$C_{14}$-alkenyl, $C_3$-$C_{14}$-cycloalkenyl, $C_4$-$C_{14}$-cycloalkenylalkyl, $C_2$-$C_{14}$-alkynyl, $C_5$-$C_{14}$-cycloalkylalkynyl, $C_3$-$C_{14}$-aryl, $C_2$-$C_{14}$-heteroaryl, $C_4$-$C_{14}$-arylalkyl, $C_8$-$C_{14}$-cycloalkylaryl, $C_8$-$C_{14}$-cycloalkenylaryl, $C_5$-$C_{14}$-cycloalkylheteroaryl, $C_8$-$C_{14}$-heterocycloalkylaryl, $C_8$-$C_{14}$-heterocycloalkenylaryl, $C_8$-$C_{14}$-heterocycloalkenylheteroaryl and $C_3$-$C_{14}$-heteroarylalkyl.

Heteroalkyl, heteroaryl, cycloalkylheteroaryl, heterocycloalkylaryl, heterocycloalkenylaryl, heterocycloalkenylheteroaryl and heteroarylalkyl radicals in the context of the present invention preferably contain at least one heteroatom, optionally up to four heteroatoms, selected independently from the group consisting of O, S and/or N. Preferred are heteroalkyl, heteroaryl, cycloalkylheteroaryl, heterocycloalkylaryl, heterocycloalkenylaryl, heterocycloalkenylheteroaryl and heteroarylalkyl radicals containing one, two or three heteroatoms, selected independently from the group consisting of O, S and/or N.

Preferably, substituents X, Y, and Z in each case occupy any desired position in the cyclohexyl ring in ortho, meta or para position to the cyclohexyl-carbon atom bonded to the oxygen of the carbamate group. Thus, preferably A denotes

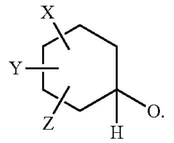

The corresponding preferred compounds of formula (I) are cyclohexyl carbamates of formula (Carb-II):

(Carb-II)

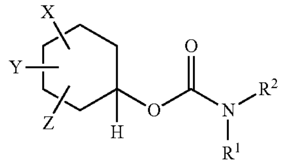

wherein $R^1$, $R^2$ and X, Y and Z have the meaning indicated hereinbefore or hereinafter.

In preferred compounds of formula (I), (Carb-I) and (Carb-II) $R^1$ denotes hydrogen. In our investigations, these compounds were generally found to have a higher activity and efficacy regarding the prophylaxis and treatment of cellulite compared to compounds of formula (I) wherein $R^1$ denoted a radical having 1 to 14 carbon atoms.

Thus, more preferred compounds of formula (I) are cyclohexyl carbamates of formula (Carb-II-R1H):

(Carb-II-R1H)

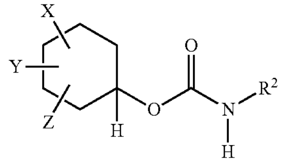

wherein X, Y and Z have the meaning indicated hereinbefore or hereinafter.

Substituents X, Y and Z independently of one another preferably denote hydrogen, methyl, ethyl, n-propyl, isopropyl, n-butyl, sec.-butyl, isobutyl, tert.-butyl, ethenyl, prop-2-en-1-yl, prop-1-en-1-yl, prop-1-en-2-yl, but-1-en-1-yl, but-1-en-2-yl, but-1-en-3-yl, but-2-en-1-yl, but-3-en-1-yl, but-2-en-2-yl, 2-methylprop-1-en-1-yl or 2-methylprop-2-en-1-yl.

In a preferred embodiment, substituents X, Y and Z independently of one another denote hydrogen or C1-C4-alkyl. In another preferred embodiment, at least one of the substituents X, Y and Z denotes C1-C4-alkyl, i.e. at least one of the substituents X, Y and Z does not denote hydrogen.

In another preferred embodiment, two of the substituents X, Y and Z independently of one another denote hydrogen or C1-C4-alkyl and at least one of the substituents X, Y and Z denotes C1-C4-alkyl.

In preferred compounds of formula (I), (Carb-I), (Carb-II) and (Carb-II-R1H), $R^2$ denotes an organic radical having 1 to 12 carbon atoms, preferably an organic radical having 1 to 10 carbon atoms, more preferably an organic radical having 1 to 8 carbon atoms.

In more preferred compounds of formula (I), (Carb-I), (Carb-II) and (Carb-II-R1H), $R^2$ denotes an optionally substituted radical $C_1$-$C_{10}$-alkyl, $C_1$-$C_{10}$-heteroalkyl, $C_3$-$C_{10}$-cycloalkyl, $C_4$-$C_{10}$-cycloalkylalkyl, $C_2$-$C_{10}$-alkenyl, $C_3$-$C_{10}$-cycloalkenyl, $C_4$-$C_{10}$-cycloalkenylalkyl, $C_2$-$C_{10}$-alkynyl, $C_5$-$C_{10}$-cycloalkylalkynyl, $C_3$-$C_{10}$-aryl, $C_2$-$C_{10}$-heteroaryl, $C_4$-$C_{10}$-arylalkyl, $C_8$-$C_{10}$-cycloalkylaryl, $C_8$-$C_{10}$-cycloalkenylaryl, $C_5$-$C_{10}$-cycloalkylheteroaryl, $C_8$-$C_{10}$-heterocycloalkylaryl, $C_8$-$C_{10}$-heterocycloalkenylaryl, $C_8$-$C_{10}$-heterocycloalkenylheteroaryl and $C_3$-$C_{10}$-heteroarylalkyl.

In most preferred compounds of formula (I), (Carb-I), (Carb-II) and (Carb-II-R1H), $R^2$ denotes an optionally substituted radical chosen from the group consisting of $C_1$-$C_8$-alkyl, $C_3$-$C_8$-cycloalkyl, $C_4$-$C_{12}$-cycloalkylalkyl, $C_2$-$C_8$-alkenyl, $C_3$-$C_8$-cycloalkenyl, $C_4$-$C_8$-cycloalkenylalkyl, $C_3$-$C_8$-aryl, $C_2$-$C_8$-heteroaryl, $C_4$-$C_8$-arylalkyl, $C_5$-$C_8$-cycloalkylheteroaryl and $C_4$-$C_8$-heteroarylalkyl.

If the radicals $R^1$ and/or $R^2$ are substituted, $R^1$ and/or $R^2$ each may contain one or more heteroatoms, preferably independently selected from the group consisting of O, S, N, Si and F. If the heteroatoms are selected from the group consisting of O, S and N, the radicals $R^1$ and/or $R^2$ each preferably contain one, two or three heteroatoms selected independently from the group consisting of O, S and/or N.

If the radicals $R^1$ and/or $R^2$ are substituted the following substituents are preferred:

hydroxyl, fluoride, $C_1$-$C_8$-alkyl, preferably methyl, ethyl, n-propyl, iso-propyl, n-butyl, iso-butyl, tert-butyl, $C_3$-$C_{12}$-cycloalkyl, preferably cyclopropyl, cyclopentyl, cyclohexyl, cyclooctyl, cyclododecyl, $C_2$-$C_8$-alkynyl, preferably ethynyl, propynyl, $C_1$-$C_8$-perfluoroalkyl, preferably trifluoromethyl, nonafluorobutyl, $C_1$-$C_8$-alkoxy, preferably methoxy, ethoxy, n-propoxy, iso-propoxy, n-butoxy, iso-butoxy, tert-butoxy, $C_3$-$C_8$-cycloalkoxy, preferably $C_3$-cycloalkoxy, $C_5$-cycloalkoxy, $C_6$-cycloalkoxy, $C_8$-cycloalkoxy, $C_1$-$C_{10}$-alkoxyalkyl, in which 1 to 3 $CH_2$ groups are replaced by oxygen, preferably $—[—O—CH_2—CH_2-]_v$-Q or $—[—O—CH_2—CHMe-]_v$-Q, wherein Q is OH or $CH_3$ and wherein v denotes an integer from 1 to 3, $C_1$-$C_4$-acyl, preferably acetyl, $C_1$-$C_4$-acetal, preferably dimethylacetal, diethylacetal or a methylenedioxy group $—O—CH_2—O—$.

$C_1$-$C_4$-carboxyl, preferably $CO_2Me$, $CO_2Et$, $CO_2$ iso-Pr, $CO_2$tert-Bu, $C_1$-$C_4$-acyloxy, preferably acetyloxy, $Si_1$-$Si_{10}$-silyl, and $Si_1$—$Si_{30}$-siloxy or polysiloxy.

Preferred cosmetically or pharmaceutically acceptable salts of compounds of formula (I) are those in which the one or more counterions (counteracting cation) is selected from the group consisting of $Na^+$, $K^+$, $NH_4^+$, trialkylammonium $NHR^i{}_3{}^+$, $Ca^{2+}$, $Mg^{2+}$, $Zn^{2+}$ and $Al^{3+}$.

In trialkylammonium $NHR^i{}_3{}^+$, preferably each $R^i$ independently of the other radicals $R^i$ denotes an alkyl group having 1 to 30 C-atoms, preferably having 4 to 22 C-atoms.

Particular preferred counterions are $Na^+$, $K^+$, $Ca^{2+}$ and/or $Mg^{2+}$.

In case two different compounds of formula (I) are used as a mixture, generally the ratio by weight of the two compounds is chosen in the range of from 10:1 to 1:10, preferably in the range of from 5:1 to 1:5, more preferably in the range of from 3:1 to 1:3, the counterion, if present, not being included in the case of salts.

In the context of the present invention, a wavy line in structural formulae means that the double bond can be in the (E) or (Z) configuration.

Preferred compounds of formula (I), (Carb-I), (Carb-II) and (Carb-II-R1H) are those in which A denotes a radical chosen from the following list "CyO":

AA

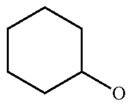

AB

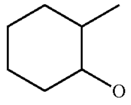

AC

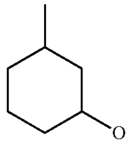

AD

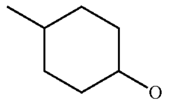

AE

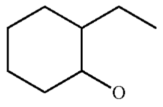

AF

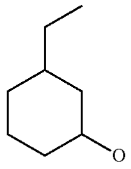

AG

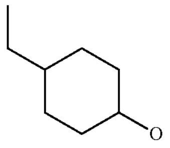

AH

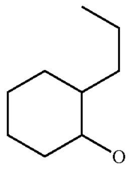

-continued
AI
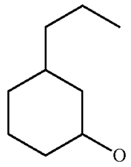
AJ
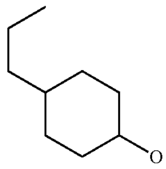
AK
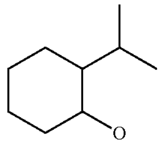
AL
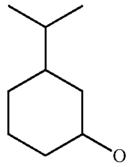
AM
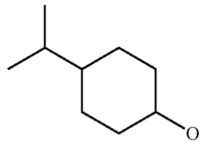
AN
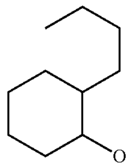
AO
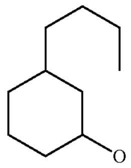
AP
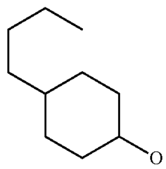
AQ
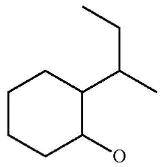
-continued
AR
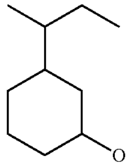
AS
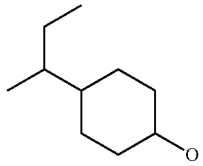
AT
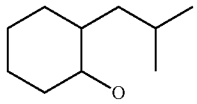
AU
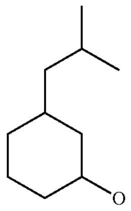
AV
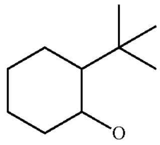
AW
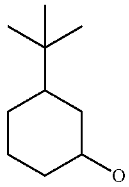
AX
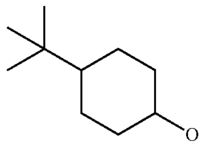
AY
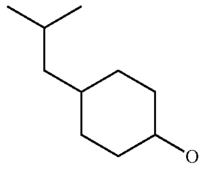
AZ
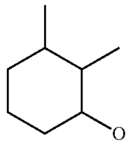

-continued
BA
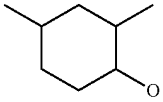
BB
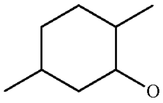
BC
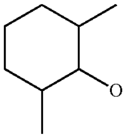
BD
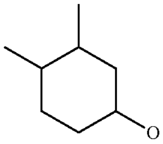
BE
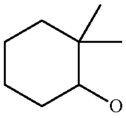
BF
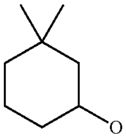
BG
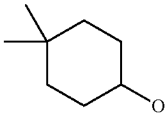
BH
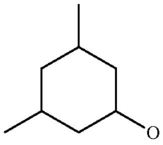
BI
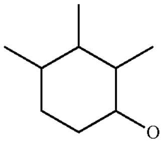
BJ
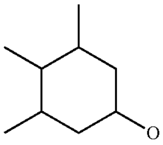
BK
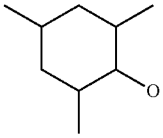
-continued
BL
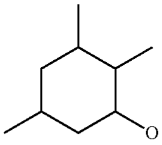
BM
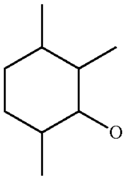
BN
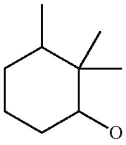
BO
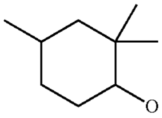
BP
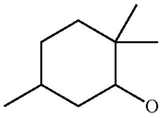
BQ
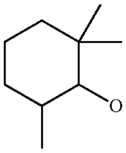
BR
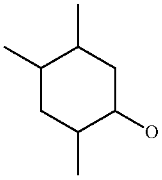
BS
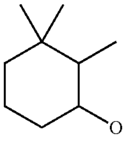
BT
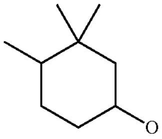
BU
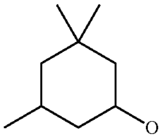

-continued
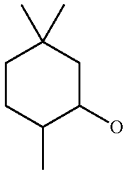
BV
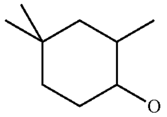
BW
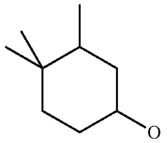
BX
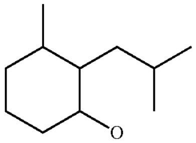
BY
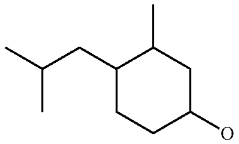
BZ
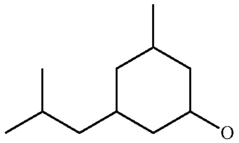
CA
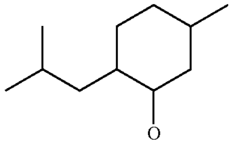
CB
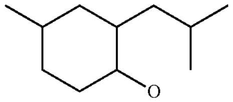
CC
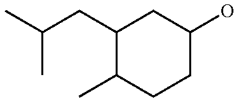
CD
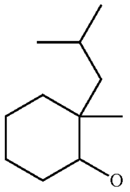
CE
-continued
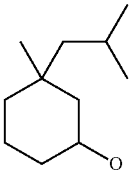
CF
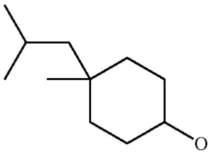
CG
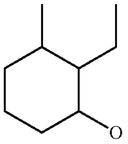
CH
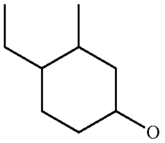
CI
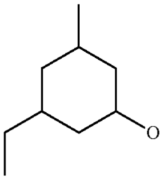
CJ
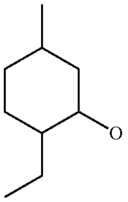
CK
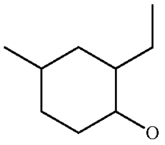
CL
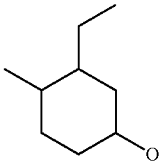
CM
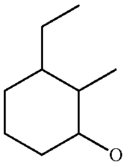
CN -continued
CO
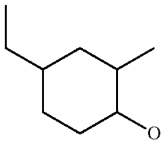
CP
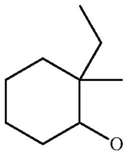
CQ
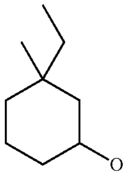
CR
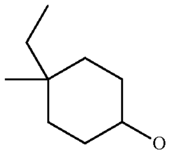
CS
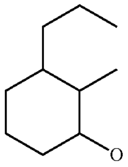
CT
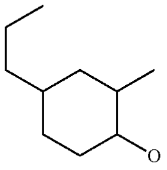
CU
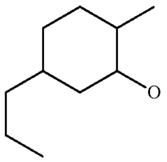
CV
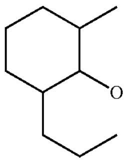
CW
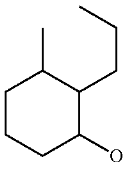
-continued
CX
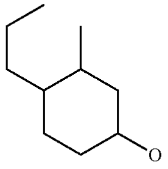
CY
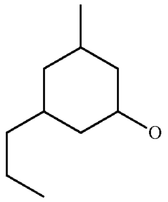
CZ
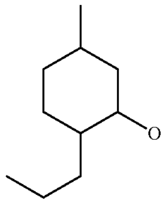
DA
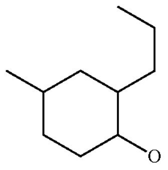
DB
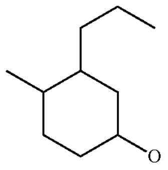
DC
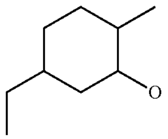
DD
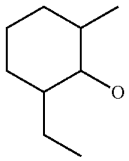
DE
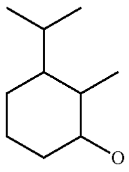
DF
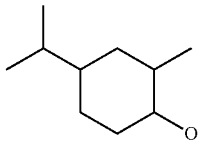

-continued
DG
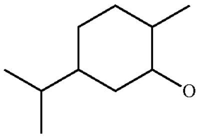
DH
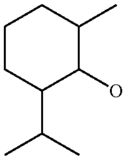
DI
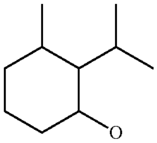
DJ
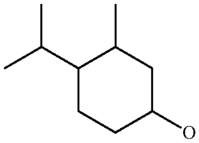
DK
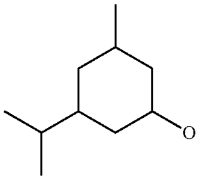
DL
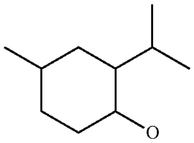
DM
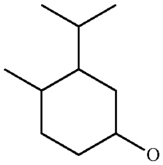
DN
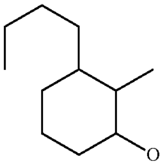
DO
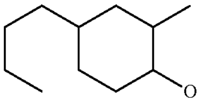
DP
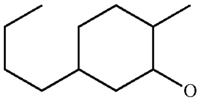
-continued
DQ
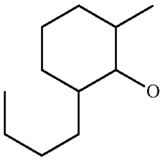
DR
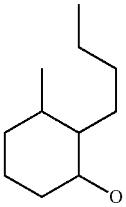
DS
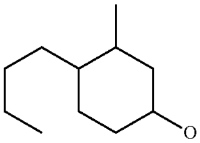
DT
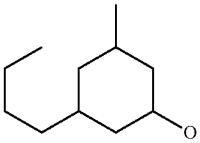
DU
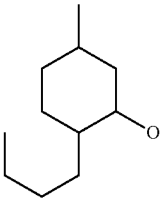
DV
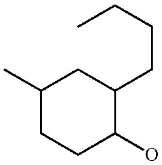
DW
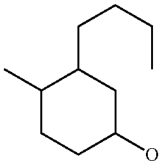
DX
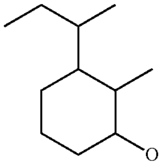
DY
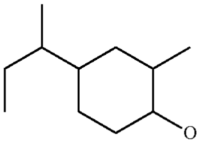

-continued
DZ
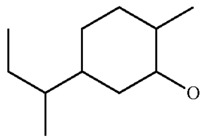
EA
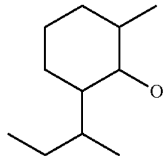
EB
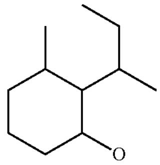
EC
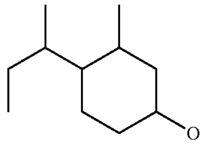
ED
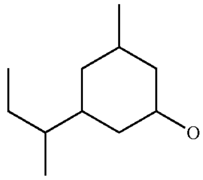
EE
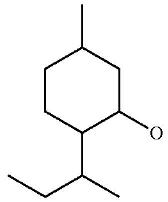
EF
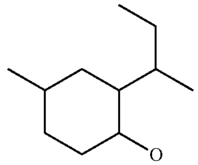
EG
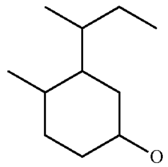
EH
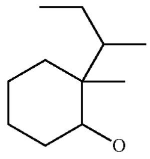
-continued
EI
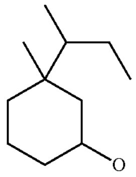
EJ
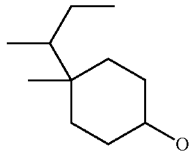
EK
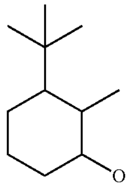
EL
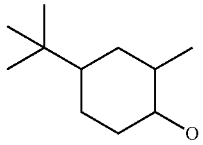
EM
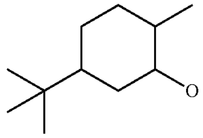
EN
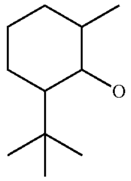
EO
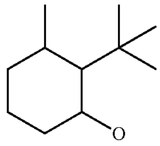
EP
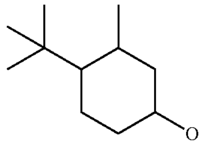
EQ
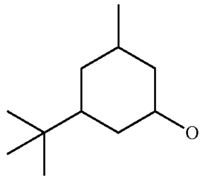

-continued
ER
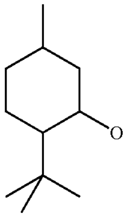
ES
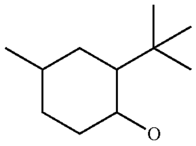
ET
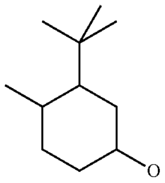
EU
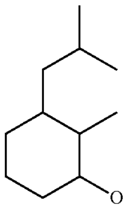
EV
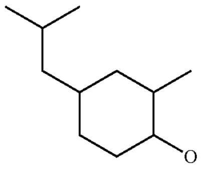
EW
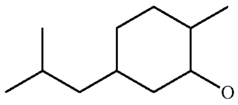
EX
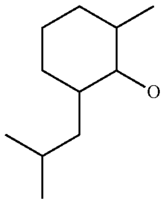
EY
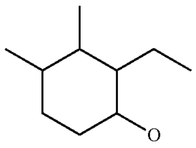
EZ
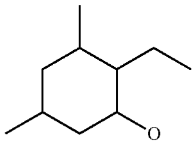
-continued
FA
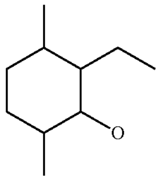
FB
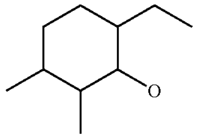
FC
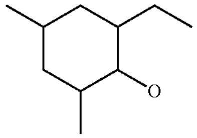
FD
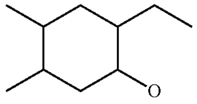
FE
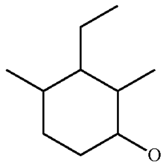
FF
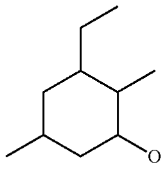
FG
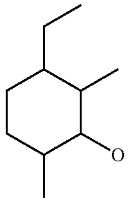
FH
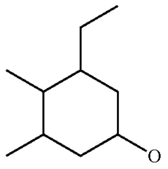
FI
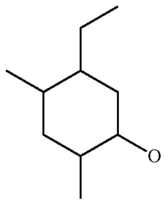

-continued
FJ
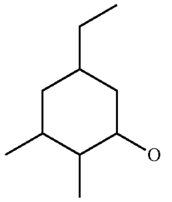
FK
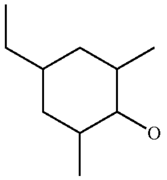
FL
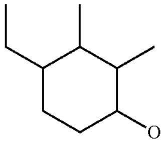
FM
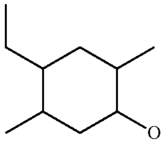
FN
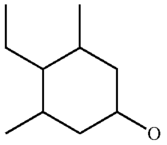
FO
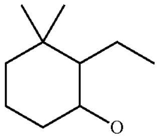
FP
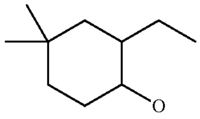
FQ
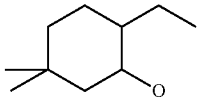
FR
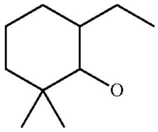
FS
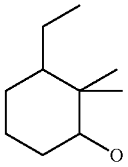
-continued
FT
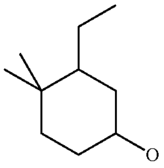
FU
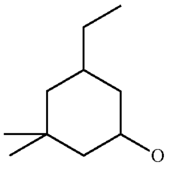
FV
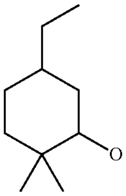
FW
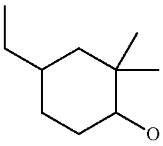
FX
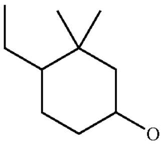
FY
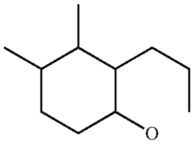
FZ
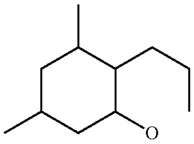
GA
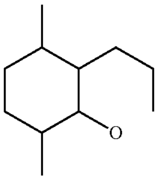
GB
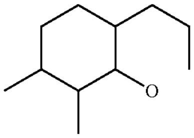

-continued
GC
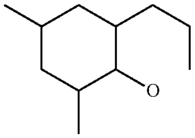
GD
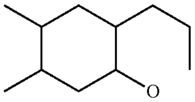
GE
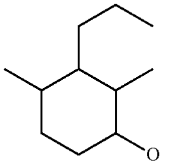
GF
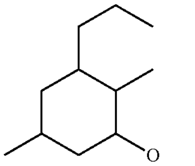
GG
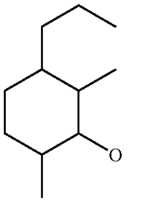
GH
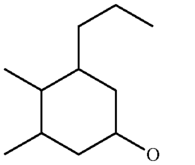
GI
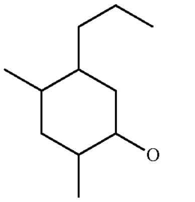
GJ
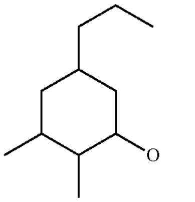
GK
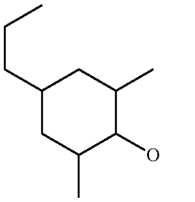
-continued
GL
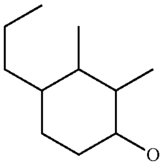
GM
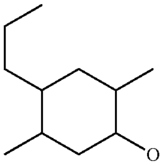
GN
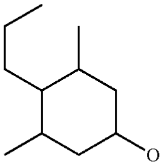
GO
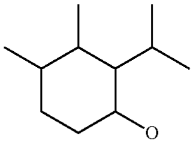
GP
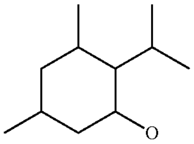
GQ
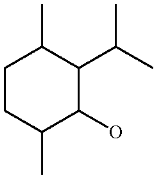
GR
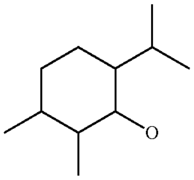
GS
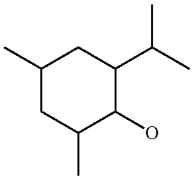
GT
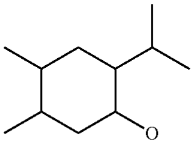

-continued
GU
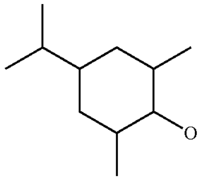
GV
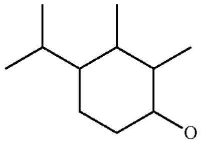
GW
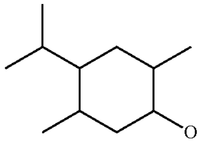
GX
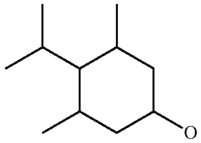
GY
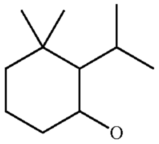
GZ
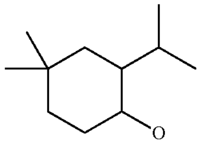
HA
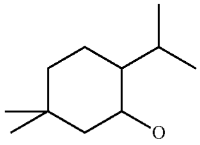
HB
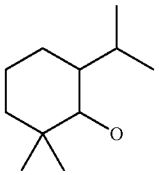
HC
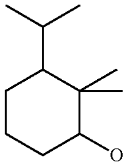
-continued
HD
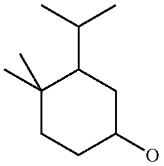
HE
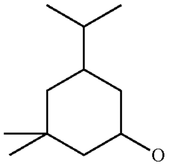
HF
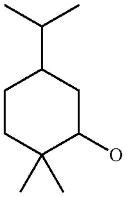
HG
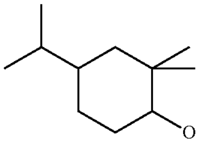
HH
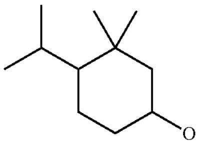
HI
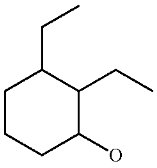
HJ
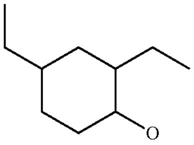
HK
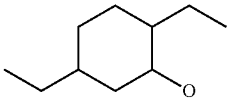
HL
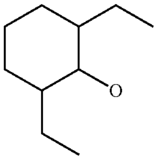

-continued
HM
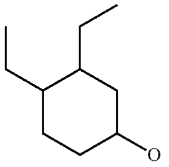
HN
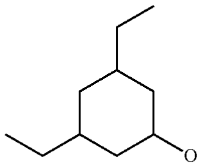
HO
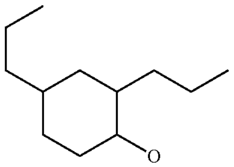
HP
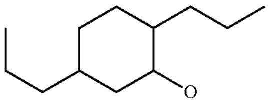
HQ
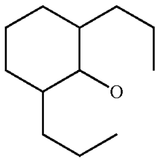
HR
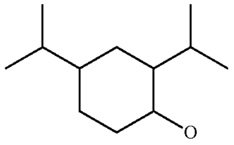
HS
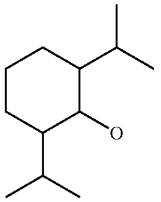
HT
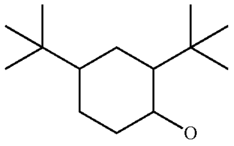
HU
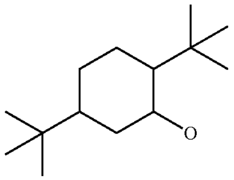
-continued
HV
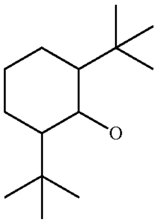
HW
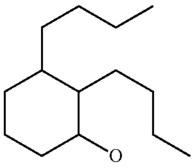
HX
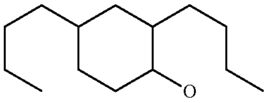
HY
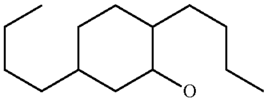
HZ
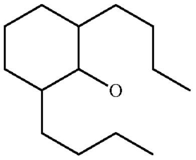
IA
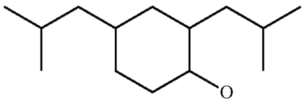
IB
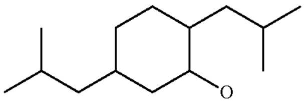
IC
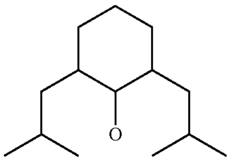
ID
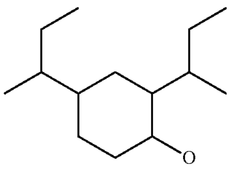
IE
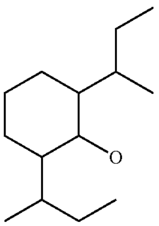

-continued
IF
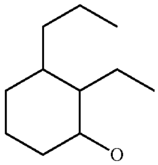
IG
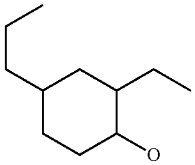
IH
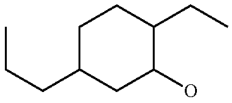
II
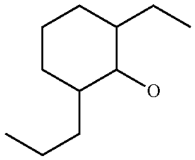
IJ
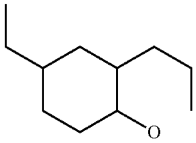
IK
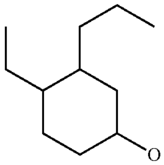
IL
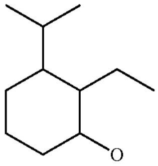
IM
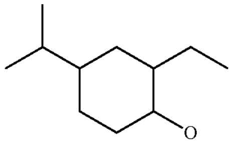
IN
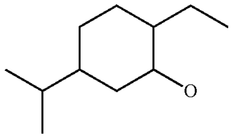
IO
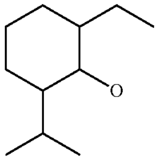
-continued
IP
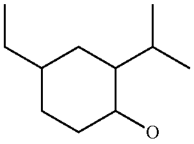
IQ
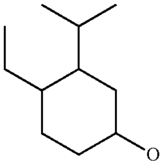
IR
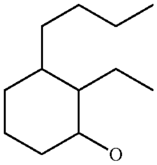
IS
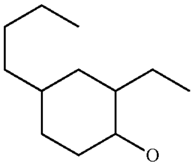
IT
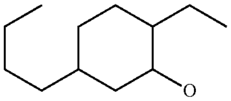
IU
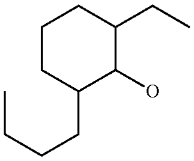
IV
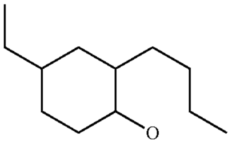
IW
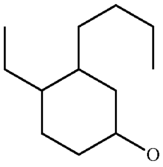
IX
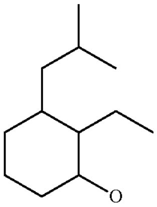

-continued
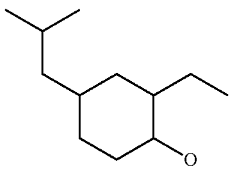
IY
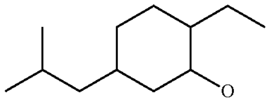
IZ
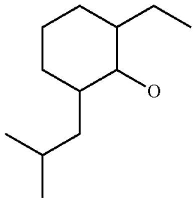
JA
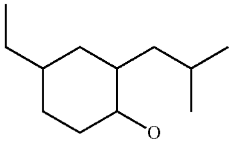
JB
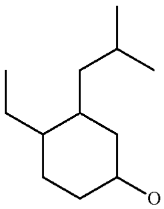
JC
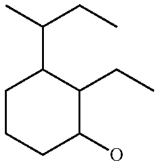
JD
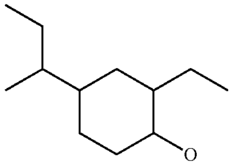
JE
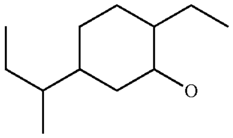
JF
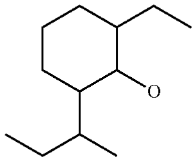
JG
-continued
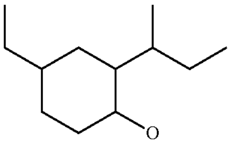
JH
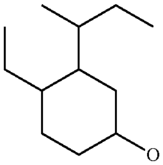
JI
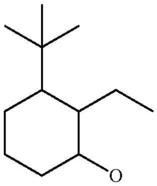
JJ
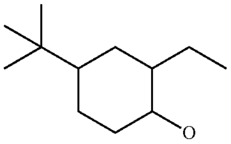
JK
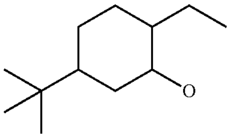
JL
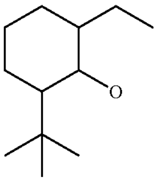
JM
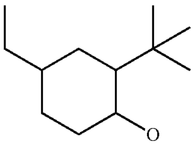
JN
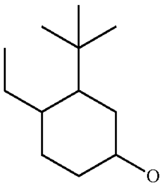
JO
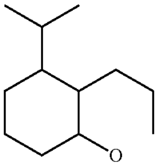
JP -continued
JQ
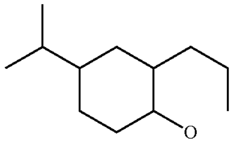
JR
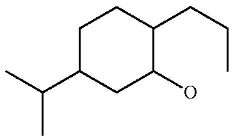
JS
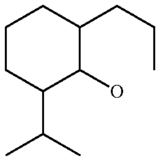
JT
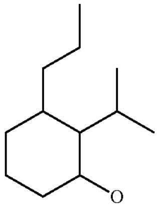
JU
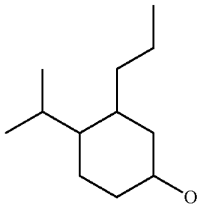
JV
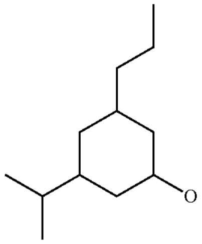
JW
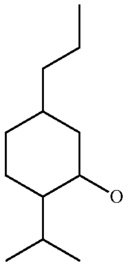
JX
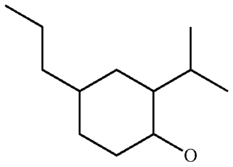
-continued
JY
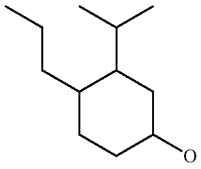
JZ
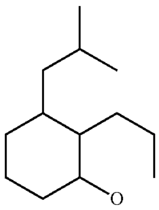
KA
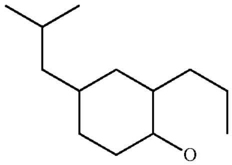
KB
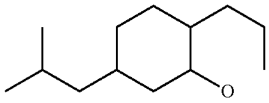
KC
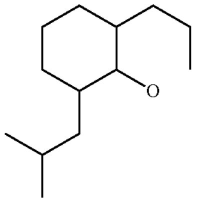
KD
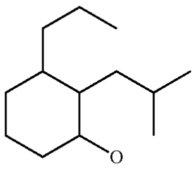
KE
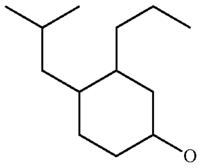
KF
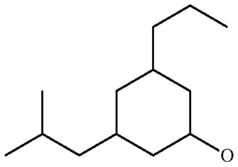

-continued
KG
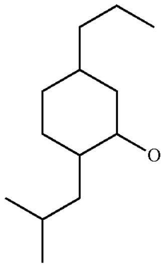
KH
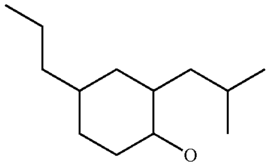
KI
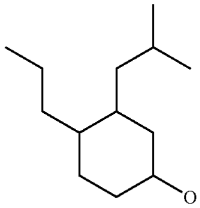
KJ
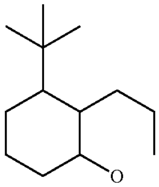
KK
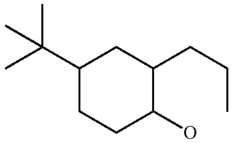
KL
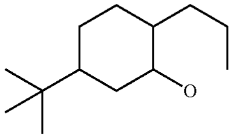
KM
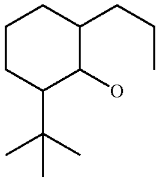
KN
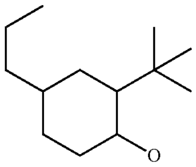
-continued
KO
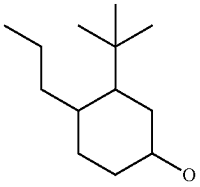
KP
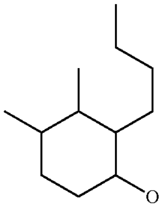
KQ
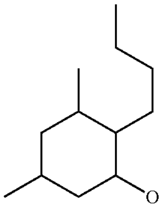
KR
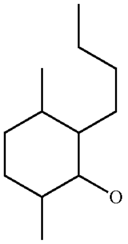
KS
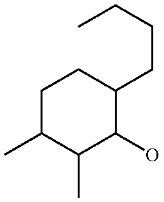
KT
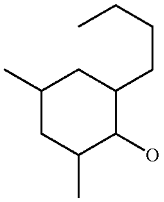
KU
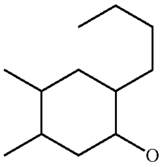

KV
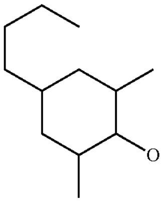
KW
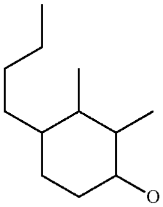
KX
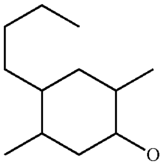
KY
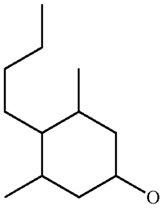
KZ
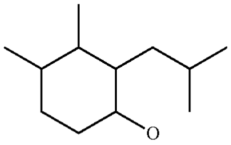
LA
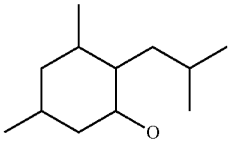
LB
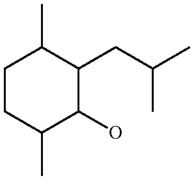
LC
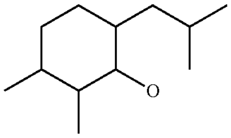
LD
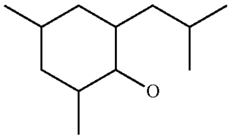
LE
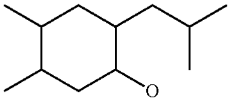
LF
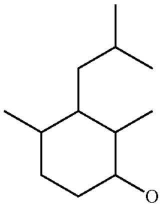
LG
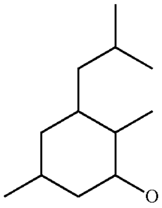
LH
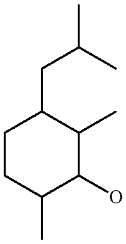
LI
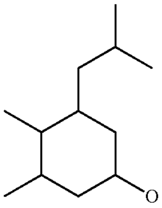
LJ
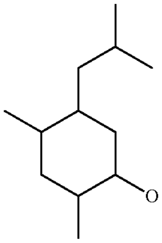
LK
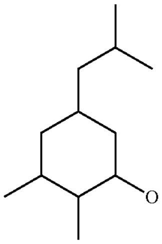

-continued
LL
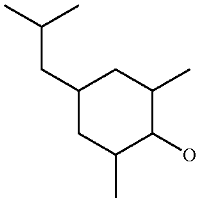
LM
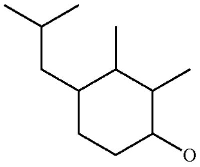
LN
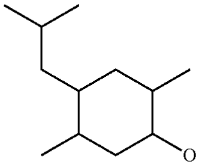
LO
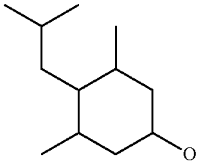
LP
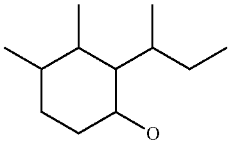
LQ
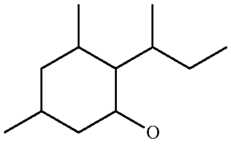
LR
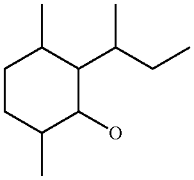
LS
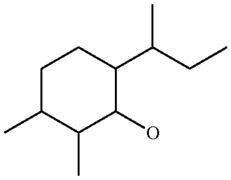
LT
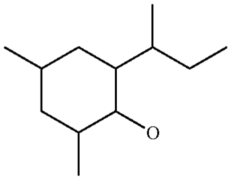
-continued
LU
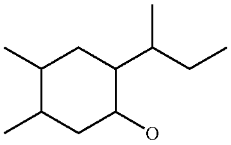
LV
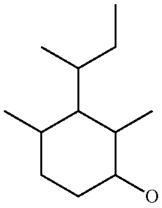
LW
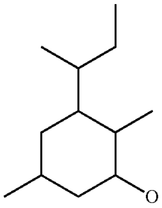
LX
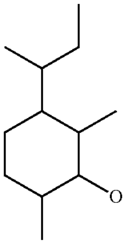
LY
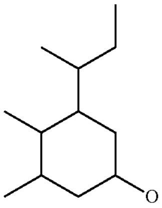
LZ
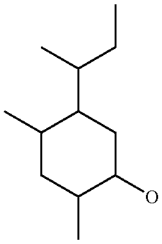
MA
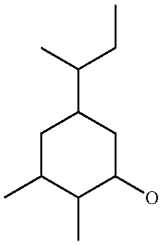

-continued
MB
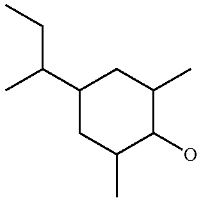
MC
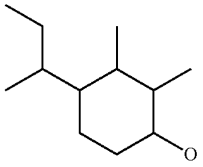
MD
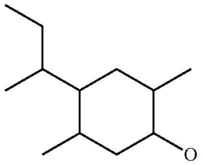
ME
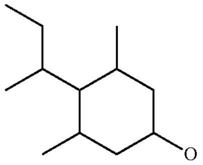
MF
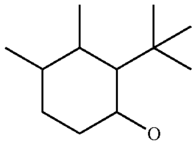
MG
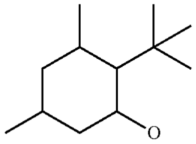
MH
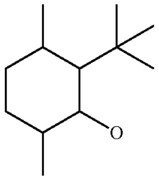
MI
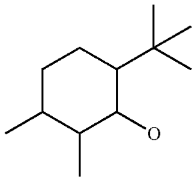
MJ
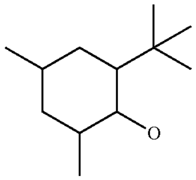
-continued
MK
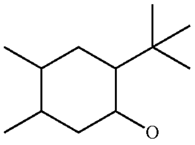
ML
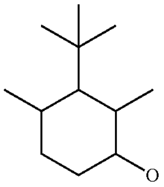
MM
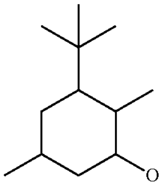
MN
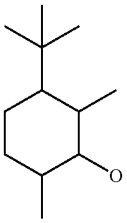
MO
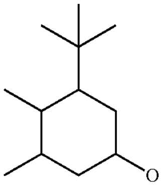
MP
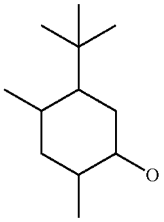
MQ
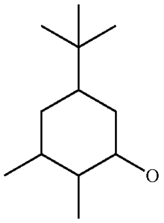
MR
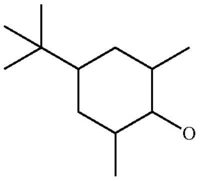

-continued
MS
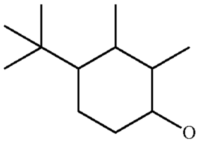
MT
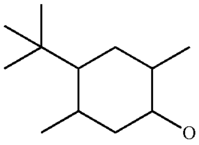
MU
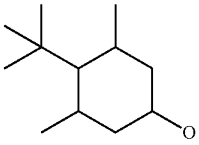
MV
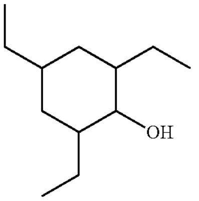
MW
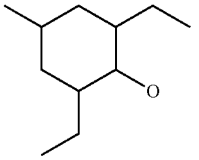
MX
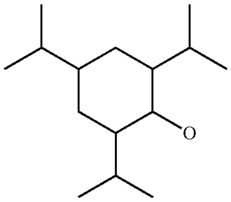
MY
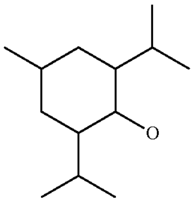
MZ
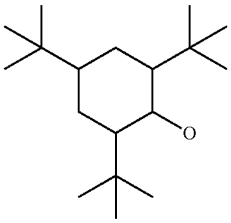
-continued
NA
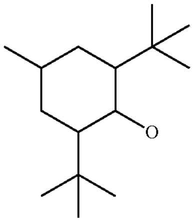
NB
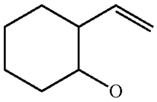
NC
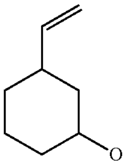
ND
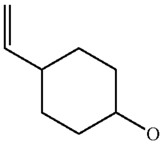
NE
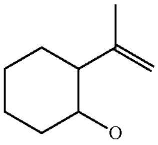
NF
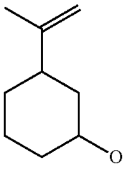
NG
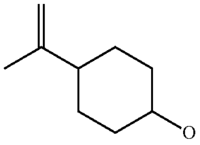
NH
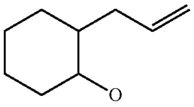
NI
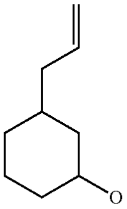

-continued
NJ
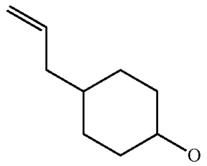
NK
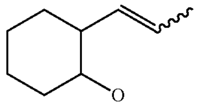
NL
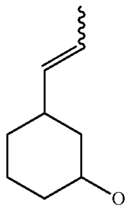
NM
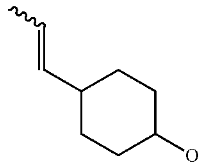
NN
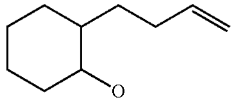
NO
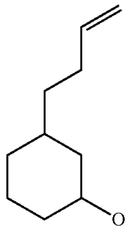
NP
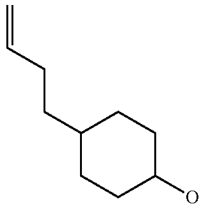
NQ
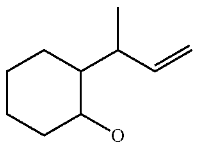
NR
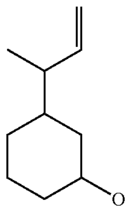
-continued
NS
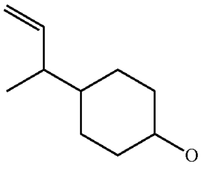
NT
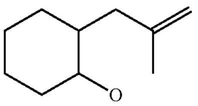
NU
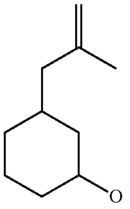
NV
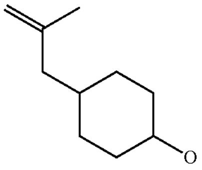
NW
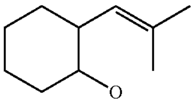
NX
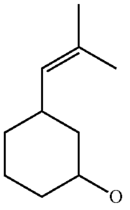
NY
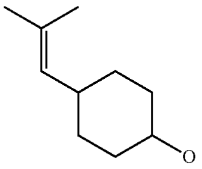
NZ
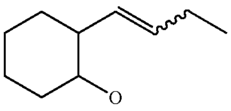
OA
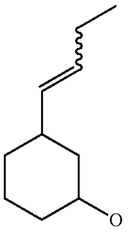

-continued
OB
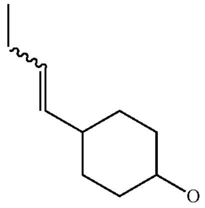
OC
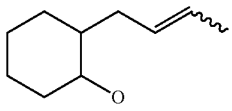
OD
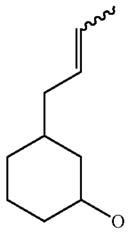
OE
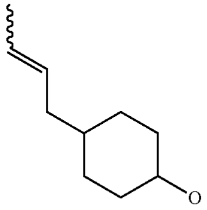
OF
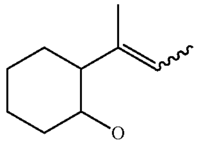
OG
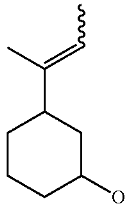
OH
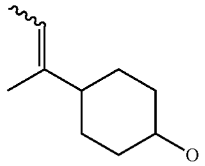
OI
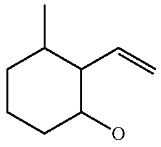
OJ
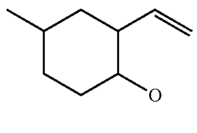
-continued
OK
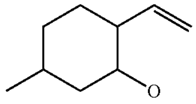
OL
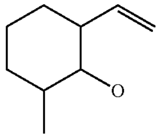
OM
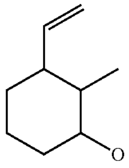
ON
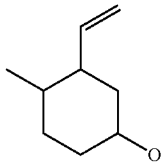
OO
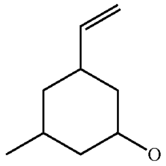
OP
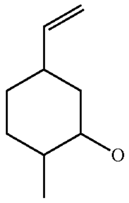
OQ
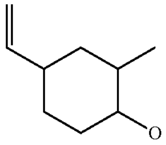
OR
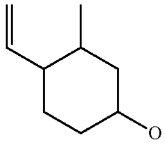
OS
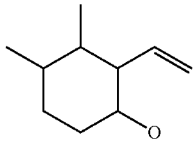
OT
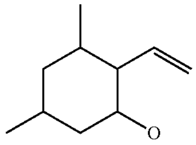

OU
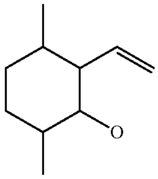
OV
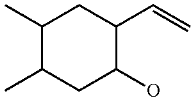
OW
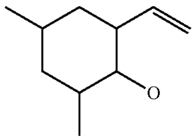
OX
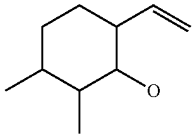
OY
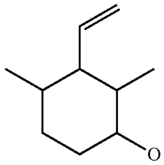
OZ
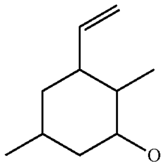
PA
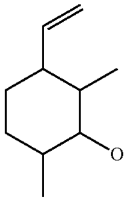
PB
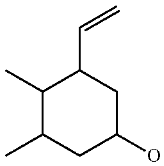
PC
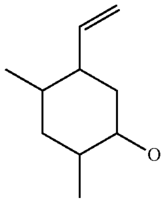
PD
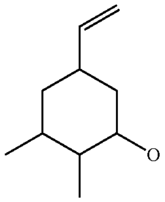
PE
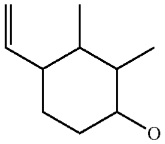
PF
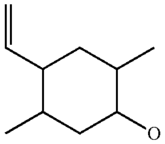
PG
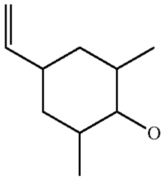
PH
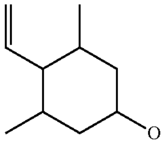
PI
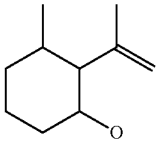
PJ
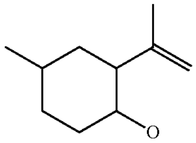
PK
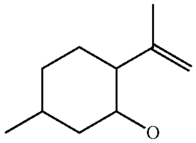
PL
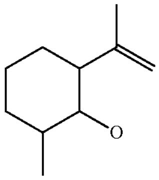

-continued
PM
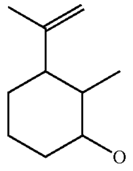
PN
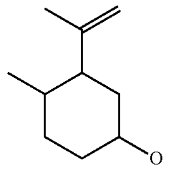
PO
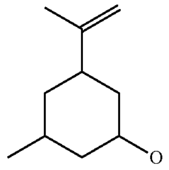
PP
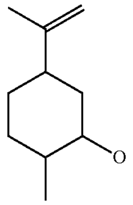
PQ
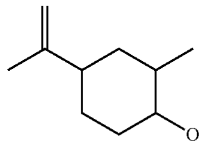
PR
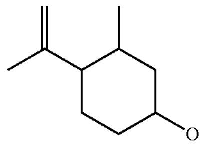
PS
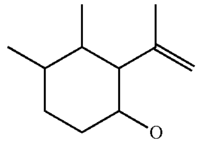
PT
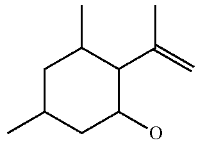
PU
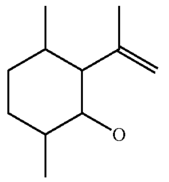
-continued
PV
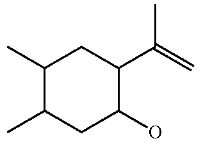
PW
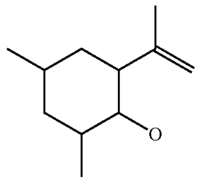
PX
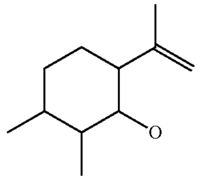
PY
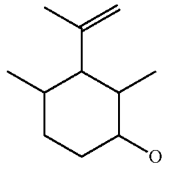
PZ
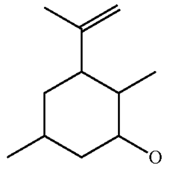
QA
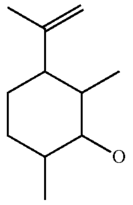
QB
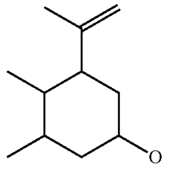
QC
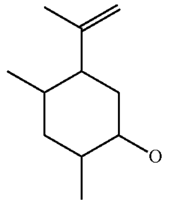

-continued
QD
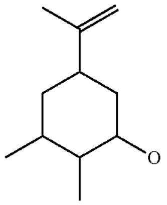
QE
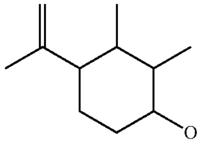
QF
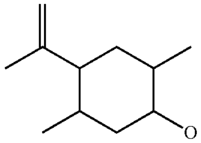
QG
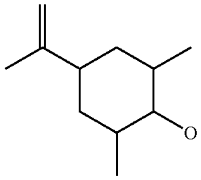
QH
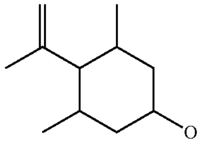
QI
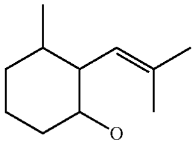
QJ
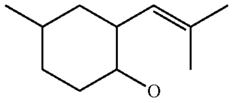
QK
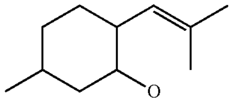
QL
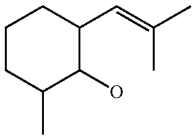
QM
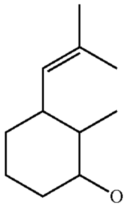
-continued
QN
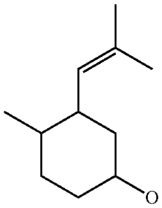
QO
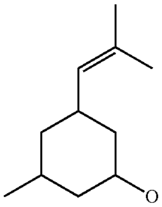
QP
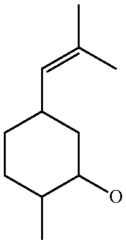
QQ
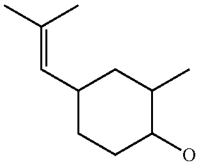
QR
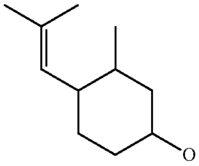
QS
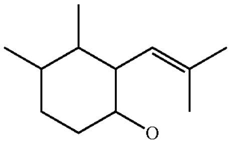
QT
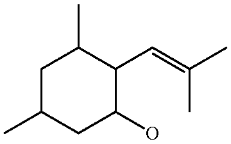
QU
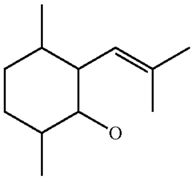

-continued
QV
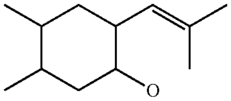
QW
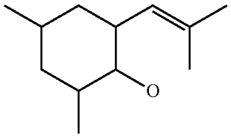
QX
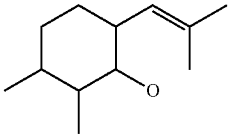
QY
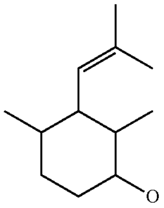
QZ
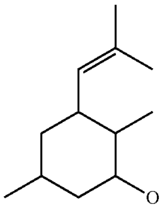
RA
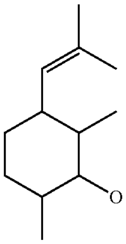
RB
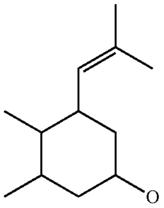
RC
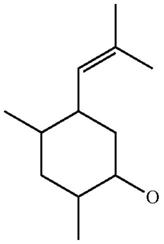
-continued
RD
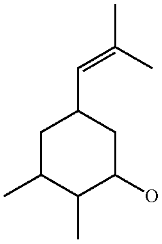
RE
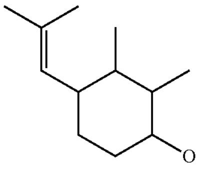
RF
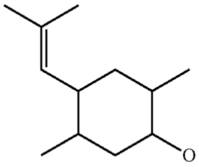
RG
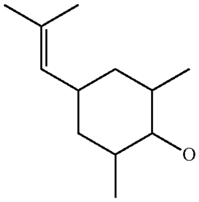
RH
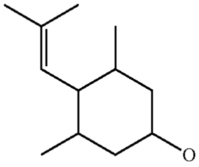
RI
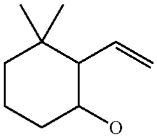
RJ
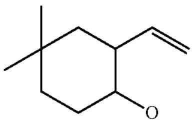
RK
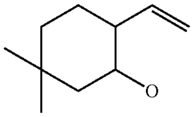
RL
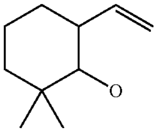

-continued
RM
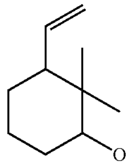
RN
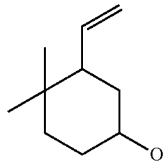
RO
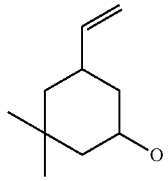
RP
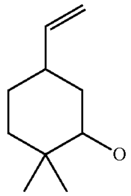
RQ
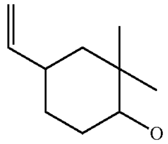
RR
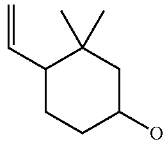
RS
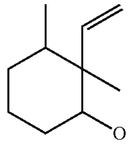
RT
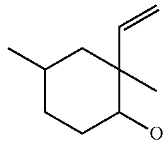
RU
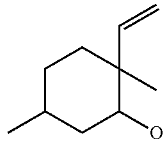
-continued
RV
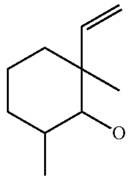
RW
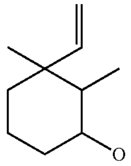
RX
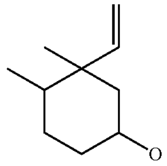
RY
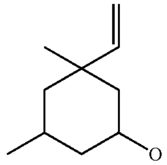
RZ
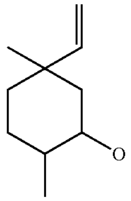
SA
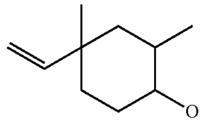
SB
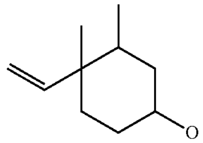
SC
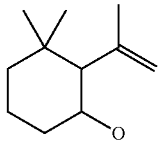
SD
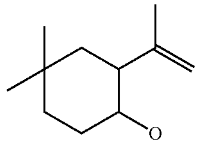

-continued
SE
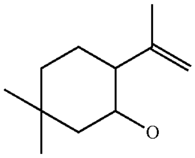
SF
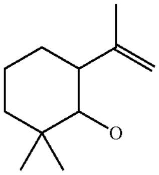
SG
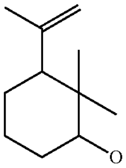
SH
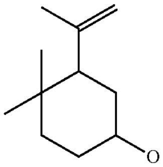
SI
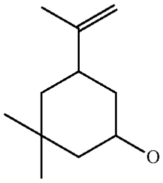
SJ
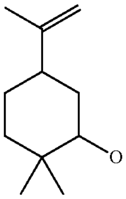
SK
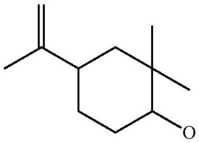
SL
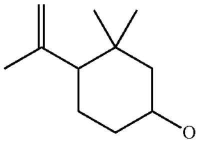
SM
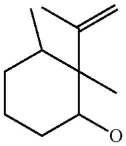
-continued
SN
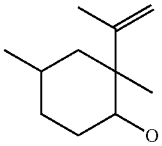
SO
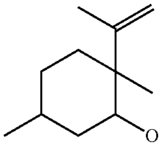
SP
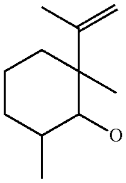
SQ
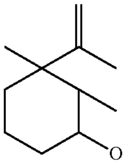
SR
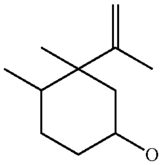
SS
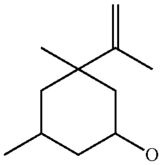
ST
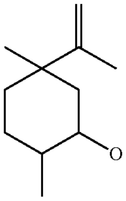
SU
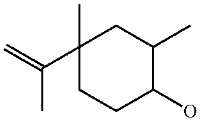
SV
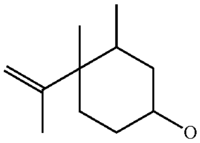

-continued
SW
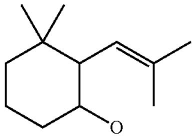
SX
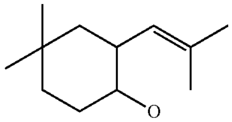
SY
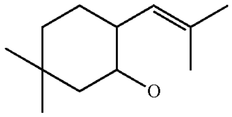
SZ
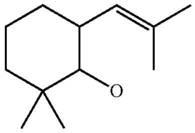
TA
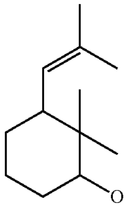
TB
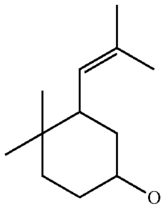
TC
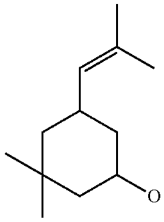
TD
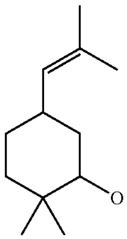
-continued
TE
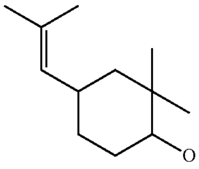
TF
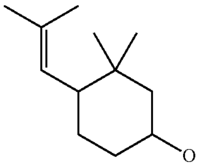
TG
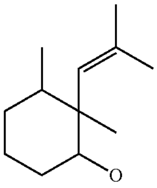
TH
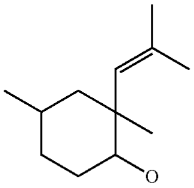
TI
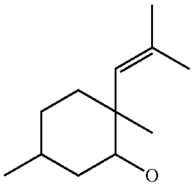
TJ
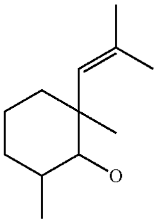
TK
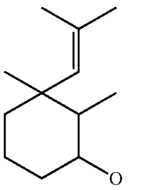
TL
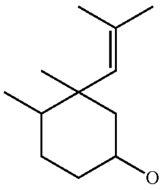

-continued
TM
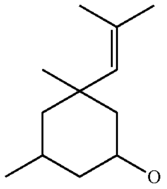
TN
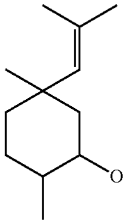
TO
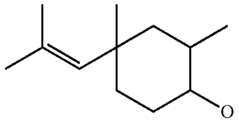
TP
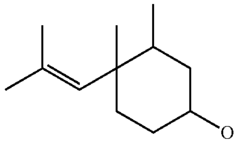
TQ
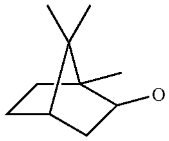
TR
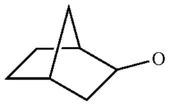
TS
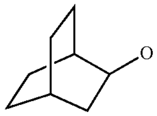
TT
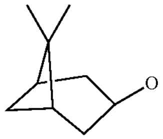
TU
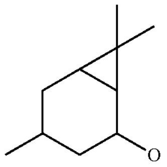
-continued
TV
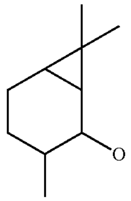
TW
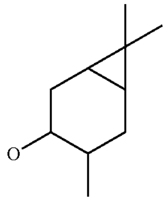
TX
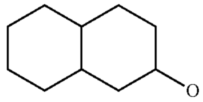
TY
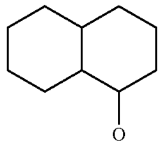
TZ
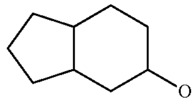
UA
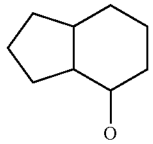
Preferred compounds of formula (I), (Carb-I), (Carb-II) and (Carb-II-R1H) are those in which B denotes $NR^1R^2$, wherein preferably $R^1$ denotes hydrogen, and wherein $NR^2$ is a radical chosen from the following list "N":
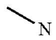
1
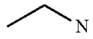
2
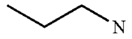
3
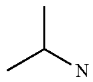
4
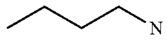
5
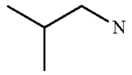
6

-continued
7
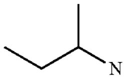
8
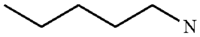
9
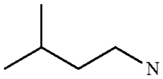
10
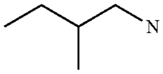
11
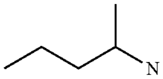
12
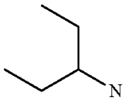
13
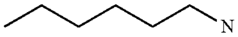
14
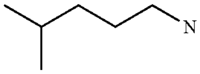
15
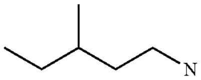
16
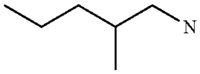
17
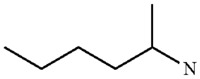
18
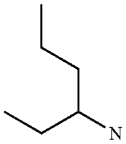
19
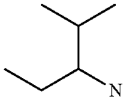
20
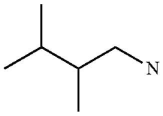
21
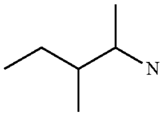
22
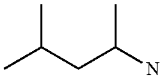
-continued
23
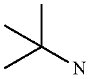
24
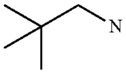
25
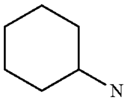
26
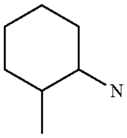
27
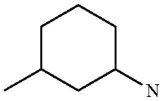
28
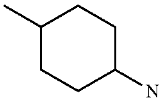
29
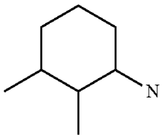
30
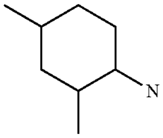
31
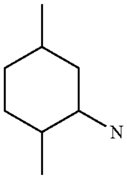
32
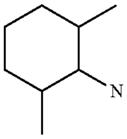
33
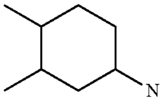
34
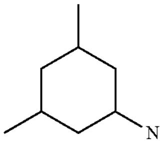

-continued
35
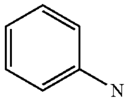
36
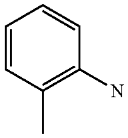
37
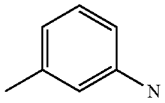
38
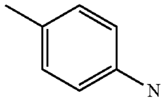
39
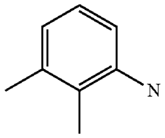
40
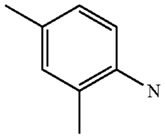
41
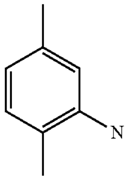
42
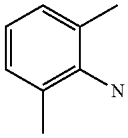
43
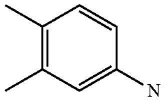
44
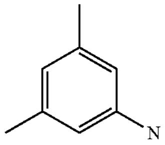
45
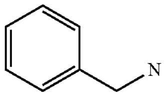
-continued
46
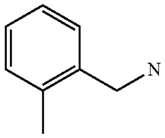
47
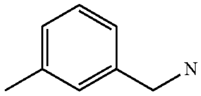
48
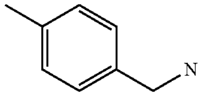
49
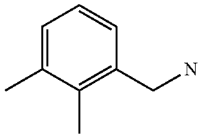
50
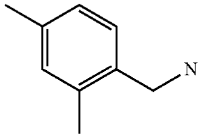
51
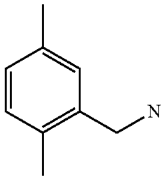
52
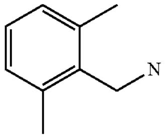
53
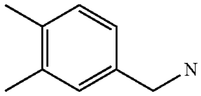
54
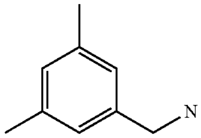
55
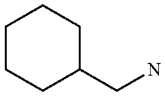
56
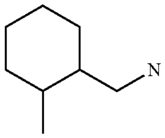

-continued
57
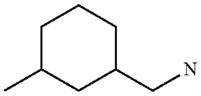
58
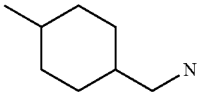
59
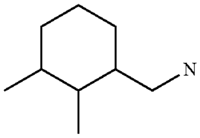
60
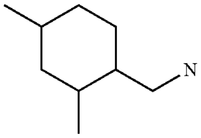
61
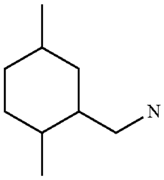
62
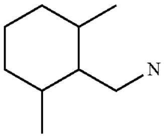
63
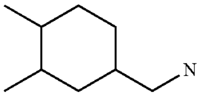
64
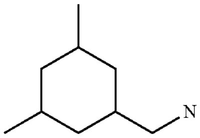
65
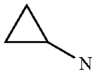
66
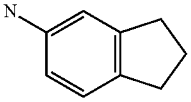
67
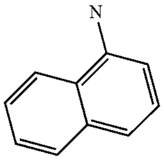
-continued
68
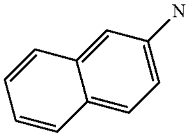
69
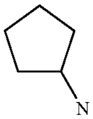
70
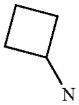
71
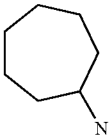
72
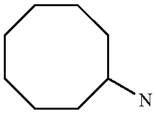
73
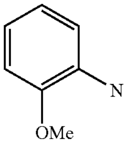
74
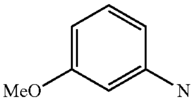
75
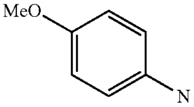
76
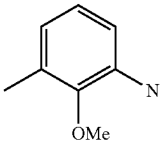
77
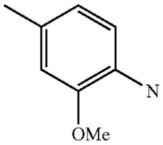
78
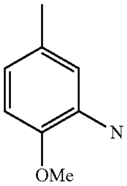

-continued
79
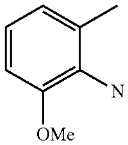
80
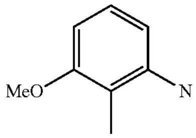
81
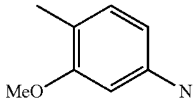
82
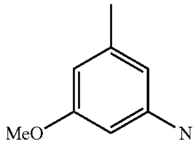
83
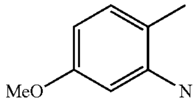
84
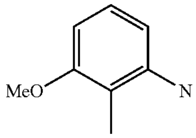
85
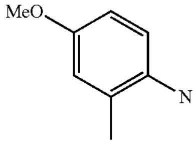
86
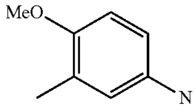
87
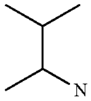
88
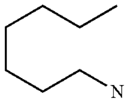
89
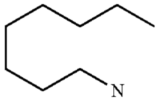
90
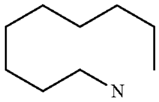
-continued
91
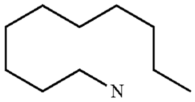
92
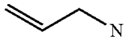
93
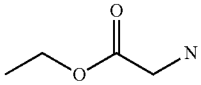
94
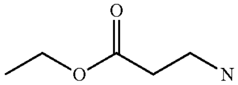
95
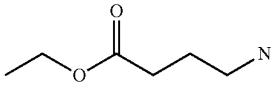
96
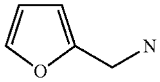
97
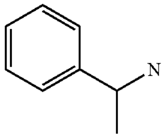
98
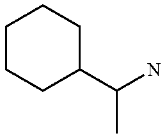
99
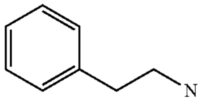
100
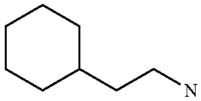
101
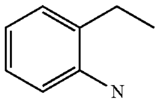
102
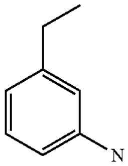
103
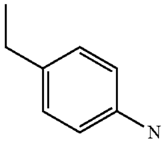

-continued
104
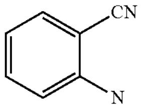
105
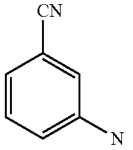
106
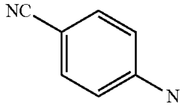
107
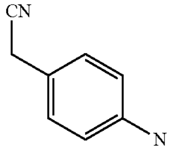
108
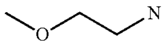
109
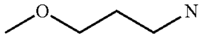
110
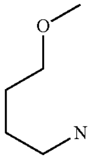
111
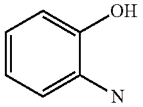
112
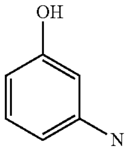
113
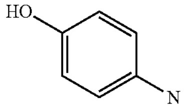
114
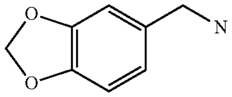
115
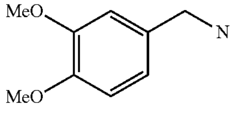
116
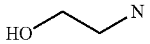
117
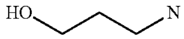
-continued
118
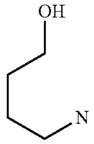
119
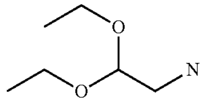
120
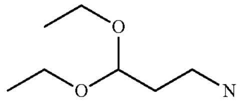
121
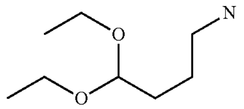
122
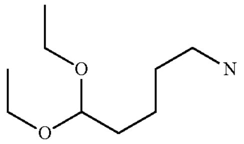
123
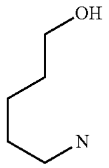
124
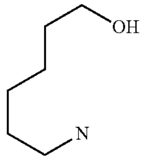
125
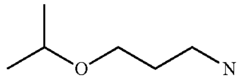
126
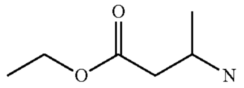
127
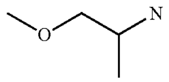
128
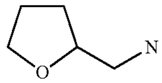
129
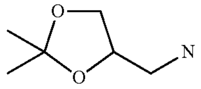
130
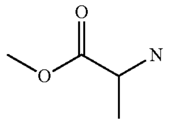

-continued

131

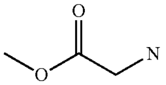

132

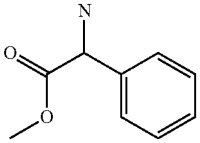

133

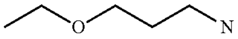

134

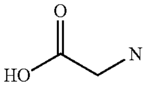

135

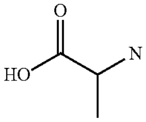

136

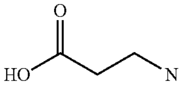

137

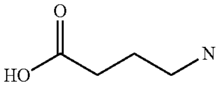

138

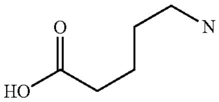

139

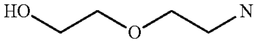

140

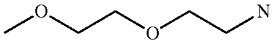

141

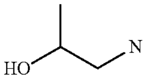

142

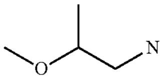

143

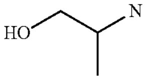

144

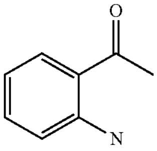

145

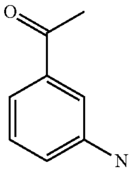

-continued

146

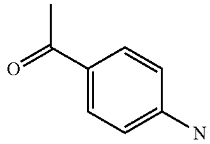

147

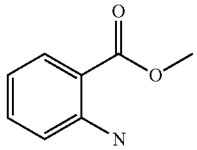

148

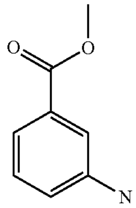

149

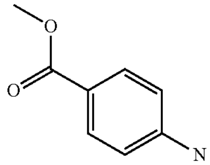

150

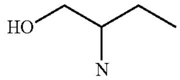

151

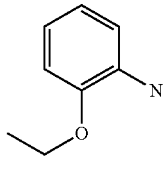

152

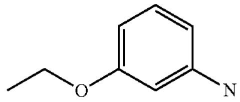

153

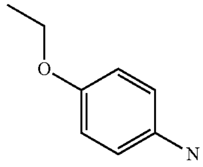

154

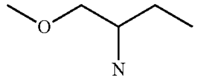

The CyO-N-code as defined and used hereinafter specifies a single individual compound of formula (Carb-II-R1H) in accordance with the present invention. A specific compound is defined by the CyO-N-code by selecting a radical from list "CyO" as substituent A in formula (I) and selecting in substituent B a radical from list "N" as group $NR^2$, whereby $R^1$ of substituent B denotes hydrogen.

By way of example, said CyO-N-code is illustrated by the following compounds:

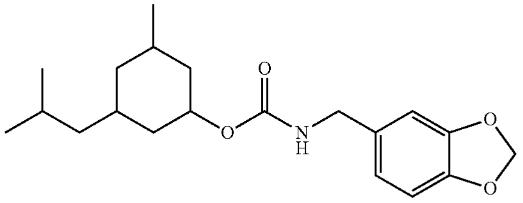

CyO-N-code: CA114

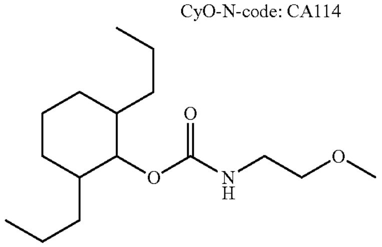

CyO-N-code: HQ108

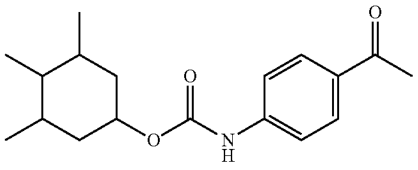

CyO-N-code: BJ146

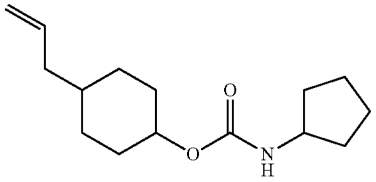

CyO-N-code: NJ69

Further preferred compounds of formula (I) are those in which B denotes $NHR^2$, wherein $NR^2$ corresponds to radical 1 of list "N", above, and A of formula (I) denotes one radical selected from list "CyO", above.

Further preferred compounds of formula (I) are those in which B denotes $NHR^2$, wherein $NR^2$ corresponds to radical 2 of list "N", above, and A of formula (I) denotes one radical selected from list "CyO", above.

Further preferred compounds of formula (I) are those in which B denotes $NHR^2$, wherein $NR^2$ corresponds to radical 3 of list "N", above, and A of formula (I) denotes one radical selected from list "CyO", above.

Further preferred compounds of formula (I) are those in which B denotes $NHR^2$, wherein $NR^2$ corresponds to radical 4 of list "N", above, and A of formula (I) denotes one radical selected from list "CyO", above.

Further preferred compounds of formula (I) are those in which B denotes $NHR^2$, wherein $NR^2$ corresponds to radical 5 of list "N", above, and A of formula (I) denotes one radical selected from list "CyO", above.

Further preferred compounds of formula (I) are those in which B denotes $NHR^2$, wherein $NR^2$ corresponds to radical 6 of list "N", above, and A of formula (I) denotes one radical selected from list "CyO", above.

Further preferred compounds of formula (I) are those in which B denotes $NHR^2$, wherein $NR^2$ corresponds to radical 7 of list "N", above, and A of formula (I) denotes one radical selected from list "CyO", above.

Further preferred compounds of formula (I) are those in which B denotes $NHR^2$, wherein $NR^2$ corresponds to radical 8 of list "N", above, and A of formula (I) denotes one radical selected from list "CyO", above.

Further preferred compounds of formula (I) are those in which B denotes $NHR^2$, wherein $NR^2$ corresponds to radical 9 of list "N", above, and A of formula (I) denotes one radical selected from list "CyO", above.

Further preferred compounds of formula (I) are those in which B denotes $NHR^2$, wherein $NR^2$ corresponds to radical 10 of list "N", above, and A of formula (I) denotes one radical selected from list "CyO", above.

Further preferred compounds of formula (I) are those in which B denotes $NHR^2$, wherein $NR^2$ corresponds to radical 11 of list "N", above, and A of formula (I) denotes one radical selected from list "CyO", above.

Further preferred compounds of formula (I) are those in which B denotes $NHR^2$, wherein $NR^2$ corresponds to radical 12 of list "N", above, and A of formula (I) denotes one radical selected from list "CyO", above.

Further preferred compounds of formula (I) are those in which B denotes $NHR^2$, wherein $NR^2$ corresponds to radical 13 of list "N", above, and A of formula (I) denotes one radical selected from list "CyO", above.

Further preferred compounds of formula (I) are those in which B denotes $NHR^2$, wherein $NR^2$ corresponds to radical 14 of list "N", above, and A of formula (I) denotes one radical selected from list "CyO", above.

Further preferred compounds of formula (I) are those in which B denotes $NHR^2$, wherein $NR^2$ corresponds to radical 15 of list "N", above, and A of formula (I) denotes one radical selected from list "CyO", above.

Further preferred compounds of formula (I) are those in which B denotes $NHR^2$, wherein $NR^2$ corresponds to radical 16 of list "N", above, and A of formula (I) denotes one radical selected from list "CyO", above.

Further preferred compounds of formula (I) are those in which B denotes $NHR^2$, wherein $NR^2$ corresponds to radical 17 of list "N", above, and A of formula (I) denotes one radical selected from list "CyO", above.

Further preferred compounds of formula (I) are those in which B denotes $NHR^2$, wherein $NR^2$ corresponds to radical 18 of list "N", above, and A of formula (I) denotes one radical selected from list "CyO", above.

Further preferred compounds of formula (I) are those in which B denotes $NHR^2$, wherein $NR^2$ corresponds to radical 19 of list "N", above, and A of formula (I) denotes one radical selected from list "CyO", above.

Further preferred compounds of formula (I) are those in which B denotes $NHR^2$, wherein $NR^2$ corresponds to radical 20 of list "N", above, and A of formula (I) denotes one radical selected from list "CyO", above.

Further preferred compounds of formula (I) are those in which B denotes $NHR^2$, wherein $NR^2$ corresponds to radical 21 of list "N", above, and A of formula (I) denotes one radical selected from list "CyO", above.

Further preferred compounds of formula (I) are those in which B denotes $NHR^2$, wherein $NR^2$ corresponds to radical 22 of list "N", above, and A of formula (I) denotes one radical selected from list "CyO", above.

Further preferred compounds of formula (I) are those in which B denotes $NHR^2$, wherein $NR^2$ corresponds to radical 23 of list "N", above, and A of formula (I) denotes one radical selected from list "CyO", above.

Further preferred compounds of formula (I) are those in which B denotes $NHR^2$, wherein $NR^2$ corresponds to radical 24 of list "N", above, and A of formula (I) denotes one radical selected from list "CyO", above.

Further preferred compounds of formula (I) are those in which B denotes $NHR^2$, wherein $NR^2$ corresponds to radical 25 of list "N", above, and A of formula (I) denotes one radical selected from list "CyO", above.

Further preferred compounds of formula (I) are those in which B denotes $NHR^2$, wherein $NR^2$ corresponds to radical 26 of list "N", above, and A of formula (I) denotes one radical selected from list "CyO", above.

Further preferred compounds of formula (I) are those in which B denotes $NHR^2$, wherein $NR^2$ corresponds to radical 27 of list "N", above, and A of formula (I) denotes one radical selected from list "CyO", above.

Further preferred compounds of formula (I) are those in which B denotes $NHR^2$, wherein $NR^2$ corresponds to radical 28 of list "N", above, and A of formula (I) denotes one radical selected from list "CyO", above.

Further preferred compounds of formula (I) are those in which B denotes $NHR^2$, wherein $NR^2$ corresponds to radical 29 of list "N", above, and A of formula (I) denotes one radical selected from list "CyO", above.

Further preferred compounds of formula (I) are those in which B denotes $NHR^2$, wherein $NR^2$ corresponds to radical 30 of list "N", above, and A of formula (I) denotes one radical selected from list "CyO", above.

Further preferred compounds of formula (I) are those in which B denotes $NHR^2$, wherein $NR^2$ corresponds to radical 31 of list "N", above, and A of formula (I) denotes one radical selected from list "CyO", above.

Further preferred compounds of formula (I) are those in which B denotes $NHR^2$, wherein $NR^2$ corresponds to radical 32 of list "N", above, and A of formula (I) denotes one radical selected from list "CyO", above.

Further preferred compounds of formula (I) are those in which B denotes $NHR^2$, wherein $NR^2$ corresponds to radical 33 of list "N", above, and A of formula (I) denotes one radical selected from list "CyO", above.

Further preferred compounds of formula (I) are those in which B denotes $NHR^2$, wherein $NR^2$ corresponds to radical 34 of list "N", above, and A of formula (I) denotes one radical selected from list "CyO", above.

Further preferred compounds of formula (I) are those in which B denotes $NHR^2$, wherein $NR^2$ corresponds to radical 35 of list "N", above, and A of formula (I) denotes one radical selected from list "CyO", above.

Further preferred compounds of formula (I) are those in which B denotes $NHR^2$, wherein $NR^2$ corresponds to radical 36 of list "N", above, and A of formula (I) denotes one radical selected from list "CyO", above.

Further preferred compounds of formula (I) are those in which B denotes $NHR^2$, wherein $NR^2$ corresponds to radical 37 of list "N", above, and A of formula (I) denotes one radical selected from list "CyO", above.

Further preferred compounds of formula (I) are those in which B denotes $NHR^2$, wherein $NR^2$ corresponds to radical 38 of list "N", above, and A of formula (I) denotes one radical selected from list "CyO", above.

Further preferred compounds of formula (I) are those in which B denotes $NHR^2$, wherein $NR^2$ corresponds to radical 39 of list "N", above, and A of formula (I) denotes one radical selected from list "CyO", above.

Further preferred compounds of formula (I) are those in which B denotes $NHR^2$, wherein $NR^2$ corresponds to radical 40 of list "N", above, and A of formula (I) denotes one radical selected from list "CyO", above.

Further preferred compounds of formula (I) are those in which B denotes $NHR^2$, wherein $NR^2$ corresponds to radical 41 of list "N", above, and A of formula (I) denotes one radical selected from list "CyO", above.

Further preferred compounds of formula (I) are those in which B denotes $NHR^2$, wherein $NR^2$ corresponds to radical 42 of list "N", above, and A of formula (I) denotes one radical selected from list "CyO", above.

Further preferred compounds of formula (I) are those in which B denotes $NHR^2$, wherein $NR^2$ corresponds to radical 43 of list "N", above, and A of formula (I) denotes one radical selected from list "CyO", above.

Further preferred compounds of formula (I) are those in which B denotes $NHR^2$, wherein $NR^2$ corresponds to radical 44 of list "N", above, and A of formula (I) denotes one radical selected from list "CyO", above.

Further preferred compounds of formula (I) are those in which B denotes $NHR^2$, wherein $NR^2$ corresponds to radical 45 of list "N", above, and A of formula (I) denotes one radical selected from list "CyO", above.

Further preferred compounds of formula (I) are those in which B denotes $NHR^2$, wherein $NR^2$ corresponds to radical 46 of list "N", above, and A of formula (I) denotes one radical selected from list "CyO", above.

Further preferred compounds of formula (I) are those in which B denotes $NHR^2$, wherein $NR^2$ corresponds to radical 47 of list "N", above, and A of formula (I) denotes one radical selected from list "CyO", above.

Further preferred compounds of formula (I) are those in which B denotes $NHR^2$, wherein $NR^2$ corresponds to radical 48 of list "N", above, and A of formula (I) denotes one radical selected from list "CyO", above.

Further preferred compounds of formula (I) are those in which B denotes $NHR^2$, wherein $NR^2$ corresponds to radical 49 of list "N", above, and A of formula (I) denotes one radical selected from list "CyO", above.

Further preferred compounds of formula (I) are those in which B denotes $NHR^2$, wherein $NR^2$ corresponds to radical 50 of list "N", above, and A of formula (I) denotes one radical selected from list "CyO", above.

Further preferred compounds of formula (I) are those in which B denotes $NHR^2$, wherein $NR^2$ corresponds to radical 51 of list "N", above, and A of formula (I) denotes one radical selected from list "CyO", above.

Further preferred compounds of formula (I) are those in which B denotes $NHR^2$, wherein $NR^2$ corresponds to radical 52 of list "N", above, and A of formula (I) denotes one radical selected from list "CyO", above.

Further preferred compounds of formula (I) are those in which B denotes $NHR^2$, wherein $NR^2$ corresponds to radical 53 of list "N", above, and A of formula (I) denotes one radical selected from list "CyO", above.

Further preferred compounds of formula (I) are those in which B denotes $NHR^2$, wherein $NR^2$ corresponds to radical 54 of list "N", above, and A of formula (I) denotes one radical selected from list "CyO", above.

Further preferred compounds of formula (I) are those in which B denotes $NHR^2$, wherein $NR^2$ corresponds to radical 55 of list "N", above, and A of formula (I) denotes one radical selected from list "CyO", above.

Further preferred compounds of formula (I) are those in which B denotes $NHR^2$, wherein $NR^2$ corresponds to radical 56 of list "N", above, and A of formula (I) denotes one radical selected from list "CyO", above.

Further preferred compounds of formula (I) are those in which B denotes $NHR^2$, wherein $NR^2$ corresponds to radical 57 of list "N", above, and A of formula (I) denotes one radical selected from list "CyO", above.

Further preferred compounds of formula (I) are those in which B denotes $NHR^2$, wherein $NR^2$ corresponds to radical 58 of list "N", above, and A of formula (I) denotes one radical selected from list "CyO", above.

Further preferred compounds of formula (I) are those in which B denotes $NHR^2$, wherein $NR^2$ corresponds to radical 59 of list "N", above, and A of formula (I) denotes one radical selected from list "CyO", above.

Further preferred compounds of formula (I) are those in which B denotes $NHR^2$, wherein $NR^2$ corresponds to radical 60 of list "N", above, and A of formula (I) denotes one radical selected from list "CyO", above.

Further preferred compounds of formula (I) are those in which B denotes $NHR^2$, wherein $NR^2$ corresponds to radical 61 of list "N", above, and A of formula (I) denotes one radical selected from list "CyO", above.

Further preferred compounds of formula (I) are those in which B denotes $NHR^2$, wherein $NR^2$ corresponds to radical 62 of list "N", above, and A of formula (I) denotes one radical selected from list "CyO", above.

Further preferred compounds of formula (I) are those in which B denotes $NHR^2$, wherein $NR^2$ corresponds to radical 63 of list "N", above, and A of formula (I) denotes one radical selected from list "CyO", above.

Further preferred compounds of formula (I) are those in which B denotes $NHR^2$, wherein $NR^2$ corresponds to radical 64 of list "N", above, and A of formula (I) denotes one radical selected from list "CyO", above.

Further preferred compounds of formula (I) are those in which B denotes $NHR^2$, wherein $NR^2$ corresponds to radical 65 of list "N", above, and A of formula (I) denotes one radical selected from list "CyO", above.

Further preferred compounds of formula (I) are those in which B denotes $NHR^2$, wherein $NR^2$ corresponds to radical 66 of list "N", above, and A of formula (I) denotes one radical selected from list "CyO", above.

Further preferred compounds of formula (I) are those in which B denotes $NHR^2$, wherein $NR^2$ corresponds to radical 67 of list "N", above, and A of formula (I) denotes one radical selected from list "CyO", above.

Further preferred compounds of formula (I) are those in which B denotes $NHR^2$, wherein $NR^2$ corresponds to radical 68 of list "N", above, and A of formula (I) denotes one radical selected from list "CyO", above.

Further preferred compounds of formula (I) are those in which B denotes $NHR^2$, wherein $NR^2$ corresponds to radical 69 of list "N", above, and A of formula (I) denotes one radical selected from list "CyO", above.

Further preferred compounds of formula (I) are those in which B denotes $NHR^2$, wherein $NR^2$ corresponds to radical 70 of list "N", above, and A of formula (I) denotes one radical selected from list "CyO", above.

Further preferred compounds of formula (I) are those in which B denotes $NHR^2$, wherein $NR^2$ corresponds to radical 71 of list "N", above, and A of formula (I) denotes one radical selected from list "CyO", above.

Further preferred compounds of formula (I) are those in which B denotes $NHR^2$, wherein $NR^2$ corresponds to radical 72 of list "N", above, and A of formula (I) denotes one radical selected from list "CyO", above.

Further preferred compounds of formula (I) are those in which B denotes $NHR^2$, wherein $NR^2$ corresponds to radical 73 of list "N", above, and A of formula (I) denotes one radical selected from list "CyO", above.

Further preferred compounds of formula (I) are those in which B denotes $NHR^2$, wherein $NR^2$ corresponds to radical 74 of list "N", above, and A of formula (I) denotes one radical selected from list "CyO", above.

Further preferred compounds of formula (I) are those in which B denotes $NHR^2$, wherein $NR^2$ corresponds to radical 75 of list "N", above, and A of formula (I) denotes one radical selected from list "CyO", above.

Further preferred compounds of formula (I) are those in which B denotes $NHR^2$, wherein $NR^2$ corresponds to radical 76 of list "N", above, and A of formula (I) denotes one radical selected from list "CyO", above.

Further preferred compounds of formula (I) are those in which B denotes $NHR^2$, wherein $NR^2$ corresponds to radical 77 of list "N", above, and A of formula (I) denotes one radical selected from list "CyO", above.

Further preferred compounds of formula (I) are those in which B denotes $NHR^2$, wherein $NR^2$ corresponds to radical 78 of list "N", above, and A of formula (I) denotes one radical selected from list "CyO", above.

Further preferred compounds of formula (I) are those in which B denotes $NHR^2$, wherein $NR^2$ corresponds to radical 79 of list "N", above, and A of formula (I) denotes one radical selected from list "CyO", above.

Further preferred compounds of formula (I) are those in which B denotes $NHR^2$, wherein $NR^2$ corresponds to radical 80 of list "N", above, and A of formula (I) denotes one radical selected from list "CyO", above.

Further preferred compounds of formula (I) are those in which B denotes $NHR^2$, wherein $NR^2$ corresponds to radical 81 of list "N", above, and A of formula (I) denotes one radical selected from list "CyO", above.

Further preferred compounds of formula (I) are those in which B denotes $NHR^2$, wherein $NR^2$ corresponds to radical 82 of list "N", above, and A of formula (I) denotes one radical selected from list "CyO", above.

Further preferred compounds of formula (I) are those in which B denotes $NHR^2$, wherein $NR^2$ corresponds to radical 83 of list "N", above, and A of formula (I) denotes one radical selected from list "CyO", above.

Further preferred compounds of formula (I) are those in which B denotes $NHR^2$, wherein $NR^2$ corresponds to radical 84 of list "N", above, and A of formula (I) denotes one radical selected from list "CyO", above.

Further preferred compounds of formula (I) are those in which B denotes $NHR^2$, wherein $NR^2$ corresponds to radical 85 of list "N", above, and A of formula (I) denotes one radical selected from list "CyO", above.

Further preferred compounds of formula (I) are those in which B denotes $NHR^2$, wherein $NR^2$ corresponds to radical 86 of list "N", above, and A of formula (I) denotes one radical selected from list "CyO", above.

Further preferred compounds of formula (I) are those in which B denotes $NHR^2$, wherein $NR^2$ corresponds to radical 87 of list "N", above, and A of formula (I) denotes one radical selected from list "CyO", above.

Further preferred compounds of formula (I) are those in which B denotes $NHR^2$, wherein $NR^2$ corresponds to radical 88 of list "N", above, and A of formula (I) denotes one radical selected from list "CyO", above.

Further preferred compounds of formula (I) are those in which B denotes $NHR^2$, wherein $NR^2$ corresponds to radical 89 of list "N", above, and A of formula (I) denotes one radical selected from list "CyO", above.

Further preferred compounds of formula (I) are those in which B denotes $NHR^2$, wherein $NR^2$ corresponds to radical 90 of list "N", above, and A of formula (I) denotes one radical selected from list "CyO", above.

Further preferred compounds of formula (I) are those in which B denotes $NHR^2$, wherein $NR^2$ corresponds to radical 91 of list "N", above, and A of formula (I) denotes one radical selected from list "CyO", above.

Further preferred compounds of formula (I) are those in which B denotes $NHR^2$, wherein $NR^2$ corresponds to radical 92 of list "N", above, and A of formula (I) denotes one radical selected from list "CyO", above.

Further preferred compounds of formula (I) are those in which B denotes $NHR^2$, wherein $NR^2$ corresponds to radical 93 of list "N", above, and A of formula (I) denotes one radical selected from list "CyO", above.

Further preferred compounds of formula (I) are those in which B denotes $NHR^2$, wherein $NR^2$ corresponds to radical 94 of list "N", above, and A of formula (I) denotes one radical selected from list "CyO", above.

Further preferred compounds of formula (I) are those in which B denotes $NHR^2$, wherein $NR^2$ corresponds to radical 95 of list "N", above, and A of formula (I) denotes one radical selected from list "CyO", above.

Further preferred compounds of formula (I) are those in which B denotes $NHR^2$, wherein $NR^2$ corresponds to radical 96 of list "N", above, and A of formula (I) denotes one radical selected from list "CyO", above.

Further preferred compounds of formula (I) are those in which B denotes $NHR^2$, wherein $NR^2$ corresponds to radical 97 of list "N", above, and A of formula (I) denotes one radical selected from list "CyO", above.

Further preferred compounds of formula (I) are those in which B denotes $NHR^2$, wherein $NR^2$ corresponds to radical 98 of list "N", above, and A of formula (I) denotes one radical selected from list "CyO", above.

Further preferred compounds of formula (I) are those in which B denotes $NHR^2$, wherein $NR^2$ corresponds to radical 99 of list "N", above, and A of formula (I) denotes one radical selected from list "CyO", above.

Further preferred compounds of formula (I) are those in which B denotes $NHR^2$, wherein $NR^2$ corresponds to radical 100 of list "N", above, and A of formula (I) denotes one radical selected from list "CyO", above.

Further preferred compounds of formula (I) are those in which B denotes $NHR^2$, wherein $NR^2$ corresponds to radical 101 of list "N", above, and A of formula (I) denotes one radical selected from list "CyO", above.

Further preferred compounds of formula (I) are those in which B denotes $NHR^2$, wherein $NR^2$ corresponds to radical 102 of list "N", above, and A of formula (I) denotes one radical selected from list "CyO", above.

Further preferred compounds of formula (I) are those in which B denotes $NHR^2$, wherein $NR^2$ corresponds to radical 103 of list "N", above, and A of formula (I) denotes one radical selected from list "CyO", above.

Further preferred compounds of formula (I) are those in which B denotes $NHR^2$, wherein $NR^2$ corresponds to radical 104 of list "N", above, and A of formula (I) denotes one radical selected from list "CyO", above.

Further preferred compounds of formula (I) are those in which B denotes $NHR^2$, wherein $NR^2$ corresponds to radical 105 of list "N", above, and A of formula (I) denotes one radical selected from list "CyO", above.

Further preferred compounds of formula (I) are those in which B denotes $NHR^2$, wherein $NR^2$ corresponds to radical 106 of list "N", above, and A of formula (I) denotes one radical selected from list "CyO", above.

Further preferred compounds of formula (I) are those in which B denotes $NHR^2$, wherein $NR^2$ corresponds to radical 107 of list "N", above, and A of formula (I) denotes one radical selected from list "CyO", above.

Further preferred compounds of formula (I) are those in which B denotes $NHR^2$, wherein $NR^2$ corresponds to radical 108 of list "N", above, and A of formula (I) denotes one radical selected from list "CyO", above.

Further preferred compounds of formula (I) are those in which B denotes $NHR^2$, wherein $NR^2$ corresponds to radical 109 of list "N", above, and A of formula (I) denotes one radical selected from list "CyO", above.

Further preferred compounds of formula (I) are those in which B denotes $NHR^2$, wherein $NR^2$ corresponds to radical 110 of list "N", above, and A of formula (I) denotes one radical selected from list "CyO", above.

Further preferred compounds of formula (I) are those in which B denotes $NHR^2$, wherein $NR^2$ corresponds to radical 111 of list "N", above, and A of formula (I) denotes one radical selected from list "CyO", above.

Further preferred compounds of formula (I) are those in which B denotes $NHR^2$, wherein $NR^2$ corresponds to radical 112 of list "N", above, and A of formula (I) denotes one radical selected from list "CyO", above.

Further preferred compounds of formula (I) are those in which B denotes $NHR^2$, wherein $NR^2$ corresponds to radical 113 of list "N", above, and A of formula (I) denotes one radical selected from list "CyO", above.

Further preferred compounds of formula (I) are those in which B denotes $NHR^2$, wherein $NR^2$ corresponds to radical 114 of list "N", above, and A of formula (I) denotes one radical selected from list "CyO", above.

Further preferred compounds of formula (I) are those in which B denotes $NHR^2$, wherein $NR^2$ corresponds to radical 115 of list "N", above, and A of formula (I) denotes one radical selected from list "CyO", above.

Further preferred compounds of formula (I) are those in which B denotes $NHR^2$, wherein $NR^2$ corresponds to radical 116 of list "N", above, and A of formula (I) denotes one radical selected from list "CyO", above.

Further preferred compounds of formula (I) are those in which B denotes $NHR^2$, wherein $NR^2$ corresponds to radical 117 of list "N", above, and A of formula (I) denotes one radical selected from list "CyO", above.

Further preferred compounds of formula (I) are those in which B denotes $NHR^2$, wherein $NR^2$ corresponds to radical 118 of list "N", above, and A of formula (I) denotes one radical selected from list "CyO", above.

Further preferred compounds of formula (I) are those in which B denotes $NHR^2$, wherein $NR^2$ corresponds to radical 119 of list "N", above, and A of formula (I) denotes one radical selected from list "CyO", above.

Further preferred compounds of formula (I) are those in which B denotes $NHR^2$, wherein $NR^2$ corresponds to radical 120 of list "N", above, and A of formula (I) denotes one radical selected from list "CyO", above.

Further preferred compounds of formula (I) are those in which B denotes $NHR^2$, wherein $NR^2$ corresponds to radical 121 of list "N", above, and A of formula (I) denotes one radical selected from list "CyO", above.

Further preferred compounds of formula (I) are those in which B denotes $NHR^2$, wherein $NR^2$ corresponds to radical 122 of list "N", above, and A of formula (I) denotes one radical selected from list "CyO", above.

Further preferred compounds of formula (I) are those in which B denotes $NHR^2$, wherein $NR^2$ corresponds to radical 123 of list "N", above, and A of formula (I) denotes one radical selected from list "CyO", above.

Further preferred compounds of formula (I) are those in which B denotes $NHR^2$, wherein $NR^2$ corresponds to radical 124 of list "N", above, and A of formula (I) denotes one radical selected from list "CyO", above.

Further preferred compounds of formula (I) are those in which B denotes $NHR^2$, wherein $NR^2$ corresponds to radical 125 of list "N", above, and A of formula (I) denotes one radical selected from list "CyO", above.

Further preferred compounds of formula (I) are those in which B denotes $NHR^2$, wherein $NR^2$ corresponds to radical 126 of list "N", above, and A of formula (I) denotes one radical selected from list "CyO", above.

Further preferred compounds of formula (I) are those in which B denotes $NHR^2$, wherein $NR^2$ corresponds to radical 127 of list "N", above, and A of formula (I) denotes one radical selected from list "CyO", above.

Further preferred compounds of formula (I) are those in which B denotes $NHR^2$, wherein $NR^2$ corresponds to radical 128 of list "N", above, and A of formula (I) denotes one radical selected from list "CyO", above.

Further preferred compounds of formula (I) are those in which B denotes $NHR^2$, wherein $NR^2$ corresponds to radical 129 of list "N", above, and A of formula (I) denotes one radical selected from list "CyO", above.

Further preferred compounds of formula (I) are those in which B denotes $NHR^2$, wherein $NR^2$ corresponds to radical 130 of list "N", above, and A of formula (I) denotes one radical selected from list "CyO", above.

Further preferred compounds of formula (I) are those in which B denotes $NHR^2$, wherein $NR^2$ corresponds to radical 131 of list "N", above, and A of formula (I) denotes one radical selected from list "CyO", above.

Further preferred compounds of formula (I) are those in which B denotes $NHR^2$, wherein $NR^2$ corresponds to radical 132 of list "N", above, and A of formula (I) denotes one radical selected from list "CyO", above.

Further preferred compounds of formula (I) are those in which B denotes $NHR^2$, wherein $NR^2$ corresponds to radical 133 of list "N", above, and A of formula (I) denotes one radical selected from list "CyO", above.

Further preferred compounds of formula (I) are those in which B denotes $NHR^2$, wherein $NR^2$ corresponds to radical 134 of list "N", above, and A of formula (I) denotes one radical selected from list "CyO", above.

Further preferred compounds of formula (I) are those in which B denotes $NHR^2$, wherein $NR^2$ corresponds to radical 135 of list "N", above, and A of formula (I) denotes one radical selected from list "CyO", above.

Further preferred compounds of formula (I) are those in which B denotes $NHR^2$, wherein $NR^2$ corresponds to radical 136 of list "N", above, and A of formula (I) denotes one radical selected from list "CyO", above.

Further preferred compounds of formula (I) are those in which B denotes $NHR^2$, wherein $NR^2$ corresponds to radical 137 of list "N", above, and A of formula (I) denotes one radical selected from list "CyO", above.

Further preferred compounds of formula (I) are those in which B denotes $NHR^2$, wherein $NR^2$ corresponds to radical 138 of list "N", above, and A of formula (I) denotes one radical selected from list "CyO", above.

Further preferred compounds of formula (I) are those in which B denotes $NHR^2$, wherein $NR^2$ corresponds to radical 139 of list "N", above, and A of formula (I) denotes one radical selected from list "CyO", above.

Further preferred compounds of formula (I) are those in which B denotes $NHR^2$, wherein $NR^2$ corresponds to radical 140 of list "N", above, and A of formula (I) denotes one radical selected from list "CyO", above.

Further preferred compounds of formula (I) are those in which B denotes $NHR^2$, wherein $NR^2$ corresponds to radical 141 of list "N", above, and A of formula (I) denotes one radical selected from list "CyO", above.

Further preferred compounds of formula (I) are those in which B denotes $NHR^2$, wherein $NR^2$ corresponds to radical 142 of list "N", above, and A of formula (I) denotes one radical selected from list "CyO", above.

Further preferred compounds of formula (I) are those in which B denotes $NHR^2$, wherein $NR^2$ corresponds to radical 143 of list "N", above, and A of formula (I) denotes one radical selected from list "CyO", above.

Further preferred compounds of formula (I) are those in which B denotes $NHR^2$, wherein $NR^2$ corresponds to radical 144 of list "N", above, and A of formula (I) denotes one radical selected from list "CyO", above.

Further preferred compounds of formula (I) are those in which B denotes $NHR^2$, wherein $NR^2$ corresponds to radical 145 of list "N", above, and A of formula (I) denotes one radical selected from list "CyO", above.

Further preferred compounds of formula (I) are those in which B denotes $NHR^2$, wherein $NR^2$ corresponds to radical 146 of list "N", above, and A of formula (I) denotes one radical selected from list "CyO", above.

Further preferred compounds of formula (I) are those in which B denotes $NHR^2$, wherein $NR^2$ corresponds to radical 147 of list "N", above, and A of formula (I) denotes one radical selected from list "CyO", above.

Further preferred compounds of formula (I) are those in which B denotes $NHR^2$, wherein $NR^2$ corresponds to radical 148 of list "N", above, and A of formula (I) denotes one radical selected from list "CyO", above.

Further preferred compounds of formula (I) are those in which B denotes $NHR^2$, wherein $NR^2$ corresponds to radical 149 of list "N", above, and A of formula (I) denotes one radical selected from list "CyO", above.

Further preferred compounds of formula (I) are those in which B denotes $NHR^2$, wherein $NR^2$ corresponds to radical 150 of list "N", above, and A of formula (I) denotes one radical selected from list "CyO", above.

Further preferred compounds of formula (I) are those in which B denotes $NHR^2$, wherein $NR^2$ corresponds to radical 151 of list "N", above, and A of formula (I) denotes one radical selected from list "CyO", above.

Further preferred compounds of formula (I) are those in which B denotes $NHR^2$, wherein $NR^2$ corresponds to radical 152 of list "N", above, and A of formula (I) denotes one radical selected from list "CyO", above.

Further preferred compounds of formula (I) are those in which B denotes $NHR^2$, wherein $NR^2$ corresponds to radical 153 of list "N", above, and A of formula (I) denotes one radical selected from list "CyO", above.

Further preferred compounds of formula (I) are those in which B denotes $NHR^2$, wherein $NR^2$ corresponds to radical 154 of list "N", above, and A of formula (I) denotes one radical selected from list "CyO", above.

However, in the context of the present invention, and depending on the circumstances, each individual compound of the compounds of formula (Carb-II-R1H), in particular those defined by the CyO-N-code, may for technical or non-technical reasons, as the case may be, in some embodiments be more preferred or less preferred than other compounds of formula (Carb-II-R1H), in particular those defined by the CyO-N-code. Thus, in some cases, compounds of formula (Carb-II-R1H) as defined by the CyO-N-code do not necessarily share the same level of preference.

Several compounds of formula (I), in particular the preferred compounds according to the present invention, are identified and referred to using an arbitrary internal reference-numbering system of the type "BIO", followed by a four-digit number.

In one embodiment, compounds of formula (I), (Carb-I), (Carb-II) and Carb-II-R1H) are those in which X, Y and Z each denote hydrogen (corresponding to CyO-radical AA).

Such cyclohexyl carbamates are derived from unsubstituted cyclohexanols, thus to compounds of formula (I) in which A denotes:

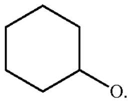

A particularly preferred cyclohexyl carbamate, derived from unsubstituted cyclohexanol is:

BIO1741: Phenyl-carbamic acid cyclohexyl ester (corresponding to CyO-N-code AA35)

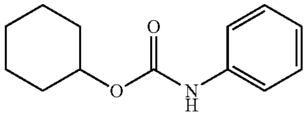 [SMILES: O=C(Nc1ccccc1)OC1CCCCC1]

In our investigations it was found that compounds of formula (I) in which X, Y and Z each denote hydrogen (i.e. those wherein the CyO-radical denotes AA) were less effective regarding the effects to be achieved in the context of the present invention in comparison to compounds of formula (I) derived from mono-, di- or trisubstituted cyclohexanols as described hereinafter. Thus, compounds of formula (I) wherein one, two or all substituents X, Y and Z are not hydrogen, are preferred.

In a preferred embodiment, preferred compounds of formula (I), (Carb-I), (Carb-II) and (Carb-II-R1H), are those in which X denotes C1-C4-alkyl or C2-C4-alkenyl and Y and Z both denote hydrogen.

Such cyclohexyl carbamates are derived from monosubstituted cyclohexanols, thus to compounds of formula (I) in which A denotes

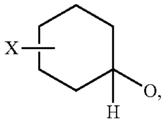

wherein X has the meaning given above.

Preferably, X denotes C1-C4-alkyl, more preferably X denotes methyl, isopropyl or tert.butyl.

In own investigations it was found that compounds of formula (I) in which A denotes

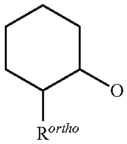

wherein $R^{ortho}$ is methyl were less effective than those where $R^{ortho}$ was C2-C4-alkyl, in particular less active than those compounds of formula (I) where $R^{ortho}$ was iso-propyl or tert.-butyl. Consequently, compounds of formula (I) in which $R^{ortho}$ denotes iso-propyl or tert.-butyl, are preferred in this context.

Most preferably A denotes

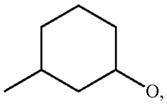
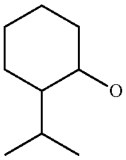
or
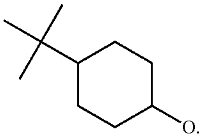

Particularly preferred cyclohexyl carbamates of formula (Carb-II-R1H), derived from monosubstituted cyclohexanols, are the following:

| Reference-number | Chemical Name | Structure | CyO-N-Code |
|---|---|---|---|
| BIO1821 | Butyl-carbamic acid 3-methyl-cyclohexyl ester | 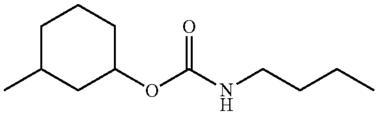 | AC5 |
| BIO1825 | p-Tolyl-carbamic acid 3-methyl-cyclohexyl ester | 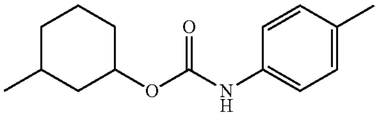 | AC38 |

-continued

| Reference-number | Chemical Name | Structure | CyO-N-Code |
|---|---|---|---|
| BIO1828 | Butyl-carbamic acid 2-methyl-cyclohexyl ester | 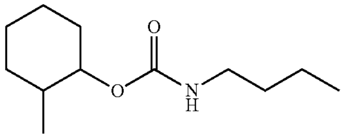 | AB5 |
| BIO1747 | Cyclohexyl-carbamic acid 4-tert-butyl-cyclohexyl ester | 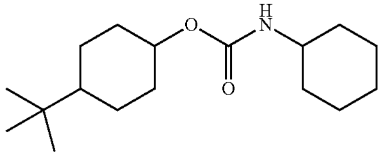 [SMILES: CC(C)(C)C1CCC(OC(=O)NC2CCCCC2)CC1] | AX25 |
| BIO1841 | Butyl-carbamic acid 2-isopropyl-cyclohexyl ester | 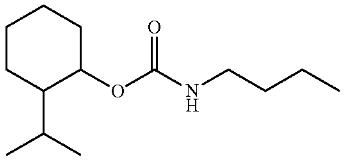 [SMILES: CCCCNC(=O)OC1CCCCC1C(C)C] | AK5 |
| BIO1748 | Benzyl-carbamic acid 2-isopropyl-cyclohexyl ester | 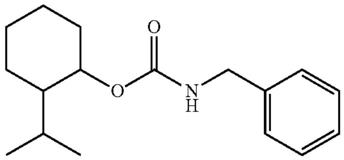 [SMILES: CC(C)C1CCCCC1OC(=O)NCc1ccccc1] | AK45 |
| BIO1824 | p-Tolyl-carbamic acid 2-isopropyl-cyclohexyl ester | 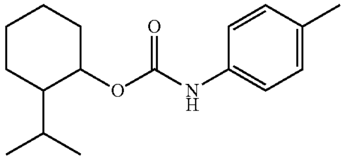 [SMILES: Cc1ccc(NC(=O)OC2CCCCC2C(C)C)cc1] | AK38 |
| BIO1851 | Hexyl-carbamic acid 2-isopropyl-cyclohexyl ester | 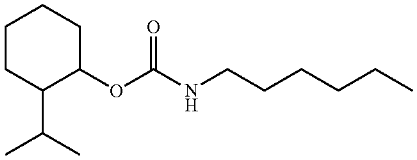 [SMILES: CCCCCCNC(=O)OC1CCCCC1C(C)C] | AK13 |
| BIO1744 | (2-Methoxy-phenyl)-carbamic acid 2-isopropyl-cyclohexyl ester | 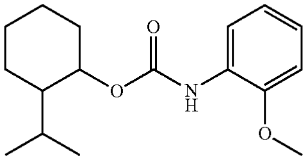 [SMILES: COc1ccccc1NC(=O)OC1CCCCC1C(C)C] | AK73 |
| BIO1552 | Ethyl-carbamic acid 2-isopropyl-cyclohexyl ester | 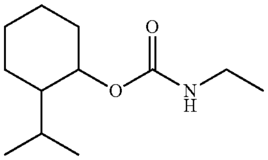 | AK2 |

The (preferred) compounds of formula (I) derived from monosubstituted cyclohexanols, in particular those explicitly listed above, were particularly active regarding the effects to be achieved in the context of the present invention.

In another preferred embodiment, preferred compounds of formula (I), (Carb-I), (Carb-II) and Carb-II-R1H), are those in which X and Y independently of one another denote C1-C4-alkyl or C2-C4-alkenyl and Z denotes hydrogen.

Such cyclohexyl carbamates are derived from disubstituted cyclohexanols, thus to compounds of formula (I) in which A denotes

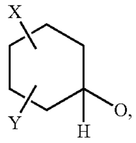

wherein X and Y have the meaning given above.

Preferably, X and Y independently of one another denote C1-C4-alkyl, more preferably methyl, isopropyl or tert.-butyl. In a preferred embodiment, X or Y denotes methyl.

More preferably, X and Y independently of one another denote methyl or isopropyl, most preferably A denotes

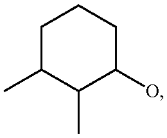,
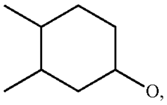,
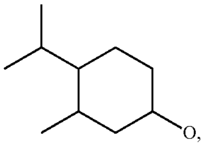,
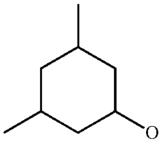
or
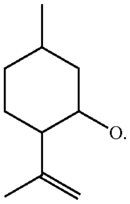.

Particularly preferred cyclohexyl carbamates of formula (Carb-II-R1H), derived from disubstituted cyclohexanols, are the following:

| Reference-number | Chemical Name | Structure | CyO-N-Code |
|---|---|---|---|
| BIO1743 | Cyclohexyl-carbamic acid 3,5-dimethyl-cyclohexyl ester | 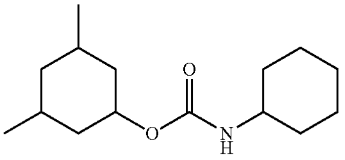 [SMILES: CC1CC(C)CC(OC(=O)NC2CCCCC2)C1] | BH25 |
| BIO1745 | Benzyl-carbamic acid 3,5-dimethyl-cyclohexyl ester | 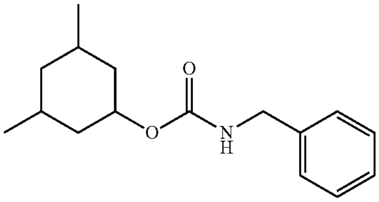 [SMILES: CC1CC(C)CC(OC(=O)NCc2ccccc2)C1] | BH45 |
| BIO1823 | (4-Ethyl-phenyl)-carbamic acid 3,5-dimethyl-cyclohexyl ester | 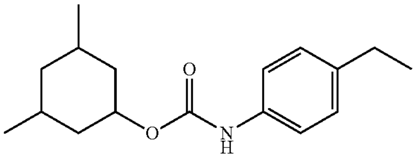 [SMILES: CCc1ccc(NC(=O)OC2CC(C)CC(C)C2)cc1] | BH103 |
| BIO1561 | Ethyl-carbamic acid 3,5-dimethyl-cyclohexyl ester | 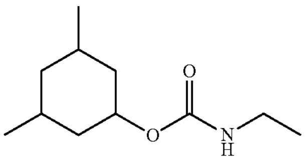 | BH2 |
| BIO1822 | p-Tolyl-carbamic acid 3,5-dimethyl-cyclohexyl ester | 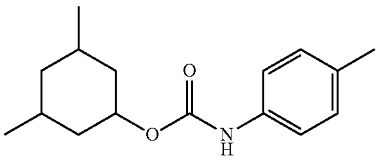 | BH38 |

-continued

| Reference-number | Chemical Name | Structure | CyO-N-Code |
| --- | --- | --- | --- |
| BIO1840 | Butyl-carbamic acid 3,5-dimethyl-cyclohexyl ester | 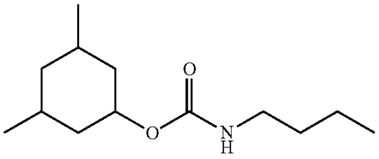 [SMILES: CCCCNC(=O)OC1CC(C)CC(C)C1] | BH5 |
| BIO1685 | Phenyl-carbamic acid 3,5-dimethyl-cyclohexyl ester | 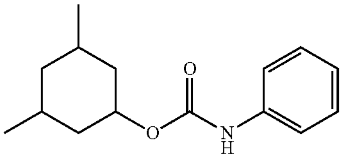 [SMILES: CC1CC(C)CC(OC(=O)Nc2ccccc2)C1] | BH35 |
| BIO1582 | Ethyl-carbamic acid 3,4-dimethyl-cyclohexyl ester | 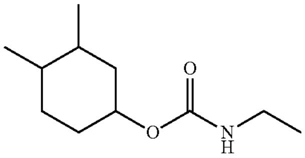 | BD2 |
| BIO1827 | Butyl-carbamic acid 3,4-dimethyl-cyclohexyl ester | 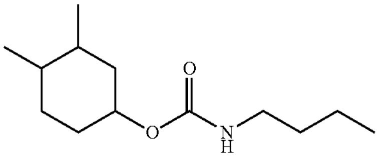 [SMILES: CCCCNC(=O)OC1CCC(C)C(C)C1] | BD5 |
| BIO1845 | sec-Butyl-carbamic acid 2,3-dimethyl-cylcohexyl ester | 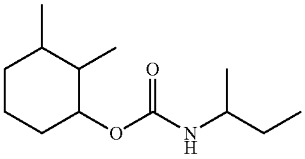 [SMILES: CCC(C)NC(=O)OC1CCCC(C)C1C] | AZ7 |
| BIO1842 | Butyl-carbamic acid 2,3-dimethyl-cyclohexyl ester | 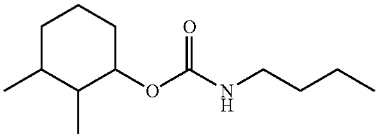 [SMILES: CCCCNC(=O)OC1CCCC(C)C1C] | AZ5 |
| BIO1581 | Ethyl-carbamic acid 2,3-dimethyl-cyclohexyl ester | 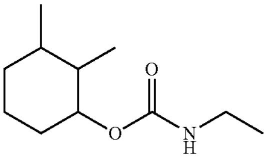 | AZ2 |
| BIO1643 | (2-Hydroxy-phenyl)-carbamic acid 2,3-dimethyl-cyclohexyl ester | 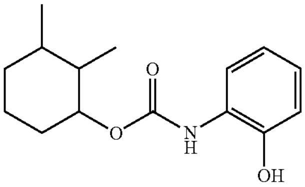 [SMILES: CC1CCCC(OC(=O)Nc2ccccc2O)C1C] | AZ111 |
| BIO1560 | Ethyl-carbamic acid 4-isopropyl-3-methyl-cyclohexyl ester | 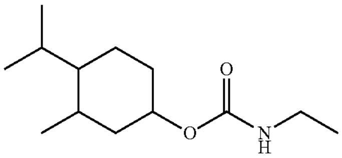 [SMILES: CCNC(=O)OC1CCC(C(C)C)C(C)C1] | DJ2 |

-continued

| Reference-number | Chemical Name | Structure | CyO-N-Code |
|---|---|---|---|
| BIO1615 | Butyl-carbamic acid 2-isopropenyl-5-methyl-cyclohexyl ester | 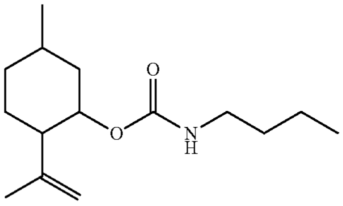 [SMILES: C=C(C)C1CCC(C)CC1OC(=O)NCCCC] | PK5 |
| BIO1551 | Ethyl-carbamic acid 2-isopropenyl-5-methyl-cyclohexyl ester | 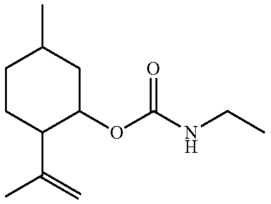 | PK2 |

The (preferred) compounds of formula (I) derived from disubstituted cyclohexanols, in particular those explicitly listed above, were particularly active regarding the effects to be achieved in the context of the present invention.

In another preferred embodiment, preferred compounds of formula (I), (Carb-I), (Carb-II) and Carb-II-R1H) are those in which X, Y and Z independently of one another denote C1-C4-alkyl or C2-C4-alkenyl.

Such cyclohexyl carbamates are derived from trisubstituted cyclohexanols, thus to compounds of formula (I) in which A denotes

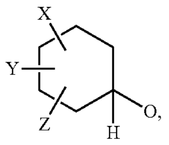

wherein X, Y and Z have the meaning given above.

Preferably, X, Y and Z independently of one another denote C1-C4-alkyl, more preferably methyl, isopropyl or tert.-butyl. In a preferred embodiment, at least one substituent of X, Y or Z denotes methyl.

More preferably, X, Y and Z independently of one another denote methyl or isopropyl, most preferably X, Y and Z each denote methyl, in particular A denotes

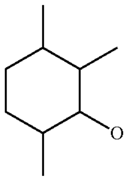

or

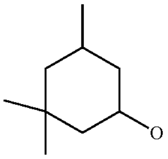

.

Also preferred cyclohexyl carbamates are derived from trisubstituted cyclohexanols are those wherein X denotes methyl and Y and Z together form a radical (a bridge) with 3 carbon atoms.

Among the compounds of formula (I) derived from bicyclic cyclohexanols, it was found that those wherein A denotes

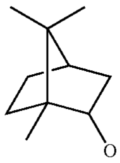

(i.e. borneyl or isoborneyl) were particularly active, in particular those of formula (Carb-II-R1H).

Particularly preferred cyclohexyl carbamates of formula (Carb-II-R1H), derived from trisubstituted cyclohexanols, are the following:

| Reference-number | Chemical Name | Structure | CyO-N-Code |
|---|---|---|---|
| BIO1701 | (2-Methoxy-phenyl)-carbamic acid 2,3,6-trimethyl-cyclohexyl ester | 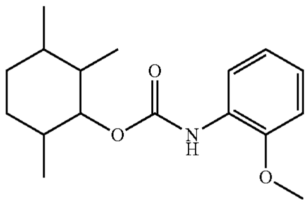 [SMILES: COc1ccccc1NC(=O)OC1C(C)CCC(C)C1C] | BM73 |

-continued

| Reference-number | Chemical Name | Structure | CyO-N-Code |
|---|---|---|---|
| BIO1617 | Butyl-carbamic acid 2,3,6-trimethyl-cyclohexyl ester | 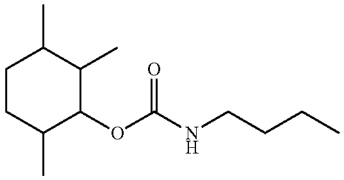 [SMILES: CCCCNC(=O)OC1C(C)CCC(C)C1C] | BM5 |
| BIO1850 | Hexyl-carbamic acid 3,3,5-trimethyl-cyclohexyl ester | 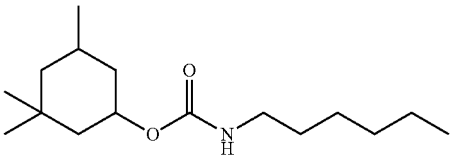 [SMILES: CCCCCCNC(=O)OC1CC(C)CC(C)(C)C1] | BU13 |
| BIO1703 | (2-Methoxy-phenyl)-carbamic acid 3,3,5-trimethyl-cyclohexyl ester | 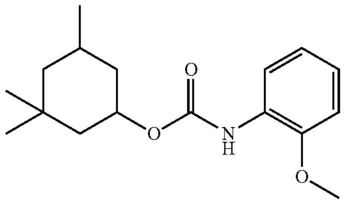 | BU73 |
| BIO1616 | Butyl-carbamic acid 3,3,5-trimethyl-cyclohexyl ester | 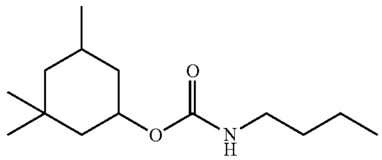 [SMILES: CCCCNC(=O)OC1CC(C)CC(C)(C)C1] | BU5 |
| BIO1844 | sec-Butyl-carbamic acid 3,3,5-trimethyl-cyclohexyl ester | 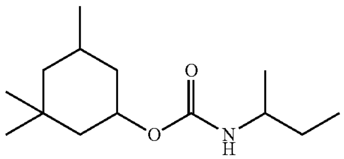 [SMILES: CCC(C)NC(=O)OC1CC(C)CC(C)(C)C1] | BU7 |
| BIO1572 | Ethyl-carbamic acid 3,3,5-trimethyl-cyclohexyl ester | 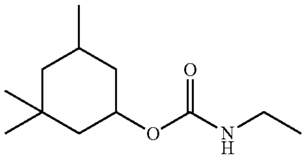 | BU2 |
| BIO1573 | Ethyl-carbamic acid 1,7,7-trimethyl-bicyclo[2.2.1]hept-2-yl ester | 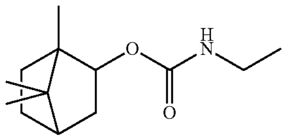 [SMILES: CCNC(=O)OC1CC2CCC1(C)C2(C)C] | TQ2 |

The (preferred) compounds of formula (I) derived from trisubstituted cyclohexanols, in particular those explicitly listed above, were particularly active regarding the effects to be achieved in the context of the present invention.

The following compounds of formula (Carb-II-R1H) are particularly preferred since these were among the most active and effective compounds tested in all three Routes (i), (ii) and (iii):

BIO1617, BIO1851, BIO1823, BIO1581, BIO1841, BIO1745, BIO1844, BIO1748, BIO1845, BIO1616, BIO1743, BIO1747, BIO1842, BIO1840, BIO1615, BIO1573.

The compounds of formula (I) of the present invention may generally be obtained by procedures well-known in chemical synthesis. For example, reaction of

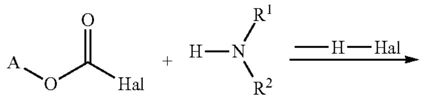

(I) or

-continued

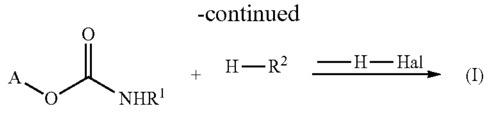

wherein

A, $R^1$ and $R^2$ denote a (preferred) radical as defined hereinabove, preferably $R^1$ denotes H, and Hal denotes a halide, preferably chloride or bromide.

In order to facilitate the dehydrohalogenation step and the formation of a compound of formula (I) it is preferred to carry out said reaction in the presence of a base, preferably a tertiary amine.

The preferred compounds of formula (I) wherein $R^1$ denotes H may preferably be obtained by reacting a cyclohexanol of formula A-H with a corresponding isocyanate O═C═N—$R^2$, as illustrated in the following reaction scheme:

$$A\text{-}H + O{=}C{=}N{-}R^2 \rightarrow \quad (I)$$

wherein A and $R^2$ denote a (preferred) radical as defined hereinabove. The reaction of the isocyanate and the cyclohexanol of formula A-H may be conducted in the absence (see example 1.1.1, below) or the presence of an inert solvent (see example 1.3.2, below).

The present invention also relates to a cosmetic or pharmaceutical, preferably topical, composition for preventing, treating or reducing cellulite, comprising (a) an effective amount of one, two or more compounds, preferably of the preferred compounds, of formula (I) as defined herein and/or a cosmetically or pharmaceutically acceptable salt thereof, to reduce the lipid quantity contained in subcutaneous fat tissue, and/or to stimulate the lipoylsis in adipocytes, and/or to inhibit the differentiation of preadipocytes, and/or to inhibit the lipogenesis in adipocytes, and one or more compounds selected from the following groups (b) and/or (c):

(b) one or more lipolysis stimulants, preferably selected from (b-i) the group of phosphodiesterase inhibitors, and/or (b-ii) the group of agonists of beta-adrenergic receptors, and/or (c) one or more stimulators of the transport or oxidation of free fatty acids, preferably selected from (c-i) the group of promoters of the transport of free fatty acids in the mitochondria, preferably coenzyme A, and/or (c-ii) the group of stimulators of beta-oxidation, preferably L-carnitine.

In the context of the present invention an effective amount of compounds of formula (I), preferably of the preferred compounds of formula (I), relates to a total amount of one, two or more compounds, preferably of the preferred compounds, of formula (I) sufficient to exhibit an activity in the above described Routes (i) and/or (ii) and/or (iii), i.e. to influence one or more of said Routes in the desired way in the sense of the present invention.

Preferably, an effective amount of (the preferred) compounds of formula (I) relates to a total amount of one, two or more compounds, preferably of the preferred compounds, of formula (I) sufficient to stimulate lipolysis (Route (iii)), more preferably exhibit an activity in at least two, preferably all three above mentioned Routes (i), (ii) and (iii).

A composition (preparation), preferably a topical composition, according to the present invention preferably contains one or more compounds of formula (I) (including all stereoisomers, enantiomers, diastereomers, cis/trans-isomers and epimers, without taking into account possible counterions) in a total quantity of 0.001-10% by weight, preferably 0.005-5% by weight and particularly preferably 0.01-2% by weight and most preferably 0.05-1% by weight, in each case based on the total weight of the preparation (composition).

The compounds of formula (I) can easily be incorporated in these concentrations in common cosmetic or dermatological formulations such as pump sprays, aerosol sprays, creams, ointments, tinctures, lotions and the like. The (preferred) compounds of formula (I) also stimulate lipolysis (Route (iii)). Nevertheless it is also possible and in many cases advantageous to combine the compounds of formula (I) with further active ingredients to enhance lipolysis stimulation (Route (iii)).

The invention in one aspect of the present invention relates to (improved), preferably cosmetic, preparations (compositions) containing:

(a) one or more compounds of formula (I), and (b) one or more lipolysis stimulants.

Lipolysis stimulants are active ingredients which stimulate lipolysis (Route (iii)) and are preferably selected from the group (b-i) of inhibitors of phosphodiesterase, and/or the group (b-ii) of agonists of beta-adrenergic receptors, Preferably, the lipolysis stimulant is present in a quantity sufficient to stimulate lipolysis.

The invention in another aspect of the present invention relates to (improved) cosmetic preparations (compositions) containing:

(a) one or more compounds of formula (I), and (c) one or more stimulators of the transport or oxidation of free fatty acids.

Stimulators of the transport or oxidation of free fatty acids are preferably selected from the group (c-i) of promoters of the transport of free fatty acids in the mitochondria, preferably coenzyme A, and/or the group (c-ii) of stimulators of beta-oxidation, preferably L-carnitine.

Preferably, the one or more stimulators of the transport or oxidation of free fatty acids are present in a quantity sufficient to stimulate the transport or oxidation of free fatty acids.

An advantageous preparation according to the invention additionally contains anti-cellulite active ingredients from group (b-i) of inhibitors of phosphodiesterase selected from the group of xanthines, preferably selected from the group of optionally substituted 3,7- or 3,9-dihydro-1H-purin-2,6-diones of the formula (Xa):

(Xa)

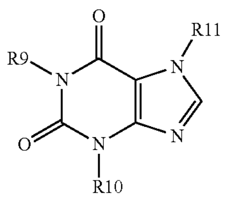

wherein R9, R10 and R11, independently of one another, signify hydrogen or methyl.

The xanthines, in particular those of formula (Xa), may preferably be used as pure materials or else in the form of plant extracts.

The methyl xanthines are preferably caffeine (R9=R10=R11=$CH_3$), theobromine (R9=H, R10=R11=$CH_3$) and theophylline (R9=R10=$CH_3$, R11=H); the most preferred xanthine in the sense of the present invention is caffeine. Also preferred is the theophylline derivative aminophylline.

Particularly preferably, a cosmetic, preferably topical preparation according to the invention contains one or more compounds of formula (Xa), in turn preferred here caffeine, preferably in a total quantity of 0.005-10% by weight, preferably 0.05-5% by weight, particularly preferably 0.5-2.5% by weight, in each case based on the total weight of the preparation, counterions of the compounds of formula (Xa) not being included.

Preferred weight ratios of the total quantity of the compound of formula (I) to the total quantity of xanthines of formula (Xa), caffeine being preferred here, in the preparations according to the invention are preferably from 20:1 to 1:500, more preferably from 1:1 to 1:50, also without taking into account possible counterions.

Also preferred preparations contain combinations of the compound of formula (I) with an agonist of beta-adrenergic receptors of adipocytes. Preferred agonists of beta-adrenergic receptors are β-phenylethylamines of formula (PhEA):

(PhEA)

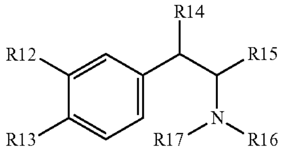

wherein

R12 and R13, independently of one another, signify hydrogen, hydroxy or methoxy, R14 signifies hydrogen, hydroxy or methyl, R15 signifies hydrogen or methyl R16 and R17, independently of one another, signify hydrogen or $C_1$-$C_4$-alkyl.

The β-phenylethylamines of formula (PhEA) can preferably be used as pure substances, in the form of their respective hydrochlorides or in the form of plant extracts.

Preferred agonists of beta-adrenergic receptors are adrenaline, noradrenaline, metanephrine, macromerine, normacromerine, hordenine, N-methyltyramine, dopamine, octopamine, tyramine, 2-phenylethylamine, phenylethanolamine, epinine (N-methyldopamine), synephrine, ephedrine, pseudoephedrine, norephedrine and isoprenaline.

Some of these compounds had already been investigated in the literature for their activity with regard to the beta-3-adrenergic receptor in human fat cells and mammals (Naunyn-Schmiedeberg's Archives of Pharmacology 1999, 359, 310-321).

Compounds of formula (PhEA) in which R17=H and R16 signifies hydrogen or $C_1$-$C_4$-alkyl, preferably hydrogen, methyl or isopropyl are preferred. Further preferred are compounds of formula (PhEA), in which additionally R15=H.

In a further preferred configuration, the agonists of beta-adrenergic receptors are those compounds in which R12 and R17=H.

Particularly preferred agonists of beta-adrenergic receptors correspond to the formula (PhEA-i), and in turn preferred here are tyramine, N-methyltyramine, octopamine and synephrine.

(PhEA-i)

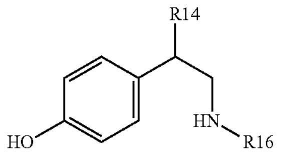

wherein the residues R14 and R16 have the aforementioned (preferred) significance.

The most preferred agonist of a beta-adrenergic receptor is synephrine (R14=OH, R16=$CH_3$ in formula (PhEA-i)), preferably racemic or enantiomer-pure, in this case in turn preferred is the (−)-form. Likewise particularly preferred are synephrine-containing extracts, such as, for example, orange blossom extract.

A cosmetic, preferably topical preparation (composition) according to the invention particularly preferably contains an agonist of a beta-adrenergic receptor, in this case preferably synephrine, preferably in a total quantity of 0.0001-0.10% by weight, preferably 0.001-0.05% by weight, more preferably 0.002-0.02% by weight, in each case based on the total weight of the preparation, the counterion of the agonist not being included in the case of salts.

The weight ratios of the total quantity of the compound of formula (I) to the total quantity of agonists of a beta-adrenergic receptor, in particular to synephrine, in preparations according to the invention are preferably selected from 1000:1 to 1:5, more preferably from 500:1 to 1:1.

As the occurrence of cellulite, in addition to an increased storage of fat in the fat tissue, is generally also accompanied by a breakdown of the connective tissue, preferred cosmetic preparations according to the invention containing one or more compounds of formula (I) preferably also contain active ingredients which prevent a breakdown of the connective tissue. Such preparations show improved efficacy in the prophylaxis and cosmetic treatment of cellulite.

Active ingredients are advantageous here which inhibit matrix-metallo-proteinases (MMPs). Such preparations are particularly effective in the prophylaxis and cosmetic treatment of cellulite. These enzymes are in a position to break down macromolecules of the extra-cellular matrix (ECM)/of the connective tissue, also including the collagens, proteolytically. In particular the matrix-metallo-proteinase-1 (MMP-1), matrix-metalloproteinase-2 (MMP-2) and matrix-metallo-proteinase-9 (MMP-9) are responsible for the breakdown of the connective tissue of the skin. An inhibition of MMPs is possible, for example, by the addition of ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran. An addition of peptides, which inhibit MMPs, to preparations according to the invention, is also advantageous to inhibit MMPs. Proteins or glycoproteins from soya and hydrolysed proteins from rice, pea or lupine also inhibit MMPs and are therefore a suitable addition. A combination with a plant extract, which inhibits MMPs is also advantageous. To be mentioned here by way of example is an extract from shitake mushrooms. The combination with extracts from the leaves of the Rosaceae family, sub-family Rosoideae, is also advantageous. Quite particularly advantageous is the use of blackberry leaf extract, in particular as described in WO 2005/123101 A1.

MMP inhibitors to be preferably used in combination in the scope of the present invention are retinyl palmitate, propyl gallate, precocenes, 6-hydroxy-7-methoxy-2,2-dimethyl-1 (2H)benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilonamino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and numerous further plant extracts, which are listed in WO 02/069992 (see table 1-12 there).

In order to counteract the breakdown of the connective tissue, the combination of active ingredients, which encourage the formation of collagen in the tissue (collagen synthesis stimulators, collagen stimulants), is furthermore advantageous in preferred cosmetic preparations according to the invention containing one or more compounds of formula (I). Such preparations are particularly effective in the prophylaxis and cosmetic treatment of cellulite. Individual substances frequently used to increase collagen synthesis are, for example, ingredients such as ascorbic acid and their derivatives, retinol and derivatives of retinol or plant extracts such as, for example, extracts of aloe and *centella* species. Moreover peptidic materials and their derivatives, such as, for example, carnitine, carnosine, creatine, matrikine peptides (e.g. lysyl-threonyl-threonyl-lysyl-serine) and further peptidic structures such as palmitoylated pentapeptides (for example matrixyl/company Sederma) or the oligopeptide with the trade name Vincipeptide (company Vincience/France) are also included in the frequently used active ingredients increasing collagen synthesis. Furthermore, compounds such as asiatic acid, madecassic acid, madecassoside, asiaticoside, extracts of *Centella asiatica*, niacinamide, astaxanthine, glucans, for example from yeast and oats, soya extracts and soya isoflavones such as genistein and daidzein, rutin, chrysin, morin, betel nut alkaloids, forskolin, betulinic acid, extracts of *Plantago* species, TGF-beta, extracts from *Ginkgo biloba*, glutamine and glycolic acid are also used as collagen synthesis stimulators. Particularly preferred here is the addition of a combination of aloe vera extract, raspberry extract and magnesium ascorbyl phosphate.

Thus, further preferred cosmetic or pharmaceutical, preferably topical, preparations according to the invention containing one or more compounds of formula (I) further additionally comprise one or more matrix-metalloproteinase inhibitors, and/or one or more collagen synthesis stimulators.

Other preferred cosmetic or pharmaceutical, preferably topical, preparations according to the invention containing one or more compounds of formula (I) further additionally comprise one or more agents which stimulate and/or depolarise C nerve fibres, preferably selected from the group consisting of capsaicin, vanillyl-nonylamid and derivatives thereof or extracts containing one or more of these substances like extracts obtainable from various species of the genus *Capsicum* (such as *Capsicum annum*), and/or one or more agents which stimulate the microcirculation or draining, preferably selected from the group consisting of butcher's broom extract or its active component ruscogenin, horse chestnut extract or its active component escin, ivy extract and/or pineapple extract.

Such preparations are particularly effective in the prophylaxis and cosmetic treatment of cellulite.

The present invention further relates to novel compounds of formula (Carb-II-R1H) or a cosmetically acceptable salt thereof (Carb-II-R1H)

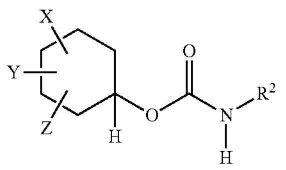

wherein $R^2$ denotes a radical having 1 to 14 carbon atoms, wherein $R^2$ consists of carbon, hydrogen and optionally oxygen and optionally silicon, preferably $R^2$ consists of carbon, hydrogen and optionally oxygen, X, Y and Z independently of one another denote hydrogen, C1-C4-alkyl or C2-C4-alkenyl, wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms, wherein the compound of formula (Carb-II-R1H) contains a maximum number of 24 carbon atoms and has a molecular weight of at most 500 g/mol, preferably a molecular weight of at most 450 g/mol, with the proviso that the following compounds of formula (Carb-II-R1H) are excluded:

(i) menthyl-carbamates of formula (M-H) given above, wherein $R^2$ has the meaning as in (Carb-II-R1H), (ii) compounds of formula (Carb-II-R1H) in which $R^2$ is phenyl or naphthyl, (iii) compounds of formula (Carb-II-R1H) in which X, Y, and Z each denote H, (iv) compounds of formula (Carb-II-R1H) wherein two of the radicals X, Y and Z are covalently bonded to one another under formation of a bicyclic ring system and wherein $R^2$ contains one or both of the following groups: —COOH and/or =CH2, and (v) compounds known from the prior art of the formulae given above.

For the sake of clarity, it is noted that menthyl-carbamates of formula (M-H) include all stereoisomeric forms of the carbamates of formula (M-H), i.e. the menthyl-, neomenthyl-, isomenthyl- and neoisomenthyl-carbamates, including their respective enantiomeric forms.

Preferably, the compounds of formula (I), in particular the novel compounds of formula (Carb-II-R1H), are anti-cellulite actives (in accordance with the definition and preferred embodiments given above).

Preferably, from the novel compounds the following compounds are excluded:

compounds of formula (Carb-II-R1H) in which X, Y and Z each denote hydrogen, compounds of formula (Carb-II-R1H) in which $R^2$ is phenyl, 3-Me-phenyl, naphthyl, biphenyl, p-hydroxyphenyl, p-carboxyphenyl, methyl, and compounds of formula (Carb-II-R1H) in which $R^2$ contains one, several or all of the following groups:

—COOH in alpha-position of N, $=CH_2$, carbon-carbon triple bond,

—COOR in alpha- or beta-position of N, wherein R is a C1-C4-alkyl-radical,

—O(CO)-Ph in alpha-position of N.

Preferred novel anti-cellulite compounds or a cosmetically acceptable salt thereof exhibit an anti-cellulite activity in at least two of the following Routes, preferably exhibiting an activity in Route (iii), more preferably exhibiting an activity in all three of the following Routes Route (i) —inhibition of the differentiation of preadipocytes, Route (ii) —inhibition of the lipogenesis in adipocytes, Route (iii) —stimulation of lipoylsis in adipocytes.

The (particularly) preferred compounds of formula (I) of the present invention are preferably used in the preferred compositions indicated hereinbefore or hereinafter.

The (particularly) preferred aspects and embodiments mentioned hereinbefore or hereinafter relating to compounds of formula (I) or compositions (preparations) comprising one or more compounds of formula (I) according to the present invention also apply to (particularly) preferred aspects and embodiments, uses and methods in accordance with the present invention.

The present invention further relates to a method for the cosmetic (i) prevention, treatment or reduction of cellulite, and/or (ii)

reduction of the lipid quantity contained in subcutaneous fat tissue, and/or stimulation of lipoylsis in adipocytes, and/or inhibition of the differentiation of preadipocytes, and/or inhibition of the lipogenesis in adipocytes, comprising the following step:

application, preferably topical application, of a cosmetically effective amount of a compound of formula (I) or a cosmetically acceptable salt of a compound of formula (I) or a mixture containing two or more of these compounds or the salts thereof as defined herein or of a cosmetic composition as defined herein.

Preferably, said method comprises the step of topical application onto the skin, in particular on the thighs (in particular the outer side and the back of the thighs) and/or the buttocks, of a human, preferably a woman.

A further aspect of the present invention is the use of a compound of formula (I) or a pharmaceutically acceptable salt of a compound of formula (I) or a mixture containing two or more of these compounds or the salts thereof as defined herein for the preparation a pharmaceutical, preferably topical, composition for prevention, treatment or reduction of cellulite.

The present invention further relates to a compound of formula (I) or a pharmaceutically acceptable salt of a compound of formula (I) or a mixture containing two or more of these compounds or the salts thereof as defined herein as a drug, in particular (i) as active for preventing, treating or reducing cellulite, and/or (ii)

for reduction of the lipid quantity contained in subcutaneous fat tissue, and/or for stimulation of lipoylsis in adipocytes, and/or for inhibition of the differentiation of preadipocytes, and/or for inhibition of the lipogenesis in adipocytes.

The present invention further relates to a pharmaceutical composition comprising a pharmaceutically active amount of one or more compounds of formula (I) as defined herein, preferably for preventing, treating or reducing cellulite.

Further, the present invention also relates to a method of treatment of cellulite, comprising the following step:

application, preferably topical application, of a pharmaceutically effective amount of a compound of formula (I) or a pharmaceutically acceptable salt of a compound of formula (I) or a mixture containing two or more of these compounds or the salts thereof as defined herein or of a pharmaceutical composition as defined herein.

Substances and auxiliaries which may additionally contain a preparation according to the invention containing one or more compounds of formula (I) are, for example:

preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, further anti-cellulite agents, in particular those described in WO 2007/077541, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, reoiling agents, abrading agents, skin-soothing agents, skin-cleansing agents, skin care agents, skin-healing agents, skin-protecting agents, skin-softening agents, skinsmoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

In a preferred embodiment, a preparation according to the present invention comprises one or more compounds of formula (I) and one or more hair growth modulating actives, in particular one or more agents to stimulate hair growth.

Preferred agents to stimulate hair growth are selected from the group consisting of pyrimidine derivatives, in particular 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids, in particular caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters, in particular tocopheryl nicotinate, benzyl nicotinate and C1-C6 alkyl nicotinate, proteins, in particular the tripeptide Lys-Pro-Val, diphencypren, hormones, finasteride, dutasteride, flutamide, bicalutamide, pregnane derivatives, progesterone and its derivatives, cyproterone acetate, spironolactone and other diuretics, calcineurin inhibitors, in particular FK506 (Tacrolimus, Fujimycin) and its derivatives, Cyclosporin A and derivatives thereof, zinc and zinc salts, polyphenols, procyanidins, proanthocyanidins, phytosterols, in particular betasitosterol, biotin, eugenol, (±)-beta-citronellol, panthenol, glycogen, in particular from mussels, hydrolysates from rice, hydrolysates from wheat, and extracts from microorganisms, algae, microalgae or plants and plant parts, in particular of the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis*, licorice, grape, apple, barley and hops.

In another preferred embodiment, a preparation according to the present invention comprises one or more compounds of formula (I) and one or more agents to inhibit hair growth.

Preferred agents to inhibit hair growth are selected from the group consisting of activin, activin derivatives or activin agonists, ornithine decarboxylase inhibitors, in particular alpha-difluoromethylomithine or pentacyclic triterpenes, in particular ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, and extracts from microorganisms, algae, microalgae or plants and plant parts, in particular of the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* and *Gymnema sylvestre.*

Also advantageous are preparations according to the invention which are administered orally, for example in the form of tablets (for example film tablets), coated tablets, capsules (for example gelatin capsules), granulates, juices, solutions emulsions, micro emulsions, sprays or products which can be consumed orally in another form, or in the form of food, which, because of the compound(s) contained therein of formula (I) bring about “beauty from inside”.

Further preferred osmolytes, which may be a component of a preparation according to the invention, are diglycerol phosphate or ectoin.

Preferred cosmetics carrier materials, which may be a component of a preparation according to the invention, are solid or liquid at 25° C. and 1013 mbar (including highly viscous substances).

Preferred liquid carrier substances, which may be a component of a preparation according to the invention are selected from the group consisting of glycerol, 1,2-propylene glycol, 1,2-butylene glycol, 1,3-butylene glycol, 1,2-pentanediol, 1,2-hexanediol, 1,2-octanediol, 1,2-decanediol, ethanol, water and mixtures of two or more of said liquid carrier materials with water. Optionally, these preparations according to the invention may be produced using preservatives, solubilizers or antioxidants.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

Furthermore, the preparations according to the invention may be present in encapsulated form, these preferably being encapsulated with a solid covering material, which is preferably selected from starches, degraded or chemically or physically modified starches (in particular dextrins and maltodexterins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0 389 700, U.S. Pat. No. 4,251,195, U.S. Pat. No. 6,214,376, WO 03/055587 or WO 2004/050069.

Important areas of application for the preparations according to the invention are cosmetic, in particular dermatological preparations, which are composed as conventional (apart from the compound(s) of formula (I)) and are used for cosmetic, in particular dermatological light protection, for treatment, care and cleaning of the skin and/or hair or as a make-up product in decorative cosmetics. Accordingly, preparations of this type, depending on their structure, can be used, for example, as day protection cream, day or night cream, eye cream, sun protection or after-sun lotion, nourishing cream, a care mask, gel pads, facial tonic, moist care and cleaning tissues, cleaning milk, cleaning soap, foam or shower bath, deodorant, antiperspirant, hair shampoo, hair care agent, hair conditioner, hair colorant, hair styling agent and in this case preferably be present as an emulsion, lotion, milk, fluid, cream, hydro dispersion gel, balm, spray, alcoholic or aqueous/alcoholic solution, foam, powder, liquid soap, piece of soap, shampoo, roll-on, stick or make-up. In hair treatment agents, the use is preferably directed at the base of the hair or the scalp.

The one or more substances with a physiological cooling effect (cooling agents), which can be used in combination with one or more compounds of formula (I) according to the invention, are preferably selected here from the following list: menthol and menthol derivatives (for example L-menthol, D-menthol, racemic menthol, isomenthol, neoisomenthol, neomenthol) menthylethers (for example (1-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycmethylester [W55], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic acid-N-(alkoxyalkyl) amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (1-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl) ethyl)-3-p-menthanecarboxamide or related compounds), oxamates (preferably those described in EP 2 033 688 A2).

The or the plurality of substances with a physiological cooling effect, which can be used in combination with one or more compounds of formula (I) according to the invention, are in particular preferably substances, which at least substantially cause a physiological cooling effect. Such preferred substances are: menthylethers (for example (1-menthoxy)-1,2-propandiol, (1-menthoxy)-2-methyl-1,2-propandiol), polar menthylesters (for example menthyllacetates, L-menthyl-L-lactate, L-menthyl-O-lactate, menthyl-(2-methoxy) acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate), the semi-esters of menthols with a dicarboxylic acid or derivates thereof (for example mono-menthylsuccinate, mono-menthylglutarate, mono-menthylmalonate, O-menthyl succinic acid ester-N,N-(dimethyl)amide, O-menthyl succinic acid esteramide), not according to the invention, menthane carboxylic acid amides (for example menthane carboxylic acid-N-ethylamide [W53], (menthanecarbonyl)glycmethylester [W55], menthane carboxylic acid-N-(4-cyanophenyl)amide, menthane carboxylic acid-N-(alkoxyalkyl)amides), menthone derivatives (for example L-menthone glycerol ketal), 2,3-dimethyl-2-(2-propyl)-butyric acid derivates (for example 2,3-dimethyl-2-(2-propyl)-butyric acid-N-methylamide), pyrrolidone derivatives of cycloalkyldione derivatives (for example 3-methyl-2(1-pyrrolidinyl)-2-cyclopentene-1-one) or tetrahydropyrimidine-2-ones (for example iciline or related compounds, which are described in WO 2004/026840).

The total quantity of substances having a physiological cooling effect (one or more compounds) in the preparations according to the invention preferably is in the range of from 0.05-5% by weight, more preferably in the range of from 0.1-3% by weight, in particular in the range of from 0.25-1.5% by weight, in each case based on the total weight of the preparation.

Components which cause a hot, sharp, tingly or prickly feeling on the skin or on the mucous membranes, in particular flavours with a heat-producing effect and/or sharp tasting compounds (sharp substances) which may, apart from one or more compounds of formula (I), be a component of a preparation according to the invention, are mentioned in WO 2005/123101.

Further, combinations with compounds which reduce the hypersensitivity of skin nerves based on their action as TRPV1 antagonists, e.g. trans-4-tert-butyl cyclohexanol (as described in WO 2009/087242), or indirect modulators of TRPV1 by an activation of the μ-receptor, e.g. acetyl tetrapeptide-15, are preferred.

For use in the conventional manner for cosmetics and pharmaceuticals, the compounds of formula (I) are applied to the skin and/or the hair in an adequate quantity. Particular advantages are offered here by cosmetic and dermatological preparations which contain one or more compounds of formula (I) and additionally act as a sun protection means. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

Preparations according to the invention in the cosmetics and pharmaceuticals area, which contain one or more compounds of formula (I), are particularly advantageously combined with substances which absorb or reflect UV radiation, especially for cosmetic or skin-protecting purposes (in other words not for oral hygiene purposes), the total quantity of the UV filter substances being from 0.01% by weight to 40% by weight, preferably 0.1% to 10% by weight, in particular 1.0 to 5.0% by weight, in each case based on the total weight of the preparations, in order to provide cosmetic preparations, which protect the hair or the skin from ultraviolet radiation. These preparations advantageously contain at least one UVA filter and/or at least one UVB filter and/or at least one inorganic pigment, so a light protection factor (sun protection factor, SPF) of 2 or higher (preferably of 5 or higher) is achieved. These preparations according to the invention may in this case be present in various forms such as, for example, are conventionally used for sun protection preparations. They may thus be, for example, a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

Advantageous UV filters and inorganic light protection pigments are mentioned in WO 2005/123101. UV absorbers particularly suitable for combination are also mentioned in WO 2005/123101.

Advantageous inorganic light protection pigments are finely dispersed metal oxides and metal salts which are also mentioned in WO 2005/123101. The total quantity of inorganic pigments, in particular hydrophobic inorganic micropigments in the finished cosmetic preparation according to the present invention is advantageously from 0.1 to 30% by weight, preferably 0.5 to 10.0, in each case based on the total weight of the preparation.

A combination with (metal)-chelating agents may also be advantageous in some preparations. (Metal)-chelating agents to be preferably used are the compounds mentioned in WO 2005/123101.

Furthermore, it is advantageous to combine compounds of formula (I) with active ingredients which penetrate into the skin and protect the skin cells from inside against sun light-induced damage such as skin aging, skin inflammation and skin cancer. Respective ingredients, so called aryl hydrocarbon receptor antagonists, are described in WO 2007/128723. Preferred is 2-benzylidene-5,6-dimethoxy-3,3-dimethylindan-1-one.

Cosmetic preparations preferred according to the invention can also contain anti-inflammatory and/or redness and/or itch ameliorating active ingredients. The compounds mentioned in WO 2005/123101 are advantageously used as anti-inflammatory or redness and/or itch ameliorating active ingredients.

The total quantity of anti-irritants (one or more compounds) in the preparations according to the invention preferably is in the range of from 0.0001-20% by weight, more preferably in the range of from 0.0001-10% by weight, in particular in the range of from 0.001-5% by weight, in each case based on the total weight of the preparation.

The one or more compounds of formula (I) may advantageously be used, in particular, in cosmetic and dermatological preparations in combination with insect repellents such as, for example, DEET, IR 3225, Dragorepel™ (Symrise GmbH & Co. KG).

The one or more compounds of formula (I) can advantageously be used in particular in cosmetic and dermatological preparations in combination with hair care agents and anti-dandruff active ingredients (for example climbazole, ketoconazole, piroctone oleamine, zinc-pyrithione).

The compounds of formula (I) can also advantageously be used in numerous cases in combination with one or more preservatives in preparations according to the invention. The preservatives mentioned in WO 2005/123101 are preferably selected here.

Preparations according to the invention, apart from one or more compounds of formula (I), may also contain plant extracts which can be used for cosmetic purposes. The plant extracts are preferably selected from the table of listed substances beginning on page 44 of the third edition of the handbook on the contents declaration of cosmetic agents, published by the Industrieverband Körperpflegemittel and Waschmittel e.V. (IKW), Frankfurt. The extracts mentioned in WO 2005/123101 are also particularly advantageous.

Cosmetic preparations containing one or more compounds of formula (I) may, in particular if crystalline or microcrystalline solid bodies such as, for example, inorganic micropigments are to be incorporated in the preparations, according to the invention also contain anionic, cationic, non-ionic and/or amphoteric surfactants mentioned in WO 2005/123101.

The surface-active substance may be present in a concentration between 1 and 98% by weight in the preparations according to the invention, based on the total weight of the preparations.

The oil phase of preparations according to the invention, which contain one or more compounds of formula (I) may advantageously be selected from the substance groups mentioned in WO 2005/123101.

In preferred embodiments, a composition according to the present invention, comprises one or more cosmetically acceptable carriers selected from the group consisting of (i) (alkane) diols having 3 to 10 carbon atoms, preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methylpentane-2,4-diol, 1,2-hexanediol, 1,6-hexanediol, 1,2-octanediol, dipropylene glycol, preferably 1,2-butylene glycol, 1,2-pentanediol and/or dipropylene glycol, and/or (ii-1) esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, $C_{12-15}$-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or (ii-2) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or (ii-3) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methyl-phenyl siloxane.

In other preferred embodiments, a composition according to the present invention, comprises one or more actives providing a benefit for the skin, in particular other skin irritation-reducing or skin-soothing agents, preferably selected from the group consisting of anti-inflammatory agents, compounds that alleviate itching and/or compounds that alleviate reddening which are suitable for cosmetic and/or dermatological applications, wherein the one or more actives are preferably selected from the groups consisting of:

- steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone; and/or
- natural or naturally occurring anti-inflammatory substances or substances that alleviate reddening and/or itching, in particular extracts or fractions from camomile, Aloe vera, *Commiphora* species, *Rubia* species, willow, willow-herb, oats, *calendula, arnica*, St John's wort, honeysuckle, rosemary, *Passiflora incarnata*, witch hazel, ginger or Echinacea; preferably selected from the group consisting of extracts or fractions from camomile, Aloe vera, oats, *calendula, arnica*, honeysuckle, rosemary, witch hazel, ginger or Echinacea, and/or
- pure substances, preferably alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, glabridin and licochalcone A; preferably selected from the group consisting of alpha-bisabolol, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, and licochalcone A; and/or
- skin care agents, preferably skin moisture retention regulators or skin repair agents, preferably selected from the group consisting of sodium lactate, urea and derivatives, glycerol, 1,2-pentanediol, collagen, elastin or hyaluronic acid, diacyl adipates, petrolatum, urocanic acid, lecithin, allantoin, panthenol, phytantriol, lycopene, (pseudo-) ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts, preferably selected from the group consisting of glycerol, 1,2-pentanediol, urea, hyaluronic acid, allantoin, panthenol, lanolin, alphahydroxy acids (preferably citric acid, lactic acid), vitamin E and derivatives (preferably tocopherol, tocopheryl acetate).

Preferred embodiments and further aspects of the present invention emerge from the attached patent claims and the following examples.

The examples describe the invention in more detail, without limiting the area of protection of the claims. Unless stated otherwise, all the data, in particular amounts and percentages, relate to the weight.

EXAMPLES 1

Synthesis of Compounds of Formula (I)

Examples 1.1

Di-Substituted Cyclohexyl Carbamates

Example 1.1.1 sec-Butyl-carbamic acid 2,3-dimethyl-cyclohexyl ester (BIO1845)

50.7 g (0.5 mol) sec.-Butyl isocyanate were placed in a 500 ml vessel at ambient temperature and 64.1 g (0.5 mol) 2,3-dimethylcyclohexanol were added. The reaction mixture was heated for 5 h to 150° C., cooled and subsequently 100 ml water were added. After refluxing for one hour the solution was cooled down, the phases separated and extracted once with MTBE (methyl tert.-butyl ether). The raw product was purified by distillation to yield 60.2 g product as a mixture of isomers with a purity of 99.6%.

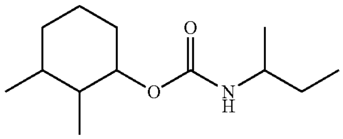 [SMILES: CCC(C)NC(=O)OC1CCCC(C)C1C]

main signals of isomer mixture:

$^1$H-NMR (400 MHz, $CDCl_3$, TMS): δ=4.66 (m, H), 4.41 (m, H), 3.62 (m, H), 2.06 (m, H), 1.68 (m, H), 1.44 (m, 2H), 1.12 (d, 6.6 Hz, 3H), 0.91 (t, 7.3 Hz, 3H), 0.89 (d, 6.9 Hz, 3H), 0.80 (d, 7.0 Hz, 3H) ppm.

$^{13}$C-NMR (400 MHz, $CDCl_3$, TMS): δ=156.2 (s), 76.2 (d), 48.2 (d), 37.8 (d), 34.2 (d), 30.0 (t), 20.8 (q), 19.1 (q), 10.3 (q), 6.1 (q) ppm.

MS (EI, major isomer): m/z=227 (not detected), 198 (27), 111 (71), 95 (20), 81 (18), 69 (100), 55 (37), 44 (94), 41 (31).

The following cyclohexyl carbamates were produced analogously to the methodology of BIO1845 as described in example 1.1.1 or BIO1824 as described in example 1.3.2, below. The cyclohexyl carbamates were obtained in comparable yields and purities (generally >99%, depending on the structure as a mixture of stereoisomers):

Example 1.1.2

Butyl-carbamic acid 2,3-dimethyl-cyclohexyl ester (BIO1842)

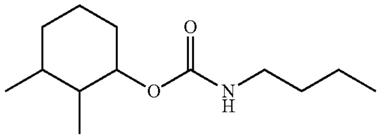

main signals of isomer mixture:

$^1$H-NMR (400 MHz, $CDCl_3$, TMS): δ=4.66 (m, 2H), 3.17 (q, 6.3 Hz, 2H), 2.05 (m, H), 1.24-1.80 (m, 11H), 0.92 (t, 7.3 Hz, 3H), 0.89 (d, 6.6 Hz, 3H), 0.79 (d, 6.9 Hz, 3H) ppm.

$^{13}$C-NMR (400 MHz, $CDCl_3$, TMS): δ=156.8 (s), 76.3 (d), 40.6 (t), 37.4 (d), 34.8 (t), 34.2 (d), 32.2 (t), 27.4 (t), 25.6 (t), 20.0 (t), 19.1 (q), 13.8 (q), 6.1 (q) ppm.

MS (EI, major isomer): m/z=227 (<1), 118 (100), 111 (49), 110 (88), 95 (53), 81 (55), 69 (83), 57 (35), 55 (54), 41 (35).

Example 1.1.3

Ethyl-carbamic acid 2,3-dimethyl-cyclohexyl ester (BIO1581)

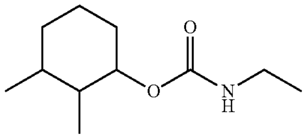

main signals of isomer mixture:

$^1$H-NMR (400 MHz, $CDCl_3$, TMS): δ=4.60-4.72 (m, 2H), 3.21 (d, q, 5.3 Hz, 7.2 Hz, 2H), 2.05 (m, H), 1.25-1.81 (m, 7H), 1.14 (t, 7.2 Hz, 3H), 0.89 (d, 6.7 Hz, 3H), 0.79 (d, 7.2 Hz, 3H) ppm.

$^{13}$C-NMR (400 MHz, $CDCl_3$, TMS): δ=156.2 (s), 76.3 (d), 37.5 (d), 35.7 (t), 34.8 (t), 34.2 (d), 27.4 (t), 25.6 (t), 19.1 (q), 15.3 (q), 6.2 (q) ppm.

MS (EI, major isomer): m/z=200 (<1), 199 (<1), 127 (3), 110 (100), 95 (62), 90 (74), 81 (67), 69 (65), 55 (37), 41 (24).

Example 1.1.4

(2-Hydroxy-phenyl)-carbamic acid 2,3-dimethyl-cyclohexyl ester (BIO1643)

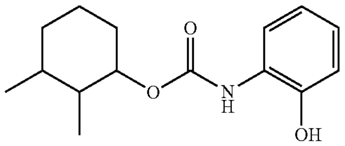 [SMILES: CC1CCCC(OC(=O)Nc2ccccc2O)C1C]

main signals of isomer mixture:

$^1$H-NMR (400 MHz, $CDCl_3$, TMS): δ=7.93 (m, H), 7.15 (d, 7.5 Hz, H), 7.05 (d, d, 7.7 Hz, 8.1 Hz, H), 6.97 (d, 8.1 Hz, H), 6.87 (d, d, 7.3 Hz, 7.7 Hz, H), 6.7 (m, H), 4.81 (t, d, 4.5 Hz, 11.6 Hz, H), 1.10-2.18 (m, 8H), 0.92 (d, 6.9 Hz, 3H), 0.86 (d, 7.1 Hz, 3H) ppm.

$^{13}$C-NMR (400 MHz, $CDCl_3$, TMS): δ=155.4 (s), 147.2 (s), 125.6 (d), 125.4 (s), 121.2 (d), 120.9 (d), 118.6 (d), 78.6 (d), 37.3 (d), 34.6 (t), 34.2 (d), 27.2 (t), 25.4 (t), 19.1 (q), 6.2 (q) ppm.

MS (EI): m/z=263 (15), 153 (100), 135 (15), 110 (21), 109 (64), 95 (9), 81 (9), 69 (51), 55 (27), 41 (11).

Example 1.1.5

(4-Ethyl-phenyl)-carbamic acid 3,5-dimethyl-cyclohexyl ester (BIO1823)

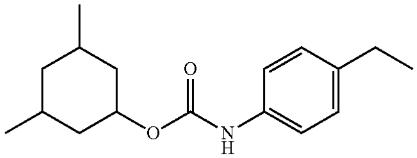 [SMILES: CCc1ccc(NC(=O)OC2CC(C)CC(C)C2)cc1]

ααα, main signals of isomer mixture:

$^1$H-NMR (400 MHz, $CDCl_3$, TMS): δ=7.27 (m, 2H), 7.13 (m, 2H), 6.46 (s, H), 4.17 (t, t 4.3 Hz, 11.4 Hz, H), 2.60 (q, 7.6 Hz, 2H), 2.03 (d, 12.1 Hz, 2H), 1.62 (d, 14.4 Hz, H), 1.55 (m, 2H), 1.21 (t, 7.6 Hz, 3H), 0.94 (d, 6.5 Hz, 6H), 0.94 (q, 11.9 Hz, 2H), 0.56 (q, 12.0 Hz, H) ppm.

$^{13}$C-NMR (400 MHz, $CDCl_3$, TMS): δ=153.4 (s), 137.8 (s), 137.2 (s), 128.0 (d), 128.0 (d), 118.5 (d), 118.5 (d), 72.7 (d), 42.9 (t), 40.4 (t), 40.4 (t), 30.4 (d), 30.4 (d), 27.9 (t), 22.1 (q), 22.1 (q), 15.9 (q) ppm.

MS (EI, minor isomer): m/z=275 (22), 165 (100), 150 (26), 132 (21), 121 (41), 111 (11), 106 (42), 69 (52), 55 (22), 41 (13).

Example 1.1.6

Cyclohexyl-carbamic acid 3,5-dimethyl-cyclohexyl ester (BIO1743)

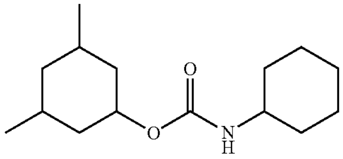 [SMILES: CC1CC(C)CC(OC(=O)NC2CCCCC2)C1]

main signals of isomer mixture:

$^1$H-NMR (400 MHz, $CDCl_3$, TMS): δ=4.59 (m, H), 4.47 (m, H), 3.47 (m, H), 1.94 (m, 2H), 1.69 (d, 13.5 Hz, H), 1.52 (m, 2H), 1.00-1.40 (m, 10H), 0.92 (d, 6.5 Hz, 6H), 0.86 (m, 2H), 0.52 (q, 11.9 Hz, H) ppm.

$^{13}$C-NMR (400 MHz, $CDCl_3$, TMS): δ=156.8 (s), 73.0 (d), 49.1 (d), 43.1 (t), 40.5 (t), 40.5 (t), 33.5 (t), 33.5 (t), 30.6 (d), 30.6 (d), 25.5 (t), 25.5 (t), 24.8 (t), 22.2 (q), 22.2 (q) ppm.

MS (EI, minor isomer): m/z=253 (2), 144 (100), 111 (26), 110 (33), 95 (61), 82 (32), 69 (96), 56 (59), 55 (71), 41 (50).

MS (EI, major isomer): m/z=253 (3), 144 (91), 111 (47), 110 (11), 95 (32), 82 (31), 69 (100), 56 (66), 55 (60), 41 (42).

Example 1.1.7

Benzyl-carbamic acid 3,5-dimethyl-cyclohexyl ester (BIO1745)

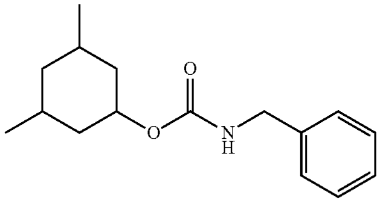 [SMILES: CC1CC(C)CC(OC(=O)NCc2ccccc2)C1]

main signals of isomer mixture:

$^1$H-NMR (400 MHz, $CDCl_3$, TMS): δ=7.34 (m, 2H), 7.28 (m, 2H), 7.27 (m, H), 4.92 (m, H), 4.65 (t, t, 4.3 Hz, 11.4 Hz, H), 4.36 (d, 5.5 Hz, 2H), 1.98 (d, 12.1 Hz, 2H), 1.60 (d, 14.5 Hz, H), 1.52 (m, 2H), 0.92 (d, 6.5 Hz, 6H), 0.86 (m, 2H), 0.53 (q, 11.9 Hz, H) ppm.

$^{13}$C-NMR (400 MHz, $CDCl_3$, TMS): δ=156.3 (s), 138.7 (s), 128.6 (d), 128.6 (d), 127.5 (d), 127.4 (d), 127.4 (d), 73.6 (d), 45.0 (t), 43.0 (t), 40.4 (t), 40.4 (t), 30.6 (d), 30.6 (d), 22.2 (q), 22.2 (q) ppm.

MS (EI, minor isomer): m/z=261 (2), 151 (100), 150 (93), 106 (29), 95 (72), 91 (59), 69 (55), 55 (43), 41 (31).

MS (EI, major isomer): m/z=261 (2), 151 (78), 150 (100), 106 (24), 95 (38), 91 (55), 69 (63), 55 (37), 41 (26).

Example 1.1.8

Ethyl-carbamic acid 3,5-dimethyl-cyclohexyl ester (BIO1561)

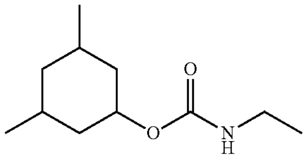

main signals of isomer mixture:

$^1$H-NMR (400 MHz, $CDCl_3$, TMS): δ=4.61 (m, 2H), 3.20 (m, 2H), 1.96 (d, 11.9 Hz, 2H), 1.60 (d, 14.4 Hz, H), 1.52 (m, 2H), 1.13 (t, 7.2 Hz, 3H), 0.92 (d, 6.6 Hz, 6H), 0.80-1.05 (m, 2H), 0.53 (q, 11.9 Hz, H) ppm.

$^{13}$C-NMR (400 MHz, $CDCl_3$, TMS): δ=156.3 (s), 73.1 (d), 43.1 (t), 40.5 (t), 40.5 (t), 38.4 (t), 30.6 (d), 30.6 (d), 22.2 (q), 22.2 (q), 15.3 (q) ppm.

MS (EI, major isomer): m/z=199 (not detected), 127 (4), 95 (41), 90 (100), 69 (65), 55 (39), 41 (62), 29 (26).

Example 1.1.9 p-Tolyl-carbamic acid 3,5-dimethyl-cyclohexyl ester (BIO1822)

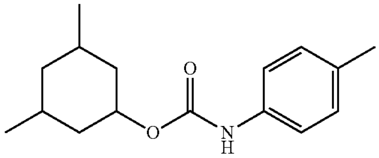

main signals of isomer mixture:

$^1$H-NMR (400 MHz, $CDCl_3$, TMS): δ=7.25 (d, 8.1 Hz, 2H), 7.10 8d, 8.3 Hz, 2H), 6.45 (m, H), 4.71 (t, t, 4.4 Hz, 11.3 Hz, H), 2.30 (s, 3H), 2.03 (d, 12.0 Hz, 2H), 1.62 (d, 14.1 Hz, H), 1.55 (m, 2H), 0.97 (q, 11.3 Hz, 2H), 0.94 (d, 6.6 Hz, 6H), 0.56 (d, t, 11.5 Hz, 12.6 Hz, H) ppm.

$^{13}$C-NMR (400 MHz, $CDCl_3$, TMS): δ=153.4 (s), 135.5 (s), 132.8 (s), 129.5 (d), 129.5 (d), 118.7 (d), 118.7 (d), 73.9 (d), 43.0 (t), 40.3 (t), 40.3 (t), 30.6 (d), 30.6 (d), 22.2 (q), 22.2 (q), 20.7 (q) ppm.

MS (EI): m/z=262 (5), 261 (24), 151 (100), 107 (72), 106 (20), 69 (45), 55 (20), 41 (11).

Example 1.1.10 n-Butyl-carbamic acid 3,5-dimethyl-cyclohexyl ester (BIO1840)

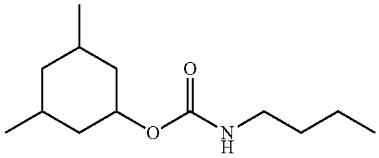 [SMILES: CCCCNC(=O)OC1CC(C)CC(C)C1]

main signals of isomer mixture:

$^1$H-NMR (400 MHz, $CDCl_3$, TMS): δ=4.58 (m, 2H), 3.14 (q, 6.3 Hz, 2H), 1.94 (d, 11.7 Hz, 2H), 1.58 (d, 12.6 Hz, H), 1.40-1.54 (m, 4H), 1.32 (m, 2H), 0.90 (d, 6.5 Hz, 6H), 0.90 (t, 7.2 Hz, 3H), 0.89 (q, 11.8 Hz, 2H), 0.50 (q, 12.0 Hz, H) ppm.

$^{13}$C-NMR (400 MHz, $CDCl_3$, TMS): δ=156.4 (s), 73.1 (d), 43.1 (t), 40.6 (t), 40.5 (t), 40.5 (t), 32.1 (t), 30.6 (d), 30.6 (d), 22.2 (q), 22.2 (q), 19.9 (t), 13.7 (q) ppm.

MS (EI): m/z=227 (1), 184 (1), 118 (100), 111 (43), 95 (28), 69 (77), 55 (28), 41 (29), 30 (19).

Example 1.1.11

Phenyl-carbamic acid 3,5-dimethyl-cyclohexyl ester (BIO1685)

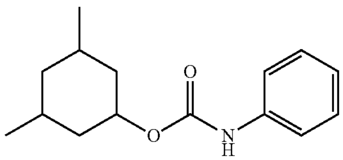 [SMILES: CC1CC(C)CC(OC(=O)Nc2ccccc2)C1]

main signals of isomer mixture:

$^1$H-NMR (400 MHz, $CDCl_3$, TMS): δ=7.37 (d, 7.9 Hz, 2H), 7.30 (m, 2H), 7.05 (m, H), 6.53 (m, H), 4.72 (t, t, 4.3 Hz, 11.4 Hz, H), 2.04 (d, 11.7 Hz, 2H), 1.63 (d, 12.5 Hz, H), 1.55 (m, 2H), 0.94 (q, 11.7 Hz, 2H), 0.94 (d, 6.5 Hz, 6H), 0.56 (d, t, 11.6 Hz, 12.6 Hz, H) ppm.

$^{13}$C-NMR (400 MHz, $CDCl_3$, TMS): δ=153.2 (s), 138.1 (s), 129.0 (d), 129.0 (d), 123.2 (d), 118.6 (d), 118.6 (d), 74.0 (d), 43.0 (t), 40.3 (t), 40.3 (t), 30.6 (d), 30.6 (d), 22.1 (q), 22.1 (q) ppm.

MS (EI): m/z=248 (3), 247 (15), 137 (29), 111 (29), 95 (34), 93 (84), 69 (100), 55 (47), 41 (35).

Example 1.1.12

Ethyl-carbamic acid 3,4-dimethyl-cyclohexyl ester (BIO1582)

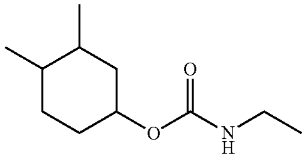

main signals of isomer mixture:

$^1$H-NMR (400 MHz, $CDCl_3$, TMS): δ=4.60 (m, 2H), 3.20 (d, q, 5.2 Hz, 7.2 Hz, 2H), 0.95-2.10 (m, 8H), 1.14 (t, 7.2 Hz, 3H), 0.83 (d, 6.9 Hz, 3H), 0.88 (d, 6.4 Hz, 3H) ppm.

$^{13}$C-NMR (400 MHz, $CDCl_3$, TMS): δ=156.2 (s), 73.7 (d), 35.7 (t), 34.5 (t), 33.3 (d), 31.9 (d), 30.7 (t), 26.3 (t), 19.2 (q), 15.3 (q), 11.9 (q) ppm.

MS (EI, major isomer): m/z=200 (<1), 127 (4), 110 (20), 95 (21), 90 (100), 81 (20), 69 (49), 55 (22), 41 (16).

Example 1.1.13

Ethyl-carbamic acid 4-isopropyl-3-methyl-cyclohexyl ester (BIO1560)

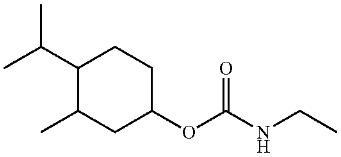 [SMILES: CCNC(=O)OC1CCC(C(C)C)C(C)C1]

main signals of isomer mixture:

$^1$H-NMR (400 MHz, $CDCl_3$, TMS): δ=4.78 (t, t, 4.2 Hz, 11.2 Hz, H), 4.61 (m, H), 0.81-2.20 (m, 9H), 1.12 (t, 7.2 Hz, 3H), 0.89 (d, 7.0 Hz, 6H), 0.87 (d, 6.6 Hz, 3H) ppm.

$^{13}$C-NMR (400 MHz, $CDCl_3$, TMS): δ=156.4 (s), 70.0 (d), 46.8 (d), 39.6 (t), 35.7 (t), 32.8 (t), 30.1 (d), 26.7 (d), 23.2 (t), 21.6 (q), 21.6 (q), 15.1 (q), 12.6 (q) ppm.

MS (EI): m/z=227 (not detected), 123 (9), 109 (4), 95 (55), 90 (100), 83 (19), 69 (16), 55 (21), 41 (15).

Example 1.1.14

Butyl-carbamic acid 2-isopropenyl-5-methyl-cyclohexyl ester (BIO1615)

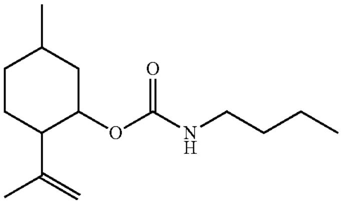 [SMILES: C=C(C)C1CCC(C)CC1OC(=O)NCCCC]

main signals of isomer mixture:

$^1$H-NMR (400 MHz, $CDCl_3$, TMS): δ=4.73 (m, 2H), 4.65 (d, t, 4.3 Hz, 10.9 Hz, H), 4.54 (m, H), 3.13 (d, t, 6.0 Hz, 6.0 Hz, 2H), 2.07 (m, 2H), 1.63-1.73 (m, 2H), 1.69 (t, 1.2 Hz, 3H), 1.56 (m, H), 1.26-1.49 (m, 5H), 0.87-1.02 (m, 2H), 0.92 (d, 6.5 Hz, 3H), 0.91 (t, 7.2 Hz, 3H) ppm.

$^{13}$C-NMR (400 MHz, $CDCl_3$, TMS): δ=156.4 (s), 146.8 (s), 111.5 (t), 73.8 (d), 51.0 (d), 41.0 (t), 40.6 (t), 34.2 (t), 32.1 (t), 31.4 (d), 30.7 (t), 22.0 (q), 19.9 (t), 19.5 (q), 13.7 (q) ppm.

MS (EI, major isomer): m/z=254 (1), 253 (4), 136 (100), 118 (87), 107 (35), 93 (40), 81 (56), 67 (20), 57 (20), 41 (32), 29 (10).

Examples 1.2

Unsubstituted Cyclohexyl Carbamates

Example 1.2.1

Phenyl-carbamic acid cyclohexyl ester (BIO1741)

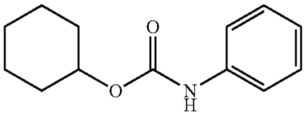 [SMILES: O=C(Nc1ccccc1)OC1CCCCC1]

$^1$H-NMR (400 MHz, $CDCl_3$, TMS): δ=7.38 (m, 2H), 7.30 (m, 3H), 7.05 (m, H), 6.51 (m, H), 4.76 (t, t, 3.9 Hz, 9.0 Hz, H), 1.94 (m, 2H), 1.75 (m, 2H), 1.56 (m, H), 1.42 (m, 4H), 1.27 (m, H) ppm.

$^{13}$C-NMR (400 MHz, $CDCl_3$, TMS): δ=153.2 (s), 138.1 (s), 129.0 (d), 129.0 (d), 123.2 (d), 118.5 (d), 118.5 (d), 73.7 (d), 31.9 (t), 31.9 (t), 25.4 (t), 23.8 (t), 23.8 (t) ppm.

MS (EI): m/z=220 (4), 219 (25), 137 (59), 132 (15), 119 (30), 93 (100), 83 (54), 67 (24), 55 (83), 41 (40).

Examples 1.3

Mono-Substituted Cyclohexyl Carbamates

Example 1.3.1

Butyl-carbamic acid 3-methyl-cyclohexyl ester (BIO1821)

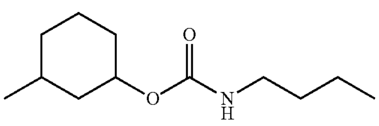

main signals of isomer mixture:

$^1$H-NMR (400 MHz, $CDCl_3$, TMS): δ=4.57 (m, 2H), 3.16 (m, 2H), 1.98 (d, 11.4 Hz, H), 1.75 (d, 13.5 Hz, H), 1.61 (d, 13.0 Hz, H), 1.47 (m, 2H), 1.34 (m, 2H), 1.25-1.56 (m, 3H), 1.16 (m, H), 0.93 (m, H), 0.92 (t, 7.3 Hz, 3H), 0.92 (d, 7.0 Hz, 3H), 0.80 (q, 12.6 Hz, H) ppm.

$^{13}$C-NMR (400 MHz, $CDCl_3$, TMS): δ=156.3 (s), 73.4 (d), 41.0 (t), 40.6 (t), 34.1 8t), 32.1 (t), 32.0 (t), 31.4 (d9, 24.0 (t), 22.3 (q), 19.9 (t), 13.7 (q) ppm.

MS (EI, minor isomer): m/z=214 (1), 213 (1), 170 (2), 126 (2), 118 (100), 97 (32), 81 (14), 55 (31), 41 (10), 30 (14).

MS (EI, major isomer): m/z=214 (1), 213 (2), 170 (3), 126 (9), 118 (100), 97 (45), 81 (11), 55 (36), 41 (11), 30 (12).

Example 1.3.2 p-Tolyl-carbamic acid 2-isopropyl-cyclohexyl ester (BIO1824)

75.6 g (0.56 mol) of para-tolylisocyanate were placed with 500 ml toluene in a one liter vessel and subsequently 73.4 g (0.51 mol) of 2-isopropylcyclohexanol were added. The reaction mixture was heated to reflux for 6 hours. After cooling to room temperature 50 g of water were added and the mixture was refluxed for one more hour. After phase separation the solvent was stripped off and the crude product recrystallized from 235 g of n-heptane. The product (79.8 g) was obtained in form of off-white crystals in 99.2% purity. This corresponds to a theoretical yield of 56%.

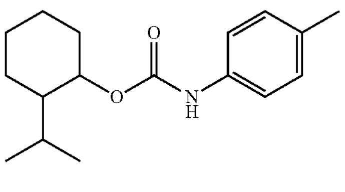 [SMILES: Cc1ccc(NC(=O)OC2CCCCC2C(C)C)cc1]

main signals of isomer mixture:

$^1$H-NMR (400 MHz, $CDCl_3$, TMS): δ=7.28 (m, 2H), 7.10 (m, 2H), 6.50 (m, H), 5.19 (m, H); 2.30 (s, 3H), 2.07 (m, H), 1.70-1.81 (m, 2H), 1.22-1.55 (m, 6H), 1.07 (m, H), 0.92 (d, 6.7 Hz, 3H), 0.90 (d, 6.7 Hz, 3H) ppm.

$^{13}$C-NMR (400 MHz, $CDCl_3$, TMS): δ=153.4 (s), 135.6 (s), 132.7 (s), 129.5 (d), 129.5 (d), 118.6 (d), 118.6 (d), 71.7 (d), 47.2 (d), 30.9 (t), 29.5 (d), 26.0 (t), 25.1 (t), 20.8 (q), 20.7 (q), 20.7 (q), 20.4 (t) ppm.

MS (EI): m/z=276 (5), 275 (30), 151 (89), 125 (17), 107 (100), 83 (32), 69 (74), 57 (21), 41 (18).

Example 1.3.3

Butyl-carbamic acid 2-isopropyl-cyclohexyl ester (BIO1841)

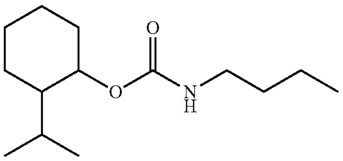 [SMILES: CCCCNC(=O)OC1CCCCC1C(C)C]

main signals of isomer mixture:

$^1$H-NMR (400 MHz, $CDCl_3$, TMS): δ=5.06 (m, H), 4.65 (m, H), 3.17 (q, 6.4 Hz, 2H), 2.01 (t, 13.8 Hz, H), 1.74 (m, H), 1.68 (d, 10.3 Hz, H), 1.41-1.53 (m, 3H), 1.35 (m, 2H), 1.26 (m, H), 1.24 (m, H), 1.02 (m, H), 0.93 (t, 7.3 Hz, 3H), 0.90 (d, 6.5 Hz, 6 Hz) ppm.

$^{13}$C-NMR (400 MHz, $CDCl_3$, TMS): δ=156.5 (s), 70.8 (d), 47.2 (d), 40.7 (t), 32.2 (t), 31.1 (t), 29.5 (d), 26.1 (t), 25.0 (t), 20.8 (q), 20.7 (q), 20.5 (t), 19.9 (t), 13.8 (q) ppm.

MS (EI, major isomer): m/z=241 (<1), 198 (2), 124 (84), 118 (100), 109 (36), 99 (26), 81 (64), 69 (71), 57 (61), 41 (37).

MS (EI, minor isomer): m/z=241 (<1), 198 (1), 124 (100), 118 (97), 109 (41), 99 (12), 81 (65), 69 (71), 57 (61), 41 (41).

Example 1.3.4 n-Hexyl-carbamic acid 2-isopropyl-cyclohexyl ester (BIO1851)

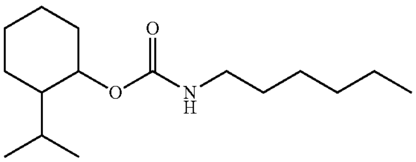 [SMILES: CCCCCCNC(=O)OC1CCCCC1C(C)C]

main signals of isomer mixture:

$^1$H-NMR (400 MHz, $CDCl_3$, TMS): δ=5.06 (m, H), 4.61 8m, H), 3.15 (m, 2H), 1.99 (d, 13.5 Hz, H), 1.64-1.78 (m, 2H), 1.47 (m, 4H), 1.19-1.40 (m, 10H), 1.02 (m, H), 0.90 (d, 7.0 Hz, 6H), 0.89 (t, 6.6 Hz, 3H) ppm.

$^{13}$C-NMR (400 MHz, $CDCl_3$, TMS): δ=156.6 (s), 70.7 (d), 47.3 (d), 41.0 (t), 31.6 (t), 31.1 (t), 31.0 (t), 29.5 (d), 26.5 (t), 26.1 (t), 25.0 (t), 22.6 (t), 20.8 (q), 20.8 (q), 20.5 (t), 14.0 (q) ppm.

MS (EI, major isomer): m/z=269 (<1), 146 (95), 124 (86), 109 (34), 81 (59), 69 (100), 57 (45), 43 (52), 41 (40).

MS (EI, minor isomer): m/z=269 (<1), 146 (90), 124 (97), 109 (38), 81 (54), 69 (100), 57 (44), 43 (52), 41 (44).

Example 1.3.5

Benzyl-carbamic acid 2-isopropyl-cyclohexyl ester (BIO1748)

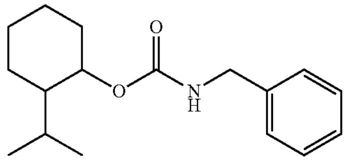 [SMILES: CC(C)C1CCCCC1OC(=O)NCc1ccccc1]

main signals of isomer mixture:

$^1$H-NMR (400 MHz, $CDCl_3$, TMS): δ=7.34 (m, 2H), 7.28 (m, 2H), 7.27 (m, H), 5.12 (m, H), 4.93 (m, H), 4.38 (m, 2H), 2.03 (m, H), 1.64-1.76 (m, 2H), 0.99-1.52 (m, 7H), 0.89 (d, 6.3 Hz, 6H) ppm.

$^{13}$C-NMR (400 MHz, $CDCl_3$, TMS): δ=156.5 (s), 138.8 (s), 128.6 (d), 18.6 (d), 127.5 (d), 127.5 (d), 127.4 (d), 71.3 (d), 47.2 (d), 45.0 (t), 31.0 (t), 29.5 (t), 26.0 (d), 25.0 (t), 20.8 (q), 20.8 (q), 20.4 (t) ppm.

MS (EI, major isomer): m/z=275 (<1), 151 (59), 150 (44), 124 (44), 109 (34), 106 (35), 91 (53), 81 (100), 69 (56), 55 (26), 41 (31).

MS (EI, minor isomer): m/z=275 (<1), 151 (64), 150 (65), 124 (50), 109 (39), 106 (30), 91 (69), 81 (100), 69 (60), 55 (30), 41 (42).

Example 1.3.6

(2-Methoxy-phenyl)-carbamic acid 2-isopropyl-cyclohexyl ester (BIO1744)

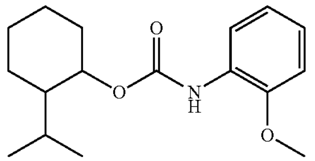 [SMILES: COc1ccccc1NC(=O)OC1CCCCC1C(C)C]

main signals of isomer mixture:

$^1$H-NMR (400 MHz, $CDCl_3$, TMS): δ=8.12 (m, H), 7.18 (d, 7.4 Hz, H), 6.98 (m, H), 6.95 (m, H), 6.85 (m, H), 5.21 (m, H), 3.88 (s, 3H), 2.04-2.15 (m, 2H), 1.15-1.82 (m, 7H), 1.08 (m, H), 0.92 (d, 6.9 Hz, 3H), 0.92 (d, 7.0 Hz, 3H) ppm.

$^{13}$C-NMR (400 MHz, $CDCl_3$, TMS): δ=153.3 (s), 147.4 (s), 128.0 (s), 122.5 (d), 121.1 (d), 118.0 (d), 109.9 (d), 71.6 (d), 55.6 (q), 47.2 (d), 30.9 (t), 29.4 (d), 26.0 (t), 25.1 (t), 20.8 (q), 20.8 (q), 20.4 (t) ppm.

MS (EI, major isomer): m/z=292 (3), 291 (21), 167 (45), 123 (100), 108 (46), 81 (46), 69 (87), 55 (29), 41 (36).

MS (EI, minor isomer): m/z=292 (3), 291 (21), 167 (43), 123 (100), 108 (38), 81 (35), 69 (76), 55 (25), 41 (32).

Example 1.3.7

Cyclohexyl-carbamic acid 4-tert-butyl-cyclohexyl ester (BIO1747)

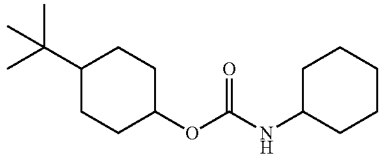 [SMILES: CC(C)(C)C1CCC(OC(=O)NC2CCCCC2)CC1]

main signals of isomer mixture:

$^1$H-NMR (400 MHz, $CDCl_3$, TMS): δ=4.44-4.54 (m, 2H), 3.47 (m, H), 2.05 (d, 12.3 Hz, 2H), 1.92 (d, 12.3 Hz, 2H), 1.79 (d, 13.2 Hz, 2H), 1.69 (d, 13.2 Hz, 2H), 1.59 (d, 12.8 Hz, H), 0.95-1.46 (m, 9H), 0.97 (d, 11.7 Hz, H), 0.85 (s, 9H) ppm.

$^{13}$C-NMR (400 MHz, $CDCl_3$, TMS): δ=155.5 (s), 73.7 (d), 49.6 (d), 47.2 (d), 33.5 (t), 33.5 (t), 32.6 8t), 32.6 (t), 32.3 (s), 27.6 (q), 27.6 (q), 27.6 (q), 25.5 (t), 25.5 (t), 25.5 (t), 24.8 (t) ppm.

MS (EI, minor isomer): m/z=281 (not detected), 144 (84), 83 (25), 82 (36), 67 (31), 57 (100), 56 (24), 41 (32).

MS (EI, major isomer): m/z=281 (<1), 144 (93), 83 (33), 82 (32), 67 (33), 57 (100), 56 (36), 41 (31).

Examples 1.4

Tri-Substituted Cyclohexyl Carbamates

Example 1.4.1 n-Butyl-carbamic acid 2,3,6-trimethyl-cyclohexyl ester (BIO1617)

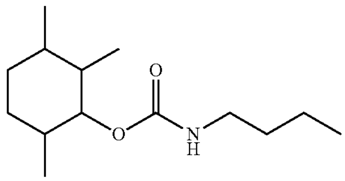 [SMILES: CCCCNC(=O)OC1C(C)CCC(C)C1C]

main signals of isomer mixture:

$^1$H-NMR (400 MHz, $CDCl_3$, TMS): δ=4.72 (m, H), 4.15 (t, 10.2 Hz, H), 3.18 (m, 2H), 1.92 (m, H), 1.49 (m, 2H), 1.35 (m, 2H), 0.92-1.78 (m, 6H), 0.85-0.95 (m, 12H) ppm.

$^{13}$C-NMR (400 MHz, $CDCl_3$, TMS): δ=157.4 (s), 82.7 (d), 40.7 (t), 40.6 (d), 36.6 (d), 34.6 (t), 32.9 (t), 32.2 (t), 20.0 (q), 19.9 (d), 19.9 (t), 18.6 (q), 15.1 (q), 13.8 (q) ppm.

MS (EI, major): m/z=241 (8), 198 (5), 124 (73), 118 (100), 109 (39), 95 (31), 82 (31), 69 (65), 55 (23), 41 (22).

Example 1.4.2

(2-Methoxy-phenyl)-carbamic acid 2,3,6-trimethyl-cyclohexyl ester (BIO1701)

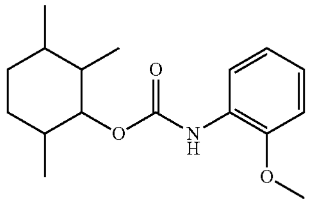 [SMILES: COc1ccccc1NC(=O)OC1C(C)CCC(C)C1C]

main signals of isomer mixture:

$^1$H-NMR (400 MHz, $CDCl_3$, TMS): δ=8.13 (m, H), 7.24 (m, H), 6.92-7.00 (m, 2H), 6.85 (m, H), 4.29 (t, 10.0 Hz, H), 3.86 (s, 3H), 0.99-1.76 (m, 7H), 0.94 (d, 6.4 Hz, 6H), 0.94 (d, 6.6 Hz, 3H) ppm.

$^{13}$C-NMR (400 MHz, $CDCl_3$, TMS): δ=154.0 (s), 147.5 (s), 128.1 (s), 122.4 (d), 121.1 (d), 118.0 (d), 109.9 (d), 83.4 (d), 55.6 (q), 44.4 (d), 38.1 (d), 37.8 (d), 34.6 (t), 32.9 (t), 20.0 (q), 18.6 (q), 15.2 (q) ppm.

MS (EI, major isomer): m/z=291 (50), 190 (5), 167 (55), 150 (12), 123 (100), 108 (25), 83 (19), 69 (57), 55 (21), 41 (14).

Example 1.4.3 sec-Butyl-carbamic acid 3,3,5-trimethyl-cyclohexyl ester (BIO1844)

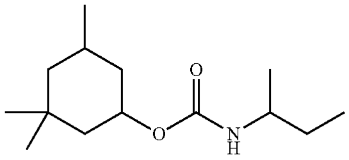 [SMILES: CCC(C)NC(=O)OC1CC(C)CC(C)(C)C1]

main signals of isomer mixture:

$^1$H-NMR (400 MHz, $CDCl_3$, TMS): δ=4.75 (t, t, 4.1 Hz, 11.5 Hz, H), 4.38 (m, H), 3.60 (m, H), 2.00 (d, 11.4 Hz, H), 1.70 (d, 12.3 Hz, H), 1.66 (m, H), 1.43 (m, 2H), 1.31 (d, 13.2 Hz, H), 1.10 (d, 6.8 Hz, 3H), 1.04 (m, H), 0.93 (s, 6H), 0.89 (t, 7.5 Hz, 3H), 0.89 (d, 6.5 Hz, 3H), 0.80 (m, H), 0.76 (t, 12.5 HZ, H) ppm.

$^{13}$C-NMR (400 MHz, $CDCl_3$, TMS): δ=155.8 (s), 71.1 (d), 48.2 (d), 47.6 (t), 44.4 (t), 41.0 (t), 33.1 (q), 32.2 (s), 30.0 (t), 27.1 (d), 25.6 (q), 22.3 (q), 20.7 (q), 10.3 (q) ppm.

MS (EI, major isomer): m/z=241 (not detected), 226 (<1), 212 (38), 168 (28), 125 (35), 109 (23), 83 (39), 69 (100), 57 (31), 44 (86), 41 (32).

Example 1.4.4 n-Butyl-carbamic acid 3,3,5-trimethyl-cyclohexyl ester (BIO1616)

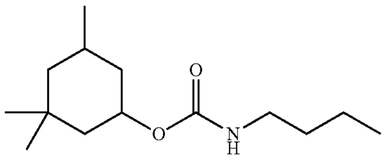 [SMILES: CCCCNC(=O)OC1CC(C)CC(C)(C)C1]

main signals of isomer mixture:

$^1$H-NMR (400 MHz, $CDCl_3$, TMS): δ=4.77 (t, t, 4.1 Hz, 11.6 Hz, H), 4.64 (m, H), 3.16 (q, 6.3 Hz, 2H), 2.01 (d, 11.6 Hz, H), 1.63-1.75 (m, 3H), 1.47 (m, 2H), 1.29-1.39 (m, 3H), 1.03 (m, H), 0.94 (s, 6H), 0.92 (t, 7.3 Hz, 3H), 0.90 (d, 6.5 Hz, 3H), 0.71-0.85 (m, 2H) ppm.

$^{13}$C-NMR (400 MHz, $CDCl_3$, TMS): δ=156.4 (s), 71.2 (d), 47.6 (t), 44.4 (t), 40.9 (t), 40.6 (t), 33.1 (q), 32.2 (t), 32.1 (s), 27.1 (d), 25.5 (q), 22.3 (q), 19.9 (t), 13.7 (q) ppm.

MS (EI): m/z=242 (<1), 241 (<1), 125 (17), 118 (100), 109 (36), 83 (29), 69 (57), 57 (18), 55 (17), 41 (21).

Example 1.4.5

(2-Methoxy-phenyl)-carbamic acid 3,3,5-trimethyl-cyclohexyl ester (BIO1703)

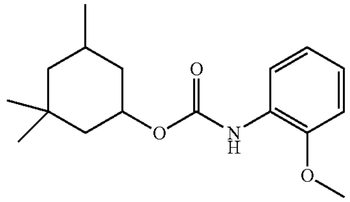

main signals of isomer mixture:

$^1$H-NMR (400 MHz, $CDCl_3$, TMS): δ=8.09 (m, H), 7.17 (m, H), 6.96 (m, 2H), 6.84 (m, H), 4.89 (t, t, 4.4 Hz, 11.6 Hz, H), 3.85 (s, 3H), 2.08 (d, 12.0 Hz, H), 1.78 (d, 12.1 Hz, H), 1.73 (m, H), 1.35 (d, 13.2 Hz, H), 1.14 (t, 12.0 Hz. H), 0.97 (s, 3H), 0.96 (s, 3H), 0.92 (d, 6.5 Hz, 3H), 0.90 (m, H), 0.80 (t, 12.7 Hz, H) ppm.

$^{13}$C-NMR (400 MHz, $CDCl_3$, TMS): δ=153.2 (s), 147.5 (s), 127.9 (s), 122.5 (d), 121.1 (d), 118.1 (d), 109.9 (d), 71.9 (d), 55.6 (q), 47.6 (t), 44.3 (t), 40.8 (t), 33.1 (q), 32.3 (s), 27.1 (d), 25.5 (q), 22.3 (q) ppm.

MS (EI): m/z=292 (12), 291 (62), 167 (53), 123 (100), 108 (31), 83 (18), 69 (52), 55 (17), 41 (19).

Example 1.4.6 n-Hexyl-carbamic acid 3,3,5-trimethyl-cyclohexyl ester (BIO1850)

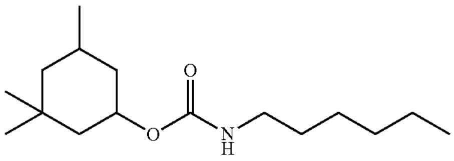 [SMILES: CCCCCCNC(=O)OC1CC(C)CC(C)(C)C1]

main signals of isomer mixture:

$^1$H-NMR (400 MHz, $CDCl_3$, TMS): δ=4.77 (t, 11.5 Hz, H), 4.62 (m, H), 3.15 (q, 6.5 Hz, 2H), 2.00 (d, 11.4 Hz, H), 1.62-1.75 (m, 2H), 1.47 (m, 2H), 1.24-1.35 (m, 8H), 1.04 (m, H), 0.94 (s, 6H), 0.90 (d, 6.4 Hz, 3H), 0.88 (t, 6.9 Hz, 3H), 0.76 (m, H) ppm.

$^{13}$C-NMR (400 MHz, $CDCl_3$, TMS): δ=156.4 (s), 71.2 (d), 47.6 (t), 44.5 (t), 41.0 (t), 41.0 (t), 33.1 (q), 32.2 (s), 31.5 (t), 30.0 (t), 27.1 (d), 26.4 (t), 25.6 (q), 22.6 (t), 22.3 (q), 14.0 (q) ppm.

MS (EI, minor isomer): m/z=270 (<1), 269 (1), 146 (100), 125 (16), 109 (35), 83 (36), 69 (82), 55 (23), 41 (32), 30 (24).

MS (EI, major isomer): m/z=270 (<1), 269 (1), 146 (100), 125 (28), 109 (34), 83 (39), 69 (89), 55 (23), 41 (28), 30 (24).

Example 1.4.7

Ethyl-carbamic acid 1,7,7-trimethyl-bicyclo[2.2.1]hept-2-yl ester (BIO1573)

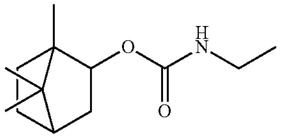 [SMILES: CCNC(=O)OC1CC2CCC1(C)C2(C)C]

main signals of isomer mixture:

$^{1}$H-NMR (400 MHz, $CDCl_3$, TMS): δ=4.83 (d, d, d, 10.0 Hz, 3.4 Hz, 2.0 Hz, H), 4.63 (m, H), 3.22 (d, q, 5.9 Hz, 7.2 Hz, 2H), 2.33 (m, H), 1.88 (m, H), 1.73 (m, H), 1.66 (m, H), 1.17-1.32 (m, 2H), 1.15 (t, 7.2 Hz, 3H), 1.01 (m, H), 0.90 (s, 3H), 0.86 (s, 3H), 0.84 (s, 3H) ppm.

$^{13}$C-NMR (400 MHz, $CDCl_3$, TMS): δ=157.0 (s), 79.9 (d), 48.7 (s), 47.8 (s), 44.9 (d), 36.9 (t), 35.8 (t), 28.1 (t), 27.1 (t), 19.8 (q), 18.8 (q), 15.3 (q), 13.5 (q) ppm.

MS (EI): m/z=226 (2), 225 (12), 136 (49), 121 (34), 108 (21), 95 (100), 55 (12), 41 (19), 29 (13).

EXAMPLE 2

Adipogenesis Assay (In Vitro)

3T3-L1 cells (mouse embryonic fibroblast-like adipocyte cell line) are seeded in a 48-well plate with collagen I-coating in a concentration of $3\times10^4$ cells/well. After 72 h cultivation at 37° C. and 5% $CO_2$ in DMEM (Dulbecco's Modified Eagle Medium), enriched with 10% calf serum, various concentrations of the test substances in DMEM, enriched with 10% foetal calf serum and to which are added 1 μg/ml insulin, 0.25 μM dexamethasone and 0.5 mM IBMX (3-isobutyl-1-methylxanthine), are added and incubated for a further 48 h. A media change takes place, in that DMEM, enriched with 10% foetal calf serum and with 1 μg/ml insulin added, are applied. After renewed cultivation for 48 h, a further media change takes place, in which DMEM, enriched with 10% foetal calf serum, is applied.

After a further incubation for 72 h, the intracellularly stored lipids are quantified as a measure for the differentiation of the cells by measuring the fluorescence after staining of the lipids with the fluorescent dye Nile Red.

The inhibition of the adipogenesis in the presence of the test substances is calculated according to the following equation:

$$\text{Inhibition of the adipogenesis [\%]} = 100 - \left(\frac{RFU\text{ test substance} - RFU\text{ control without cells}}{RFU\text{ control} - RFU\text{ control without cells}} \times 100\right)$$

wherein

RFU test substance=relative fluorescent units of the wells with test substance and with cells RFU control=relative fluorescent units of the wells without test substance, but with cells RFU control without cells=relative fluorescent units of the wells without test substance and without cells The $IC_{50}$ is calculated from the adipogenesis inhibition [%] in a series of dilutions of tested samples. This is the concentration at which the adipogenesis is 50% inhibited.

TABLE 2

Adipogenesis inhibition of the individual substances (mean values of at least 2 independent tests)

| | test substance | $IC_{50}$ [mM] |
|---|---|---|
| BIO1741 | Phenyl-carbamic acid cyclohexyl ester | 0.44 |
| BIO1841 | Butyl-carbamic acid 2-isopropyl-cyclohexyl ester<br>tested as following mixture of isomers:<br>79% Butyl-carbamic acid (1R*,2R*)-2-isopropyl-cyclohexyl ester<br>20% Butyl-carbamic acid (1R*,2S*)-2-isopropyl-cyclohexyl ester | 0.059 |
| BIO1747 | Cyclohexyl-carbamic acid 4-tert-butyl-cyclohexyl ester | 0.12 |
| BIO1851 | Hexyl-carbamic acid 2-isopropyl-cyclohexyl ester | 0.086 |
| BIO1748 | Benzyl-carbamic acid 2-isopropyl-cyclohexyl ester | 0.059 |
| BIO1824 | p-Tolyl-carbamic acid 2-isopropyl-cyclohexyl ester<br>tested as following mixture of isomers:<br>92% (1S*,2S*)-2-(1-methylethyl)cyclohexyl (4-methylphenyl)carbamate<br>8% (1S*,2R*)-2-(1-methylethyl)cyclohexyl (4-methylphenyl)carbamate | 0.092 |
| BIO1823 | (4-Ethyl-phenyl)-carbamic acid 3,5-dimethyl-cyclohexyl ester<br>tested as following mixture of isomers:<br>76.7% (4-Ethyl-phenyl)-carbamic acid (1alpha,3alpha,5alpha)-3,5-dimethyl-cyclohexylester + (4-Ethyl-phenyl)-carbamic acid (1alpha*,3alpha*,5beta*)-3,5-dimethyl-cyclohexylester<br>23.1% (4-Ethyl-phenyl)-carbamic acid (1alpha,3beta,5beta)-3,5-dimethyl-cyclohexylester | 0.062 |
| BIO1845 | sec-Butyl-carbamic acid 2,3-dimethyl-cyclohexyl ester | 0.096 |
| BIO1743 | Cyclohexyl-carbamic acid 3,5-dimethyl-cyclohexyl ester | 0.091 |
| BIO1842 | Butyl-carbamic acid 2,3-dimethyl-cyclohexyl ester | 0.15 |
| BIO1581 | Ethyl-carbamic acid 2,3-dimethyl-cyclohexyl ester | 0.16 |

TABLE 2-continued

Adipogenesis inhibition of the individual substances (mean values of at least 2 independent tests)

| | test substance | $IC_{50}$ [mM] |
|---|---|---|
| BIO1745 | Benzyl-carbamic acid 3,5-dimethyl-cyclohexyl ester | 0.12 |
| BIO1840 | Butyl-carbamic acid 3,5-dimethyl-cyclohexyl ester | 0.16 |
| BIO1685 | Phenyl-carbamic acid 3,5-dimethyl-cyclohexyl ester tested as following mixture of isomers: 94% Phenyl-carbamic acid (1alpha,3alpha,5alpha)-3,5-dimethyl-cyclohexyl ester + Phenyl-carbamic acid (1alpha*,3alpha*,5beta*)-3,5-dimethyl-cyclohexyl ester 5% Phenyl-carbamic acid (1alpha,3beta,5beta)-3,5-dimethyl-cyclohexyl ester | 0.34 |
| BIO1643 | (2-Hydroxy-phenyl)-carbamic acid 2,3-dimethyl-cyclohexyl ester | 0.014 |
| BIO1822 | p-Tolyl-carbamic acid 3,5-dimethyl-cyclohexyl ester tested as following mixture of isomers: 81% p-Tolyl-carbamic acid (1alpha,3alpha,5alpha)-3,5-dimethyl-cyclohexyl ester + p-Tolyl-carbamic acid (1alpha*,3alpha*,5beta*)-3,5-dimethyl-cyclohexyl ester 19% p-Tolyl-carbamic acid (1alpha,3beta,5beta)-3,5-dimethyl-cyclohexyl ester | 0.17 |
| BIO1615 | Butyl-carbamic acid 2-isopropenyl-5-methyl-cyclohexyl ester | 0.16 |
| BIO1617 | Butyl-carbamic acid 2,3,6-trimethyl-cyclohexyl ester | 0.079 |
| BIO1844 | sec-Butyl-carbamic acid 3,3,5-trimethyl-cyclohexyl ester tested as following mixture of isomers: 91% sec-Butyl-carbamic acid (1R*,5R*)-3,3,5-trimethyl-cyclohexyl ester 7% sec-Butyl-carbamic acid (1R*,5S*)-3,3,5-trimethyl-cyclohexyl ester | 0.089 |
| BIO1616 | Butyl-carbamic acid 3,3,5-trimethyl-cyclohexyl ester tested as following mixture of isomers: 92% Butyl-carbamic acid (1R*,5R*)-3,3,5-trimethyl-cyclohexyl ester 7% Butyl-carbamic acid (1R*,5S*)-3,3,5-trimethyl-cyclohexyl ester | 0.12 |
| BIO1701 | (2-Methoxy-phenyl)-carbamic acid 2,3,6-trimethyl-cyclohexyl ester | 0.11 |
| BIO1850 | Hexyl-carbamic acid 3,3,5-trimethyl-cyclohexyl ester tested as following mixture of isomers: 90% Hexyl-carbamic acid (1R*,5R*)-3,3,5-trimethyl-cyclohexyl ester 7% Hexyl-carbamic acid (1R*,5S*)-3,3,5-trimethyl-cyclohexyl ester | 0.36 |
| BIO1703 | (2-Methoxy-phenyl)-carbamic acid 3,3,5-trimethyl-cyclohexyl ester tested as following mixture of isomers: 92% (2-Methoxy-phenyl)-carbamic acid (1R*,5R*)-3,3,5-trimethyl-cyclohexyl ester 7% (2-Methoxy-phenyl)-carbamic acid (1R*,5S*)-3,3,5-trimethyl-cyclohexyl ester | 0.051 |

EXAMPLE 3

Lipogenesis Assay (In Vitro)

Lipogenesis is perceived as the storage of triglycerides in adipocytes. The inhibition of this storage can take place by means of the inhibition of the activity of extracellular lipoprotein lipase (LPL) in that the hydrolysis of extracellular triglycerides and therefore the absorption of free fatty acids by adipocytes are reduced. As a preliminary test, the inhibition of pancreatic lipase (PL) is investigated.

Example 3.1

Inhibition of PL

PL (Sigma-Aldrich), in the presence of test substances in different use concentrations has methylumbelliferyl oleate (MUF oleate) added as a substrate. Fluorescent methylumelliferon (MUF), is produced by hydrolysis of the MUF oleate by PL and is quantified. The inhibition of the hydrolysis of the MUF oleate is a measure of the inhibition of activity of the PL.

$$\text{Inhibition of the } PL \ [\%] = 100 - \left(\frac{MUF \text{ test substance} - MUF \text{ control without } PL}{MUF \text{ control} - MUF \text{ control without } PL} \times 100\right)$$

wherein

MUF test substance=MUF concentration of the wells with test substance and with PL MUF control=MUF concentration of the wells without test substance, but with PL MUF control without PL=MUF concentration of the wells without test substance and without PL The $IC_{50}$ is calculated from the inhibition of the PL [%] in a series of dilutions of tested samples. This is the concentration, at which the activity of the PL is 50% inhibited.

TABLE 3.1

| Inhibition of the PL by the individual substances (mean values of at least 2 independent tests) | | |
|---|---|---|
| | test substance | $IC_{50}$ [mM] |
| BIO1841 | Butyl-carbamic acid 2-isopropyl-cyclohexyl ester<br>tested as following mixture of isomers:<br>79% Butyl-carbamic acid (1R*,2R*)-2-isopropyl-cyclohexyl ester<br>20% Butyl-carbamic acid (1R*,2S*)-2-isopropyl-cyclohexyl ester | 0.78 |
| BIO1851 | Hexyl-carbamic acid 2-isopropyl-cyclohexyl ester | 1.24 |
| BIO1748 | Benzyl-carbamic acid 2-isopropyl-cyclohexyl ester | 2.17 |
| BIO1821 | Butyl-carbamic acid 3-methyl-cyclohexyl ester | 0.51 |
| BIO1744 | (2-Methoxy-phenyl)-carbamic acid 2-isopropyl-cyclohexyl ester | 0.23 |
| BIO1845 | sec-Butyl-carbamic acid 2,3-dimethyl-cyclohexyl ester | 0.72 |
| BIO1842 | Butyl-carbamic acid 2,3-dimethyl-cyclohexyl ester | 0.67 |
| BIO1581 | Ethyl-carbamic acid 2,3-dimethyl-cyclohexyl ester | 0.24 |
| BIO1745 | Benzyl-carbamic acid 3,5-dimethyl-cyclohexyl ester | 0.13 |
| BIO1560 | Ethyl-carbamic acid 4-isopropyl-3-methyl-cyclohexyl ester | 0.56 |
| BIO1582 | Ethyl-carbamic acid 3,4-dimethyl-cyclohexyl ester | 0.42 |
| BIO1840 | Butyl-carbamic acid 3,5-dimethyl-cyclohexyl ester | 0.55 |
| BIO1561 | Ethyl-carbamic acid 3,5-dimethyl-cyclohexyl ester<br>tested as following mixture of isomers:<br>61.8% Ethyl carbamic acid (1alpha,3alpha,5alpha)-3,5-dimethyl-cyclohexylester<br>27.6% Ethyl carbamic acid (1alpha,3beta,5beta)-3,5-dimethyl-cyclohexylester<br>9.9% Ethyl carbamic acid (1alpha*,3alpha*,5beta*)-3,5-dimethyl-cyclohexylester | 0.40 |
| BIO1643 | (2-Hydroxy-phenyl)-carbamic acid 2,3-dimethyl-cyclohexyl ester | 0.42 |
| BIO1615 | Butyl-carbamic acid 2-isopropenyl-5-methyl-cyclohexyl ester | 0.34 |
| BIO1617 | Butyl-carbamic acid 2,3,6-trimethyl-cyclohexyl ester | 1.38 |
| BIO1844 | sec-Butyl-carbamic acid 3,3,5-trimethyl-cyclohexyl ester<br>tested as following mixture of isomers:<br>91% sec-Butyl-carbamic acid (1R*,5R*)-3,3,5-trimethyl-cyclohexyl ester<br>7% sec-Butyl-carbamic acid (1R*,5S*)-3,3,5-trimethyl-cyclohexyl ester | 0.35 |
| BIO1616 | Butyl-carbamic acid 3,3,5-trimethyl-cyclohexyl ester<br>tested as following mixture of isomers:<br>92% Butyl-carbamic acid (1R*,5R*)-3,3,5-trimethyl-cyclohexyl ester<br>7% Butyl-carbamic acid (1R*,5S*)-3,3,5-trimethyl-cyclohexyl ester | 0.90 |
| BIO1701 | (2-Methoxy-phenyl)-carbamic acid 2,3,6-trimethyl-cyclohexyl ester | 0.47 |
| BIO1850 | Hexyl-carbamic acid 3,3,5-trimethyl-cyclohexyl ester<br>tested as following mixture of isomers:<br>90% Hexyl-carbamic acid (1R*,5R*)-3,3,5-trimethyl-cyclohexyl ester<br>7% Hexyl-carbamic acid (1R*,5S*)-3,3,5-trimethyl-cyclohexyl ester | 0.52 |
| BIO1703 | (2-Methoxy-phenyl)-carbamic acid 3,3,5-trimethyl-cyclohexyl ester<br>tested as following mixture of isomers:<br>92% (2-Methoxy-phenyl)-carbamic acid (1R*,5R*)-3,3,5-trimethyl-cyclohexyl ester<br>7% (2-Methoxy-phenyl)-carbamic acid (1R*,5S*)-3,3,5-trimethyl-cyclohexyl ester | 1.86 |

Example 3.2

Inhibition of LPL

The results of the inhibition of the PL are used as a preliminary test and are confirmed on LPL. To obtain LPL, 3T3-L1 cells (mouse embryonic fibroblast-like adipocyte cell line) are seeded in a 6-well plate with collagen I-coating in a concentration of $3\times10^5$ cells/well. The cultivation and differentiation of the cells takes place analogously to the details in Example 2 (adipogenesis assay). During the differentiation LPL is increasingly expressed. The LPL is present in a membrane-bound state and is released by one hour incubation with heparin solution at 2-8° C. to the supernatant of the cells.

The LPL thus obtained, in the presence of test substances in different use concentrations, has methylumbelliferyl oleate (MUF oleate) added as the substrate. Fluorescent methylumbelliferyl (MUF) is produced by hydrolysis of the MUF oleate by LPL and is quantified. The inhibition of the hydrolysis of the MUF oleate is a measure of the inhibition of the activity of the LPL and therefore the lipogenesis.

$$\text{Inhibition of the } LPL\ [\%] = 100 - \left(\frac{MUF \text{ test substance} - MUF \text{ control without } LPL}{MUF \text{ control} - MUF \text{ control without } LPL} \times 100\right)$$

wherein

MUF test substance=MUF concentration of the wells with test substance and with LPL MUF control=MUF concentration of the wells without test substance, but with LPL MUF control without LPL=MUF concentration of the wells without test substance and without LPL The $IC_{50}$ is calculated from the inhibition of the LPL [%] in a series of dilutions of tested samples. This is the concentration at which the activity of the LPL and therefore the lipogenesis is 50% inhibited.

TABLE 3.2

| Inhibition of the LPL by the individual substances (mean values of at least 2 independent tests) | | |
|---|---|---|
| | test substance | $IC_{50}$ [mM] |
| BIO1841 | Butyl-carbamic acid 2-isopropyl-cyclohexyl ester tested as following mixture of isomers: 79% Butyl-carbamic acid (1R*,2R*)-2-isopropyl-cyclohexyl ester 20% Butyl-carbamic acid (1R*,2S*)-2-isopropyl-cyclohexyl ester | 1.20 |
| BIO1845 | sec-Butyl-carbamic acid 2,3-dimethyl-cyclohexyl ester | 1.44 |
| BIO1615 | Butyl-carbamic acid 2-isopropenyl-5-methyl-cyclohexyl ester | 0.87 |
| BIO1617 | Butyl-carbamic acid 2,3,6-trimethyl-cyclohexyl ester | 0.61 |
| BIO1844 | sec-Butyl-carbamic acid 3,3,5-trimethyl-cyclohexyl ester tested as following mixture of isomers: 91% sec-Butyl-carbamic acid (1R*,5R*)-3,3,5-trimethyl-cyclohexyl ester 7% sec-Butyl-carbamic acid (1R*,5S*)-3,3,5-trimethyl-cyclohexyl ester | 0.72 |
| BIO1616 | Butyl-carbamic acid 3,3,5-trimethyl-cyclohexyl ester tested as following mixture of isomers: 92% Butyl-carbamic acid (1R*,5R*)-3,3,5-trimethyl-cyclohexyl ester 7% Butyl-carbamic acid (1R*,5S*)-3,3,5-trimethyl-cyclohexyl ester | 1.02 |
| BIO1850 | Hexyl-carbamic acid 3,3,5-trimethyl-cyclohexyl ester tested as following mixture of isomers: 90% Hexyl-carbamic acid (1R*,5R*)-3,3,5-trimethyl-cyclohexyl ester 7% Hexyl-carbamic acid (1R*,5S*)-3,3,5-trimethyl-cyclohexyl ester | 0.68 |

EXAMPLE 4

Lipolysis Assay

Example 4.1

In Vitro Experiments on 3T3-L1 Cells

3T3-L1 cells (mouse embryonic fibroblast-like adipocyte cell line) are seeded in a 48-well plate with collagen I-coating in a concentration of $3\times10^4$ cells/well. The cultivation and differentiation of the cells takes place analogously to the details in Example 2 (adipogenesis assay).

Various concentrations of the test substances are applied to the cells in DMEM, with bovine serum albumen added. After about 20 hours of incubation, the quantification of free glycerol in the supernatant of the cells takes place, which is released by the cells after hydrolysis of triglycerides in the cells and is a measure of the lipolysis of the cells. The quantification of the free glycerol is carried out based on an enzymatic method with a free glycerol reagent.

The stimulation of the lipolysis in the presence of test substances is calculated according to the following equation:

$$\text{Stimulation of the lipolysis [\%]} = \left(\frac{\text{A test substance} - \text{A test substance without cells}}{\text{A control} - \text{A control without cells}} \times 100\right) - 100$$

wherein

A test substance=absorption of the wells with test substance and with cells

A test substance without cells=absorption of the wells with test substance without cells (absorption control)

A control=absorption of the wells without test substance, but with cells

A control without cells=absorption of the wells without test substance and without cells The $EC_{50}$ is calculated from the lipolysis stimulation [%] in a series of dilutions of tested samples. This is the concentration at which the lipolysis is 50% stimulated.

TABLE 4.1

| Stimulation of lipolysis by the individual substances (mean values from at least 2 independent tests). | | |
|---|---|---|
| | test substance | $EC_{50}$ [mM] |
| BIO1741 | Phenyl-carbamic acid cyclohexyl ester | 0.36 |
| BIO1841 | Butyl-carbamic acid 2-isopropyl-cyclohexyl ester tested as following mixture of isomers: 79% Butyl-carbamic acid (1R*,2R*)-2-isopropyl-cyclohexyl ester 20% Butyl-carbamic acid (1R*,2S*)-2-isopropyl-cyclohexyl ester | 0.23 |
| BIO1747 | Cyclohexyl-carbamic acid 4-tert-butyl-cyclohexyl ester | 0.61 |
| BIO1851 | Hexyl-carbamic acid 2-isopropyl-cyclohexyl ester | 1.17 |
| BIO1748 | Benzyl-carbamic acid 2-isopropyl-cyclohexyl ester | 0.81 |

TABLE 4.1-continued

Stimulation of lipolysis by the individual substances (mean values from at least 2 independent tests).

| | test substance | $EC_{50}$ [mM] |
|---|---|---|
| BIO1824 | p-Tolyl-carbamic acid 2-isopropyl-cyclohexyl ester tested as following mixture of isomers: 92% (1S*,2S*)-2-(1-methylethyl)cyclohexyl (4-methylphenyl)carbamate 8% (1S*,2R*)-2-(1-methylethyl)cyclohexyl (4-methylphenyl)carbamate | 0.51 |
| BIO1823 | (4-Ethyl-phenyl)-carbamic acid 3,5-dimethyl-cyclohexyl ester tested as following mixture of isomers: 76.7% (4-Ethyl-phenyl)-carbamic acid (1alpha,3alpha,5alpha)-3,5-dimethyl-cyclohexylester + (4-Ethyl-phenyl)-carbamic acid (1alpha*,3alpha*,5beta*)-3,5-dimethyl-cyclohexylester 23.1% (4-Ethyl-phenyl)-carbamic acid (1alpha,3beta,5beta)-3,5-dimethyl-cyclohexylester | 0.46 |
| BIO1845 | sec-Butyl-carbamic acid 2,3-dimethyl-cyclohexyl ester | 0.19 |
| BIO1743 | Cyclohexyl-carbamic acid 3,5-dimethyl-cyclohexyl ester | 1.89 |
| BIO1842 | Butyl-carbamic acid 2,3-dimethyl-cyclohexyl ester | 0.23 |
| BIO1840 | Butyl-carbamic acid 3,5-dimethyl-cyclohexyl ester | 0.7 |
| BIO1685 | Phenyl-carbamic acid 3,5-dimethyl-cyclohexyl ester tested as following mixture of isomers: 94% Phenyl-carbamic acid (1alpha,3alpha,5alpha)-3,5-dimethyl-cyclohexyl ester + Phenyl-carbamic acid (1alpha*,3alpha*,5beta*)-3,5-dimethyl-cyclohexyl ester 5% Phenyl-carbamic acid (1alpha,3beta,5beta)-3,5-dimethyl-cyclohexyl ester | 0.6 |
| BIO1615 | Butyl-carbamic acid 2-isopropenyl-5-methyl-cyclohexyl ester | 0.82 |
| BIO1617 | Butyl-carbamic acid 2,3,6-trimethyl-cyclohexyl ester | 0.98 |
| BIO1844 | sec-Butyl-carbamic acid 3,3,5-trimethyl-cyclohexyl ester tested as following mixture of isomers: 91% sec-Butyl-carbamic acid (1R*,5R*)-3,3,5-trimethyl-cyclohexyl ester 7% sec-Butyl-carbamic acid (1R*,5S*)-3,3,5-trimethyl-cyclohexyl ester | 0.21 |
| BIO1616 | Butyl-carbamic acid 3,3,5-trimethyl-cyclohexyl ester tested as following mixture of isomers: 92% Butyl-carbamic acid (1R*,5R*)-3,3,5-trimethyl-cyclohexyl ester 7% Butyl-carbamic acid (1R*,5S*)-3,3,5-trimethyl-cyclohexyl ester | 0.45 |
| BIO1573 | Ethyl-carbamic acid 1,7,7-trimethyl-bicyclo[2.2.1]hept-2-yl ester | 0.35 |

Example 4.2

Experiments Using an Ex Vivo Pig Skin Model

Full thickness pig skin patches (pig skin model including subcutis fat layer as described in EP 1 939 279) are excised from the dorsal part of young pig slaughtered for meat. The ex vivo pig skin models have a size of 7×3 mm (diameter×height). They are placed on a titanium grid dipped in culture medium. On top of the skin samples formulations are applied. In parallel to a cosmetic test preparation containing one or more compounds of formula (I) a placebo preparation without any compound of formula (I) is applied as reference (blank).

After 24 hours of incubation, the quantification of free glycerol in the medium surrounding the pig skin models was performed. The glycerol is released by the cells after hydrolysis of triglycerides in the cells of the adipose tissue and is a measure of the lipolysis of the pig skin models. The quantification of the free glycerol is carried out based on an enzymatic method with a free glycerol reagent.

Cosmetic Test Preparation:

| Phase | Ingredient | INCI-Name | % by weight |
|---|---|---|---|
| A | Water | Water (Aqua) | 81.65 |
| | Hydrolite-5 | 1,2 Pentylene Glycol | 2.00 |
| B | PCL liquid 100 | Cetearyl Octanoate | 3.00 |
| | Lanette O | Cetearyl Alcohol | 2.00 |
| | Paraffin oil 5° E | Mineral Oil | 3.00 |
| | Eutanol G | Octyldodecanol | 4.00 |
| | Abil 350 | Dimethicone | 0.50 |
| C | Pemulen TR1 | Acrylates/C10-30 Alkyl Acrylate Crosspolymer | 0.20 |
| | Ultrez-21 | Acrylates/C10-30 Alkyl Acrylate Crosspolymer | 0.05 |
| D | Sodium Hydroxide 10% solution | Sodium Hydroxide | 0.50 |
| E | Compound or a mixture of compounds of formula (I) | | 0.10 |
| | Hydrolite-5 | 1,2 Pentylene Glycol | 3.00 |

Production:

Phases A and B are heated to 70° C. separately. Pemulen TR1 as well as Ultrez-21 are dispersed in phase B when heated to 70° C. Phase B/C is added to phase A by mixing with an Ultra Turrax, followed by emulsifying. Phase D is slowly added to phase A/B/C using a paddle mixer and a pH 5.5-6 is adjusted. The formulation is cooled down while mixing with a paddle mixer. Phase E is prepared by dissolving one or more compounds of formula (I) in Hydrolite-5. Subsequently, phase E is added to the mixture of phase A-D.

The stimulation of the lipolysis in the presence of test substances is calculated according to the following equation:

$$\text{Stimulation of the lipolysis [\%]} = \left(\frac{\text{A test substance}}{\text{A placebo}} \times 100\right) - 100$$

wherein

A test substance=absorption of the wells with medium of ex vivo skin models, on which the formulation containing the test substance was applied A placebo=absorption of the wells with medium of ex vivo skin models, on which the placebo without test substance was applied Table 4.2 shows the individual stimulation results for BIO1617, BIO1823, BIO1841 and BIO1845 when used separately in the cosmetic test preparation specified above.

TABLE 4.2

Stimulation of lipolysis by the individual substances

| | test substance | conc. [%] | stimulation |
|---|---|---|---|
| BIO1841 | Butyl-carbamic acid 2-isopropyl-cyclohexyl ester tested as following mixture of isomers: 79% Butyl-carbamic acid (1R*,2R*)-2-isopropyl-cyclohexyl ester 20% Butyl-carbamic acid (1R*,2S*)-2-isopropyl-cyclohexyl ester | 0.1% | 25% |
| BIO1823 | (4-Ethyl-phenyl)-carbamic acid 3,5-dimethyl-cyclohexyl ester tested as following mixture of isomers: 76.7% (4-Ethyl-phenyl)-carbamic acid (1alpha,3alpha,5alpha)-3,5-dimethyl-cyclohexylester + (4-Ethyl-phenyl)-carbamic acid (1alpha*,3alpha*,5beta*)-3,5-dimethyl-cyclohexylester 23.1% (4-Ethyl-phenyl)-carbamic acid (1alpha,3beta,5beta)-3,5-dimethyl-cyclohexylester | 0.1% | 28% |
| BIO1845 | sec-Butyl-carbamic acid 2,3-dimethyl-cyclohexyl ester | 0.1% | 29% |
| BIO1617 | Butyl-carbamic acid 2,3,6-trimethyl-cyclohexyl ester | 0.1% | 21% |

EXAMPLE 5

SIRT1 Assay

NHDF cells (normal human dermal fibroblasts) were seeded in 96-well plates. After 24 h cultivation at 37° C. and 5% $CO_2$ in DMEM (Dulbecco's Modified Eagle Medium), cells were treated with test substances for another 48 h. After washing the cells with PBS (phosphate buffered saline), the cells were fixed with paraformaldehyde and permeabilized. Then they were washed again and blocked with BSA (bovine serum albumen), followed by incubation with secondary antibody. After extensive washing, the fluorescence is measured in a microplate reader and fluorescence images were recorded on a fluorescence microscope with an attached closed-circuit display camera.

The stimulation of SIRT1 expression was calculated by:

$$\text{Stimulation of } SIRT1 \text{ expression [\%]} = \left(\frac{RFU \text{ test substance} - RFU \text{ background}}{RFU \text{ control} - RFU \text{ background}} \times 100\right) - 100$$

RFU test substance=relative fluorescent units of the wells with test substance, stained completely RFU control=relative fluorescent units of the wells without test substance, stained completely RFU background=relative fluorescent units of the wells without test substance, stained only with secondary antibody.

TABLE 5.1

Stimulation of SIRT1 expression by the individual substances (mean values of at least 2 independent tests

| | test substance | conc. [μM] | Stimulation |
|---|---|---|---|
| BIO1841 | Butyl-carbamic acid 2-isopropyl-cyclohexyl ester tested as following mixture of isomeres: 79% Butyl-carbamic acid (1R*,2R*)-2-isopropyl-cyclohexyl ester 20% Butyl-carbamic acid (1R*,2S*)-2-isopropyl-cyclohexyl ester | 30 | 14% |

TABLE 5.1-continued

| Stimulation of SIRT1 expression by the individual substances (mean values of at least 2 independent tests | | | |
|---|---|---|---|
| | test substance | conc. [μM] | Stimulation |
| BIO1823 | (4-Ethyl-phenyl)-carbamic acid 3,5-dimethyl-cyclohexyl ester<br>tested as following mixture of isomers:<br>76.7% (4-Ethyl-phenyl)-carbamic acid (1alpha,3alpha,5alpha)-3,5-dimethyl-cyclohexylester + (4-Ethyl-phenyl)-carbamic acid (1alpha*,3alpha*,5beta*)-3,5-dimethyl-cyclohexylester<br>23.1% (4-Ethyl-phenyl)-carbamic acid (1alpha,3beta,5beta)-3,5-dimethyl-cyclohexylester | 30 | 66% |
| BIO1845 | sec-Butyl-carbamic acid 2,3-dimethyl-cyclohexyl ester | 30 | 52% |
| BIO1617 | Butyl-carbamic acid 2,3,6-trimethyl-cyclohexyl ester | 30 | 24% |

EXAMPLE 6

ATP Assay

3T3 cells (mouse melanoma fibroblasts) were seeded in 96-well plates. After 24 h cultivation at 37° C. and 5% $CO_2$ in DMEM (Dulbecco's Modified Eagle Medium), cells were treated with test substances for another 48 h. Microscopic observation is performed by 24 h and 48 h after application of test substances to discriminate between cytotoxicity and inhibition of proliferation. ATP content in the cells is measured by The inhibition of proliferation was calculated by:

$$\text{Inhibition of the proliferation } [\%] = 100 - \left(\frac{RLU \text{ test substance} - RLU \text{ control without cells}}{RLU \text{ control} - RLU \text{ control without cells}} \times 100\right)$$

wherein

RLU test substance=relative luminescent units of the wells with test substance and with cells RLU control=relative luminescent units of the wells without test substance, but with cells RLU control without cells=relative luminescent units of the wells without test substance and without cells The $IC_{50}$ is calculated from the proliferation inhibition [%] in a series of non-cytotoxic dilutions of tested samples. This is the concentration at which the proliferation is 50% inhibited.

TABLE 6.1

| Inhibition of proliferation by the individual substances (mean values of at least 2 independent tests) | | |
|---|---|---|
| | test substance | IC50 [μM] |
| BIO1841 | Butyl-carbamic acid 2-isopropyl-cyclohexyl ester<br>tested as following mixture of isomeres:<br>79% Butyl-carbamic acid (1R*,2R*)-2-isopropyl-cyclohexyl ester<br>20% Butyl-carbamic acid (1R*,2S*)-2-isopropyl-cyclohexyl ester | 254.7 |
| BIO1823 | (4-Ethyl-phenyl)-carbamic acid 3,5-dimethyl-cyclohexyl ester<br>tested as following mixture of isomers:<br>76.7% (4-Ethyl-phenyl)-carbamic acid (1alpha,3alpha,5alpha)-3,5-dimethyl-cyclohexylester + (4-Ethyl-phenyl)-carbamic acid (1alpha*,3alpha*,5beta*)-3,5-dimethyl-cyclohexylester<br>23.1% (4-Ethyl-phenyl)-carbamic acid (1alpha,3beta,5beta)-3,5-dimethyl-cyclohexylester | 1389.0 |
| BIO1845 | sec-Butyl-carbamic acid 2,3-dimethyl-cyclohexyl ester | 345.4 |
| BIO1617 | Butyl-carbamic acid 2,3,6-trimethyl-cyclohexyl ester | 243.9 |
| BIO1844 | sec-Butyl-carbamic acid 3,3,5-trimethyl-cyclohexyl ester<br>tested as following mixture of isomeres:<br>91% sec-Butyl-carbamic acid (1R*,5R*)-3,3,5-trimethyl-cyclohexyl ester<br>7% sec-Butyl-carbamic acid (1R*,5S*)-3,3,5-trimethyl-cyclohexyl ester | 478.1 |
| BIO1616 | Butyl-carbamic acid 3,3,5-trimethyl-cyclohexyl ester<br>tested as following mixture of isomeres:<br>92% Butyl-carbamic acid (1R*,5R*)-3,3,5-trimethyl-cyclohexyl ester<br>7% Butyl-carbamic acid (1R*,5S*)-3,3,5-trimethyl-cyclohexyl ester | 219.8 |

EXAMPLE 7

Each of the four substances BIO1617, BIO1823, BIO1841 and BIO1845 were used separately in the following cosmetic preparation. The effectivity of each of the four different preparations according to the invention containing BIO1617, BIO1823, BIO1841 or BIO1845 in a final concentration of 0.5 wt. % was tested by a panel of 30 healthy women (Caucasian type).

Each of the test subjects treated one leg for two months with a preparation according to the invention as given below and treated the other leg with a control preparation free of cyclohexyl carbamates according to formula (I). After two months a test panel of 3 trained examiners assessed the improvement in the cellulite appearance using a scale of 1 (just perceivable improvement) to 5 (complete elimination of the cellulite pattern). On average an improvement of around 2 was achieved.

| | Ingredient | INCI-Name | % by weight |
|---|---|---|---|
| A | Dracorin GOC | Glyceryl Oleate Citrate, Caprylic/Capric Triglyceride | 2.0 |
| | Neutral oil | Caprylic/Capric Triglyceride | 4.0 |
| | Paraffin oil | Paraffinum Liquidum | 4.0 |
| | PCI-Liquid 100 | Cetearyl Ethylhexanoate | 7.0 |
| | Dragoxat 89 | Ethylhexyl Isononanoate | 3.0 |
| | Dow Corning 345 Fluid | Cyclomethicone | 0.5 |
| | Dragosantol 100 | Bisabolol | 0.1 |
| B | Water | Water (Aqua) | 73.3 |
| | Pemulen TR2 | Acrylates/C10-30 Alkyl Acrylate Crosspolymer | 0.2 |
| C | Hydrolite-5 | Pentylene Glycol | 5.0 |
| | BIO1617, BIO1823, BIO1841 or BIO1845 | | 0.5 |
| D | Sodium Hydroxide 10% solution | Sodium Hydroxide | 0.4 |

Production:

Allow Pemulen TR2 to swell in water and predissolve BIO1617, BIO1823, BIO1841 or BIO1845 in Hydrolite-5 (1,2-pentane diol). Mix phase A. Add phase C to phase A then add phase B to phase A/C and emulsify with the Homorex. Continue to stir the O/W emulsion with the paddle mixer and add phase D.

FORMULATION EXAMPLES

Compound of List A

Unless indicated otherwise in the respective formulation example, each compound from the following List A was formulated separately into each single formulation of the Formulation Example 1-10 and F1-F10 given below.

List A:

BIO1617, BIO1851, BIO1823, BIO1581, BIO1841, BIO1745, BIO1844, BIO1748, BIO1845, BIO1616, BIO1743, BIO1747, BIO1842, BIO1840, BIO1615, BIO1573.

Additionally, several formulations were produced including mixtures of two, three of four different compounds selected from list A. In such a case, the amount used in the formulation example refers to the sum of the compounds selected from list A used therein.

In case two different compounds of list A were used as a mixture in the formulation examples given herein, generally the ratio by weight of the two compounds was chosen in the range of from 10:1 to 1:10, preferably in the range of from 5:1 to 1:5, more preferably in the range of from 3:1 to 1:3.

| Formulation Example No. | Product Form |
|---|---|
| 1 | Shower bath |
| 2 | Anti-cellulite body oil |
| 3 | Body spray O/W |

-continued

| Formulation Example No. | Product Form |
|---|---|
| 4 | Cream O/W |
| 5 | Body lotion O/W |
| 6 | Anti-cellulite gel |
| 7 | Body exfoliant |
| 8 | Anti-cellulite balm |
| 9 | Moisture stick |
| 10 | Anti-cellulite spray gel |

In Formulation Examples 1-5, 7, 8 and 10 the following two perfume oils PFO1 and PFO2 were each used as fragrance (DPG=dipropylene glycol).

Perfume Oil PFO1 with Rose Smell

| Component/NAME | Parts by weight |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

Perfume Oil PFO2 with White Blossom and Musk Smell

| Component/NAME | Parts by weight |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |

-continued

| Component/NAME | Parts by weight |
|---|---|
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |

-continued

| Component/NAME | Parts by weight |
|---|---|
| Tetrahydrogeraniol | 13.00 |
| 2,2-Dimethyl-3-cyclohexyl-1-propanol | 80.00 |
| Total: | 1,000.00 |

| | | % by weight | | | | | | | | | |
|---|---|---|---|---|---|---|---|---|---|---|---|
| Ingredient | INCI | 1 | 2 | 3 | 4 | 5 | 6 | 7 | 8 | 9 | 10 |
| Compound of list A | | 0.5 | 0.02 | 0.05 | 0.1 | 0.05 | 0.5 | 0.1 | 0.05 | 0.2 | 0.2 |
| A-C Polyethylen 9 A | Polyethylene | | | | | | | 5 | | | |
| Actipone Black Coffee GW | Water (Aqua), Glycerin, *Coffea Arabica* (Coffee) Seed Extract, *Coffea Robusta* Seed Extract | | | | 1 | | | | | | |
| Actipone *Laminaria Saccharina* | Glycerin, Water (Aqua), *Laminaria Saccharina* Extract | | | | | | | | | 0.5 | |
| Actipone Nutgrass (Motha) Root GW | Water (Aqua), Glycerin, *Cyperus Rotundus* Root Extract | | | | | | 1 | | | | |
| Aristoflex AVC | Ammonium Acryloyldimethyl-taurate/VP Copolymer | | | | | | 0.7 | | | | |
| Avocado Oil | *Persea Gratissima* (Avocado) Oil | | 2 | | 6 | | | | | | |
| Biotive Esculin Sesquihydrate | Esculin | | | | | | | | | | 0.3 |
| (−)-alpha-Bisabolol natural | Bisabolol | | | | | | | | 0.1 | | |
| Butylene Glycol-1,3 | Butylene Glycol | | | | | | | | | 14.34 | 5 |
| Carbopol Ultrez-10 | Carbomer | | | | 0.3 | | | | | | |
| Carbopol Ultrez 21 | Acrylates/ C10-30 Alkyl Acrylate Crosspolymer | | | | | 0.2 | | | | | |
| Carnitine | Carnitine | | | | | | | | 0.8 | | 0.5 |
| Cetiol SB 45 | *Butyrospermum Parkii* (Shea Butter) | | | | 2 | | | | | | |
| Citric Acid 10% solution | Citric Acid | 0.3 | | | | | | 0.05 | 0.2 | | |
| Cocoa Butter, pulverised | *Theobroma Cacao* (Cocoa) Seed Butter | | | | | 0.7 | | | | | |
| Caffeine pure | Caffeine | | | | | | | | | 0.5 | 0.5 |
| Comperlan 100 | Cocamide MEA | 0.5 | | | | | | | | | |
| Covi-Ox T-70 | Tocopherol | | 0.2 | | 0.1 | 0.1 | | | | | |
| Cutina GMS-V | Glyceryl Stearate | | | | 1 | | | | | | |

-continued

| | | % by weight | | | | | | | | | |
|---|---|---|---|---|---|---|---|---|---|---|---|
| Ingredient | INCI | 1 | 2 | 3 | 4 | 5 | 6 | 7 | 8 | 9 | 10 |
| D-Panthenol 75 L | Panthenol | | | | | | | 0.5 | | | |
| Dead Sea Salt | Sea Salt (Maris Sal) | | | | | | | 1.5 | | | |
| Dow Corning 200(100 cs) Silicone Fluid | Dimethicone | | | | | | | | 3 | | |
| Dow Corning 246 Fluid | Cyclohexa-siloxane | | | | | 2 | | | | | |
| Dow Corning 345 Fluid | Cyclo-methicone | | | 0.5 | | | | | | | |
| Dracorin 100 S.E.P. | Glyceryl Stearate, PEG-100 Stearate | | | | | | | 7 | | | |
| Dracorin CE | Glyceryl Stearate Citrate | | | | 3 | | | | | | |
| Dracorin GOC | Glyceryl Oleate Citrate, Caprylic/Capric Triglyceride | | | 2 | | | | | | | |
| Drago-Oat-Active | Water (Aqua), Butylene Glycol, *Avena Sativa* (Oat) Kernel Extract | | | 1 | | | | | | | |
| Dragocid Liquid | Phenoxyethanol, Methylparaben, Ethylparaben, Butylparaben, Propylparaben, Isobutylparaben | | | | 0.8 | 0.8 | | | 0.4 | | 0.8 |
| Dragoderm | Glycerin, *Triticum Vulgare* (Wheat) Gluten, Water (Aqua) | 1 | | | | | | | | | |
| Dragosantol 100 | Bisabolol | | | 0.1 | | 0.1 | 0.5 | | | | |
| Dragosine | Carnosine | | | | | | 0.05 | | | | |
| Dragoxat 89 | Ethylhexyl Isononanoate | | 10 | 3 | | 4 | 5 | | | | |
| Edeta B Powder | Tetrasodium EDTA | | | | | | | 0.1 | | | |
| Edeta BD | Disodium EDTA | 0.1 | | | | | | | | | |
| Emulgin B2 | Ceteareth-20 | | | | | | | 2 | | | |
| Emulsiphos | Potassium Cetyl Phosphate, Hydrogenated Palm Glycerides | | | | | 1.2 | | | | 1 | |
| Essential Oil | Essential Oil | | | | | | 1 | | | | |
| Ethanol 96% | Alcohol Denat. | | | | | | | | | | 10 |
| Extrapone Butcher's broom GWP | Glycerin, Water (Aqua), Pentylene Glycol, *Ruscus Aculeatus* Root Extract | | | | | | | 1 | | | |
| Extrapone *Ginkgo Biloba* | Propylene Glycol, Water (Aqua), *Ginkgo Biloba* Leaf Extract, Glucose, Lactic Acid | | | 1 | | | | | | | |

-continued

| | | % by weight | | | | | | | | | |
|---|---|---|---|---|---|---|---|---|---|---|---|
| Ingredient | INCI | 1 | 2 | 3 | 4 | 5 | 6 | 7 | 8 | 9 | 10 |
| Extrapone Green Tea (Organic) GW | Water (Aqua), Glycerin, *Camellia Sinensis* Leaf Extract | | | | | | | 1 | | | |
| Extrapone Guarana | Water (Aqua), Propylene Glycol, *Paullinia Cupana* Seed Extract, Alcohol | 1 | | | | | | | | | |
| Extrapone Horse Chestnut | Propylene Glycol, Water (Aqua), *Aesculus Hippocastanum* (Horse Chestnut) Seed Extract, Glucose, Lactic Acid | | | | | | | | | | 1 |
| Extrapone Ivy | Propylene Glycol, Water (Aqua), *Hedera Helix* (Ivy) Leaf/Stem Extract, Glucose, Lactic Acid | | | | | | 1 | | | | |
| Extrapone Orange Flower | Water (Aqua), Propylene Glycol, *Citrus Aurantium Amara* (Bitter Orange) Flower Extract | | | | | | 0.5 | | | 0.5 | |
| Extrapone Orange Peel | Water (Aqua), Propylene Glycol, Alcohol, *Citrus Aurantium Dulcis* (Orange) Peel Extract | | | | | | | 1 | | | |
| Extrapone Seaweed | Water (Aqua), Butylene Glycol, *Fucus Vesiculosus* Extract | | | | | | | | 2.5 | | |
| Fragrance PFO1 or PFO2 | Parfum (Fragrance) | 0.5 | 0.5 | 0.2 | 0.3 | 0.3 | | 0.4 | 0.4 | | 0.2 |
| Frescolat MGA | Menthone Glycerin Acetal | 0.5 | | | | | | | | | |
| Frescolat ML | Menthyl Lactate | | | | | | | | | 0.5 | |
| Genapol LRO Liquid | Sodium Laureth Sulfate | 37 | | | | | | | | | |
| Glycerol | Glycerin | | | | 3 | 3 | | | | 4 | |
| Hydrolite 5 | Pentylene Glycol | | | 5 | | | 5 | 5 | | | 3 |

-continued

| | | % by weight | | | | | | | | | |
|---|---|---|---|---|---|---|---|---|---|---|---|
| Ingredient | INCI | 1 | 2 | 3 | 4 | 5 | 6 | 7 | 8 | 9 | 10 |
| Hydroviton | Water (Aqua), Glycerin, Sodium Lactate, Lactic Acid, TEA-Lactate, Serine, Urea, Sorbitol, Sodium Chloride, Allantoin | | | 1 | | | | | | | |
| Isodragol | Triisononanoin | | 13 | | 4 | | | | | | |
| Isopropyl Palmitate | Isopropyl-Palmitate | | | | | | | 3 | | | |
| Jojoba Oil Ethoxilate (Oxypon 328) | Peg-26 Jojoba Acid, Peg-26 Jojoba Alcohol | | | | | | | | 1 | | |
| Karion F | Sorbitol | | | | | | | 1 | | | |
| Keltrol CG-RD | Xanthan Gum | | | | 0.1 | 0.2 | | | | | |
| Lanette 16 | Cetyl Alcohol | | | | 2.5 | | | 3 | | | |
| Lanette O | Cetearyl Alcohol | | | | | 1.5 | | | | | |
| *Macadamia* Nut Oil | *Macadamia Ternifoia* Seed Oil | | 0.5 | | 3 | | | | | | |
| Merquat 550 | Poly-quaternium-7 | 0.5 | | | | | | | | | |
| Mineral Oil | Paraffinum Liquidum | | Ad 100 | 4 | | | | | | | |
| Neo Actipone White Tea | *Camellia Sinensis* Leaf Extract | | | | | 1 | | | | | |
| Neo Heliopan BB | Benzo-phenone-3 | | | | 0.1 | | 0.1 | | | | |
| Neutral Oil | Caprylic/Capric Triglyceride | | | 4 | | | | 10 | | | |
| Orange blossom extract (synephrine-content 0.08%) | *Citrus Aurantium Amara* (Bitter Orange) Flower Extract | 1 | | 1 | | | | | | | |
| Oxynex K Liquid | PEG-8, Tocopherol, Ascorbyl Palmitate, Ascorbic Acid, Citric Acid | | | | | | | 0.1 | | | |
| PCL-Liquid 100 | Cetearyl Ethylhexanoate | | 21 | | 3 | 3 | 3 | | | | |
| PCL-Solid | Stearyl Heptanoate, Stearyl Caprylate | | | | | | 1.5 | | | | |
| Pemulen TR-2 | Acrylates/C10-30 Alkyl Acrylate Crosspolymer | | | 0.2 | | | | | | | |
| Phyto-concentrole Shea Butter | *Glycine Soja* (Soybean) Oil, *Butyrospermum Parkii* (Shea Butter) | | 0.5 | | | | | | | | |
| Potassium sorbate | Potassium Sorbate | | | | 0.2 | | | | | | |
| Propylene Glycol-1,2 | Propylene Glycol | | | | | | | | 2 | | |

-continued

| | | % by weight | | | | | | | | | |
|---|---|---|---|---|---|---|---|---|---|---|---|
| Ingredient | INCI | 1 | 2 | 3 | 4 | 5 | 6 | 7 | 8 | 9 | 10 |
| RonaCare Nicotinamide | Niacinamide | | | | 0.1 | | | | | | |
| Sepigel 305 | Polyacrylamide, C13-14 Isoparaffin, Laureth-7 | | | | | | | | 2 | | |
| Sodium Benzoate | Sodium Benzoate | 0.5 | | | | | | | | | |
| Sodium Chloride | Sodium Chloride | 1 | | | | | | | | | |
| Sodium Hydroxide 10% solution | Sodium Hydroxide | | | 0.4 | 0.45 | 0.6 | 0.01 | | | | 0.4 |
| Sodium Stearate | Sodium Stearate | | | | | | | | | 9 | |
| Solubilizer | PEG-40 Hydrogenated Castor Oil, Trideceth-9, Water (Aqua) | | | | | | | | | | 0.5 |
| Stabileze QM | PVM/Ma Decadiene Crosspolymer | | | | | | | | | | 0.25 |
| SymCalmin | Butylene Glycol, Pentylene Glycol, Hydroxyphenyl Propamidobenzoic Acid | | | | | 1 | | | | | |
| SymDiol 68 | 1.2-Hexanediol, Caprylyl Glycol | | 1 | | | | | | | | |
| SymGlucan | Water (Aqua), Glycerin, Beta-Glucan | | | | | 1 | | | | | |
| SymMatrix | Maltodextrin, *Rubus Fruticosus* (Blackberry) Leaf Extract | | | | | 0.5 | | | | | |
| SymMollient L | Neopentyl Glycol Diisononanoate | | | 7 | | | | | | | |
| SymMollient S | Cetearyl Nonanoate | | | | 1.5 | | | | | | |
| SymMollient W/S | Trideceth-9, PEG-5 Isononanoate, Water (Aqua) | 1 | | | | | | | | | |
| SymPeptide 222 | Glycerin, Water (Aqua), Myristoyl Pentapeptide-8 | | | | | | | | 5 | | |
| SymRelief | Bisabolol, *Zingiber Officinale* (Ginger) Root Extract | | 0.1 | | | | | | | | |
| SymRepair | Hexyldecanol, Bisabolol, Cetylhydroxyproline Palmitamide, Stearic Acid, *Brassica Campestris* (Rapeseed) Sterols | | 1 | | | | | | | | |

-continued

| Ingredient | INCI | % by weight 1 | 2 | 3 | 4 | 5 | 6 | 7 | 8 | 9 | 10 |
|---|---|---|---|---|---|---|---|---|---|---|---|
| SymSitive 1609 | Pentylene Glycol, 4-t-Butylcyclo-hexanol | | | | 1 | | | | | | |
| SymTriol | Caprylyl Glycol, 1,2-Hexanediol, Methylbenzyl Alcohol | 0.5 | | | | | | | | | |
| SymVital | *Aloe Barbadensis* Leaf Juice Powder, Magnesium Ascorbyl Phosphate, *Rubus Idaeus* (Raspberry) Leaf Extract | | | | | | | | 0.5 | | |
| Talcum | Talc | | | | | | | | 3 | | |
| Tego Betain L7 non preserved | Cocamidopropyl Betain | 6 | | | | | | | | | |
| Vitamin A Palmitate | Retinyl Palmitate | | 0.05 | | | | | | | | |
| Vitamin E Acetate | Tocopheryl Acetate | | 0.5 | | | 0.5 | | | | | |
| Water | Water (Aqua) | Ad 100 | | Ad 100 | Ad 100 | Ad 100 | Ad 100 | Ad 100 | Ad 100 | Ad 100 | Ad 100 |

Examples: F1-F10

Orally Consumable Use Examples ["Beauty from Inside"]

Example F1

Fruit Gums

| | % by weight |
|---|---|
| Water | Ad 100 |
| Saccharose | 34.50 |
| Glucose syrup, DE 40 | 31.89 |
| Iso Syrup C* Tru Sweet 01750 (Cerestar GmbH) | 1.50 |
| Gelatin 240 Bloom | 8.20 |
| Yellow and red food colourants | 0.01 |
| Citric acid | 0.20 |
| Compound of list A | 0.075 |

Example F2

Hard Boiled Candy

| | I (% by weight) | II (% by weight) |
|---|---|---|
| Sugar (Saccharose) | Ad 100 | Ad 100 |
| High fructose corn syrup | 41.00 | 41.00 |
| Maltose | 3.00 | 3.00 |
| Palm kernel oil | 0.90 | 0.90 |
| Citric acid | 0.30 | 0.30 |
| Ginger extract | 0.40 | — |
| Ginseng extract | — | 0.40 |

-continued

| | I (% by weight) | II (% by weight) |
|---|---|---|
| Blue colourant | 0.01 | 0.01 |
| Compound of list A | 0.10 | 0.25 |
| Honey | — | 1.50 |
| Honey flavour | — | 0.30 |

Example F3

Gelatin Capsules Suitable for Direct Consumption

| | % by weight I | II | III |
|---|---|---|---|
| Gelatin shell: | | | |
| Glycerin | 2.014 | 2.014 | 2.014 |
| Gelatin 240 Bloom | 7.91 | 7.91 | 7.91 |
| Aspartame | 0.05 | — | — |
| Sucralose | 0.035 | 0.050 | 0.070 |
| Allura Red (red colourant) | 0.006 | 0.006 | 0.006 |
| Brilliant Blue (blue colourant) | 0.005 | 0.005 | 0.005 |
| Core composition: | | | |
| Plant oil triglyceride (coconut oil fraction) | to 100 | to 100 | to 100 |
| Flavour G | 9.95 | 12.0 | 12.0 |
| Compound of list A | 0.07 | 0.20 | 0.50 |

Flavour G had the following composition here (in wt. %): 0.1% neotam powder, 29.3% peppermint oil arvensis, 29.35% peppermint piperta oil Willamette, 2.97% sucralose, 2.28% triacetin, 5.4% diethyl tartrate, 12.1% peppermint oil yakima, 0.7% ethanol, 3.36% 2-hydroxyethylmenthylcarbonate, 3.0% 2-hydroxypropylmenthylcarbonate, 5.77% D-limonene, 5.67% L-menthylacetate.

The gelatin capsules I, II, III suitable for direct consumption were produced according to WO 2004/050069 and in each case had a diameter of 5 mm and the weight ratio of the core material to the shell material was 90:10. The capsules in each case opened in the mouth within less than 10 seconds and dissolved completely within less than 50 seconds.

Example F4

Tablets in Round Tablet Form

| | % by weight | | |
|---|---|---|---|
| | I | II | III |
| Magnesium stearate | 0.9 | 0.9 | 0.9 |
| Citric acid | 0.2 | 0.2 | 0.2 |
| Compound of list A | 0.05 | 0.20 | 0.50 |
| Dextrose | to 100 | to 100 | to 100 |

Example F5

Chewing Gum (with Sugar and Sugar-Free)

| | % by weight | |
|---|---|---|
| | I | II |
| Chewing gum base | 21.0 | 30.0 |
| Glycerin | 0.5 | 1.0 |
| Menthol spearmint eucalyptus flavour P1 | 1.0 | 1.4 |
| Glucose syrup | 16.5 | — |
| Powder sugar | to 100 | — |
| Compound of list A | 0.15 | 0.20 |
| Sorbitol (in powder form) | | to 100 |
| Palatinit | | 9.5 |
| Xylitol | | 2.0 |
| Mannitol | | 3.0 |
| Aspartame | | 0.1 |
| Acesulfame K | | 0.1 |
| Emulgum (emulsifier) | | 0.3 |
| Sorbitol 70%, in water | | 14.0 |

Flavour P1 had the following composition (in wt. %): 0.05% isobutyraldehyde, 0.05% 3-octanol, 0.05% dimethylsulfide, 0.1% trans-2-hexanal, 0.1% cis-3-hexanol, 0.1% natural 4-terpineol, 0.1% isopulegol, 0.2% natural piperiton, 0.3% linalool, 1.0% isoamylalcohol, 1.0% isovaleraldehyde, 2.5% natural alpha-pinene, 2.5% natural beta-pinene, 8.0% eucalyptol, 7.0% I-menthylacetate, 12.0% I-menthone, 5.0% isomenthone, 20.5% I-carvone, 39.45% I-menthol.

the Following Table Relates to Examples F6-F10:

Example F6=Instant drink powder

Example F7=Instant drink powder, sugar-free

Example F8=Carbonated lemonade (soft drink)

Example F9=Soya fruit drink

Example F10=Reduced-fat yoghourt

| | % by weight | | | | |
|---|---|---|---|---|---|
| | F6 | F7 | F8* | F9 | F10 |
| Compound of list A | 0.50 | 0.70 | 0.10 | 0.05 | 0.20 |
| Sugar (Saccharose) | to 100 | | | | |
| Citric acid | 4.00 | 33.33 | 0.2 | | |
| Trisodiumcitrate | 0.26 | | | | |
| Tricalciumphosphate | 0.22 | | | | |
| Ascorbic acid (Vitamin C) | 0.24 | 0.44 | | | |
| Opacifier and Titanium dioxide (E 171) | 0.20 | | | | |
| Xanthan gum (E 415) | 0.072 | | | | |
| Sodiumcarboxymethylcellulose (E 467) | 0.064 | | | | |
| Pectin (E 440) | 0.04 | | | | |
| Spray-dried pineapple flavour, contains yellow colourant tartrazine | 0.40 | | | | |
| Spray-dried raspberry flavour, contains red colorant | | 11.50 | | | |
| Lemon-lime flavour | | | 0.01 | | |
| D-Limonene | | | 0.005 | | |
| Maltodextrin (powder) | | to 100 | | | |
| Aspartame | | 3.30 | | | |
| Saccharose | | | 8.0 | 6.0 | 5.0 |
| Hesperetin (1% by weight in 1,2-propyleneglycol) | | | 0.05 | | |
| Ethylhydroxymethyl furanone | | | 0.01 ppb | | |
| Vanilla flavour | | | | 0.10 | 0.125 |
| Vanillin | | | 15 ppb | | |
| Maltol | | | 350 ppb | | |
| 2,5-dimethyl-4-hydroxy-2H-furan-3-one | | | 3 ppb | | |
| 1,2-Propylene glycol | | | 0.1 | | |
| Mixture of fruit juice concentrates | | | | 45.0 | |
| Soya powder | | | | 5.0 | |
| Yoghurt (1.5% by weight fat) | | | | | to 100 |
| Water | | | to 100 | to 100 | |

*Carbon dioxide is added after filling into bottles.

The invention claimed is:

1. A compound selected from the group consisting of:

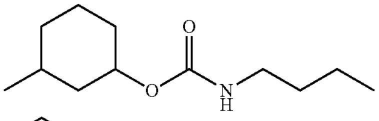

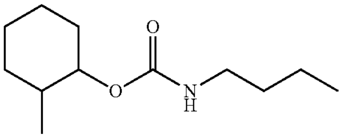

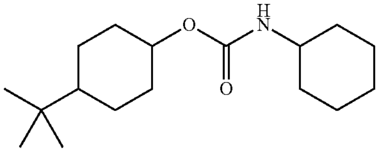

-continued
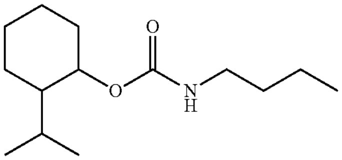
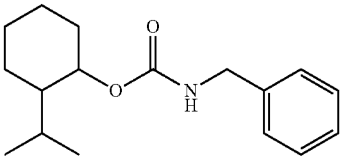
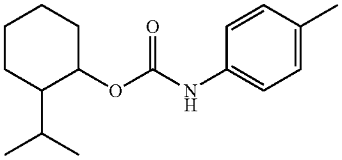
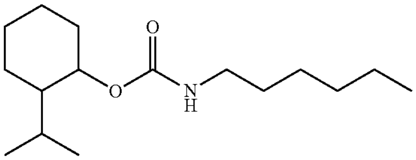
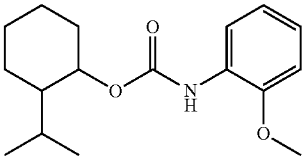
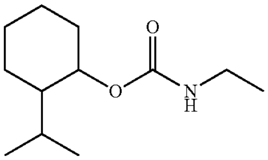
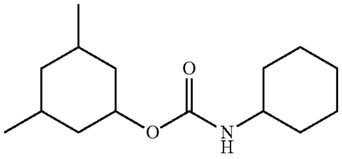
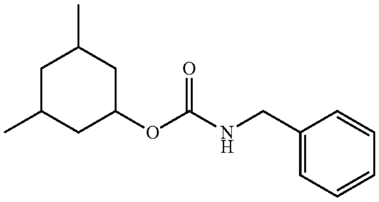
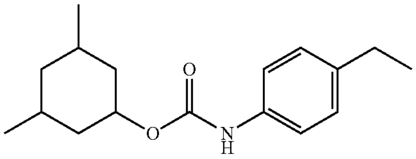
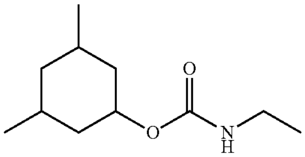
-continued
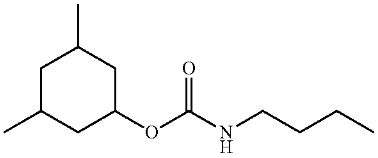
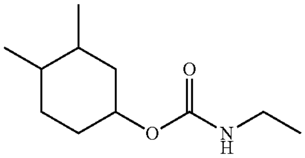
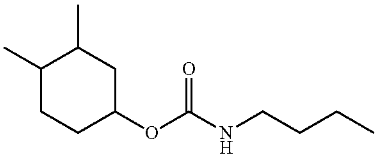
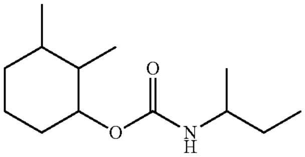
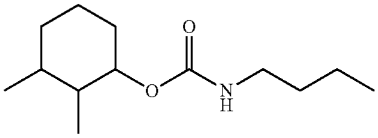
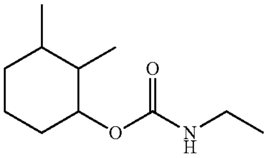
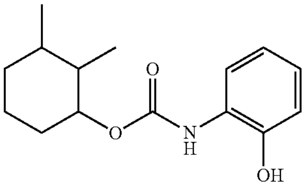
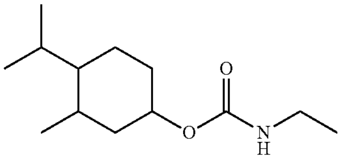
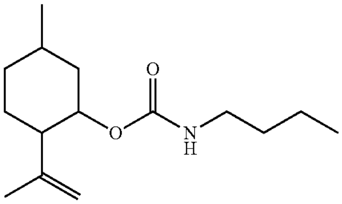
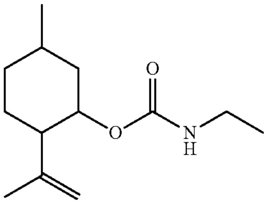

-continued

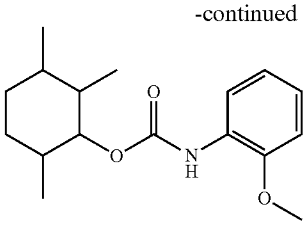

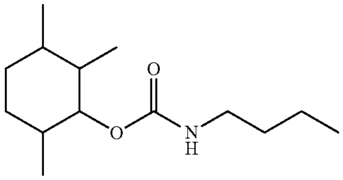

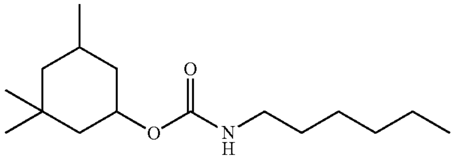

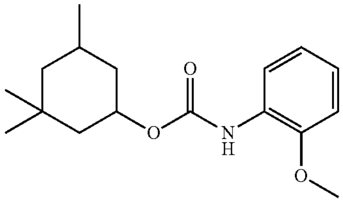

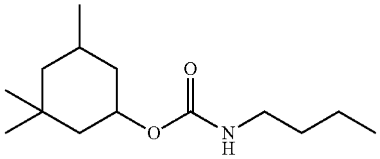

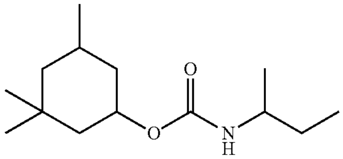

and

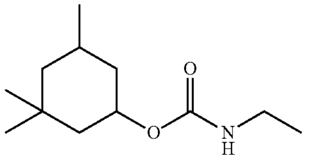

, or a cosmetically or pharmaceutically acceptable salt thereof.

2. A cosmetic or pharmaceutical composition comprising:

(a) one or more compounds of claim 1, or a cosmetically or pharmaceutically acceptable salt thereof.

3. The cosmetic or pharmaceutical composition of claim 2, further comprising:

(b) one or more lipolysis stimulants other than the one or more compounds of (a); and/or (c) one or more stimulators of the transport or oxidation of free fatty acid other than the one or more compounds of (a).

4. The cosmetic or pharmaceutical composition of claim 3 comprising (b), wherein (b) is:

a compound of formula (Xa), or a cosmetically or pharmaceutically acceptable salt thereof, (Xa)

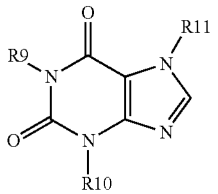

wherein R9, R10 and R11, independently of one another, denote hydrogen or methyl, and/or a compound of formula (PhEA), or a cosmetically or pharmaceutically acceptable salt thereof, (PhEA)

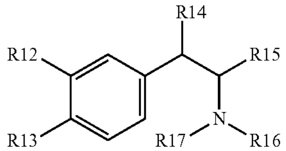

wherein, in each case independently of one another,
R12 and R13 denote hydrogen, hydroxy or methoxy,
R14 denotes hydrogen, hydroxy or methyl,
R15 denotes hydrogen or methyl, and
R16 and R17 denote hydrogen or C1-C4-alkyl.

5. The cosmetic or pharmaceutical composition of claim 3, wherein (b) is caffeine.

6. The cosmetic or pharmaceutical composition of claim 4 comprising one or more compounds of formula (PhEA-i), or a cosmetically or pharmaceutically acceptable salt thereof, (PhEA-i)

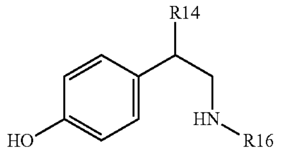

wherein R14 denotes hydrogen, hydroxy or methyl and R16 denotes hydrogen or C1-C4-alkyl.

7. A method for treating or reducing cellulite, comprising administering to an individual an effective amount of a compound of claim 1, or a cosmetically or pharmaceutically acceptable salt thereof.

8. The method of claim 7, wherein the individual is a human.

9. A method for treating or reducing cellulite, comprising administering to an individual an effective amount of cosmetic or pharmaceutical composition of claim 2.

10. The method of claim 9, wherein the individual is a human.

11. A method for reducing lipid quantity contained in subcutaneous fat tissue, comprising administering to an individual an effective amount of a compound of claim 1, or a cosmetically or pharmaceutically acceptable salt thereof.

12. The method of claim 11, wherein the individual is a human.

13. A method for reducing lipid quantity contained in subcutaneous fat tissue, comprising administering to an individual an effective amount of cosmetic or pharmaceutical composition of claim 2.

14. The method of claim 9, wherein the individual is a human.

15. A compound of claim 1 selected from the group consisting of:

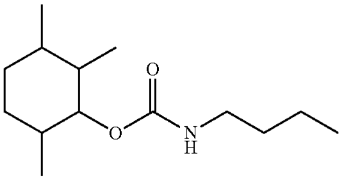
,
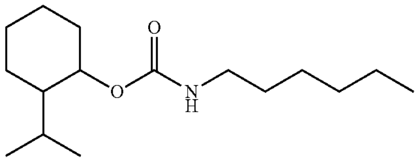
,
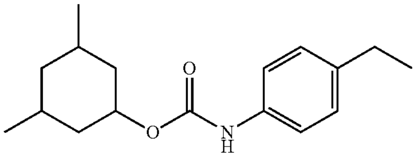
,
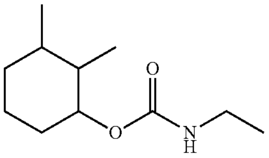
,
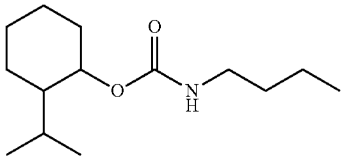
,
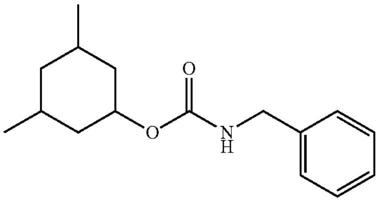
,
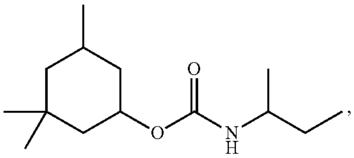
,
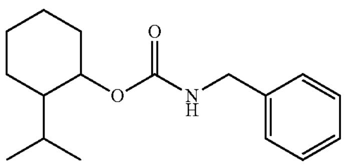
, -continued

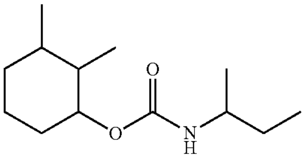
,
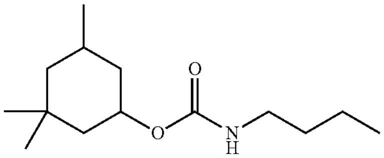
,
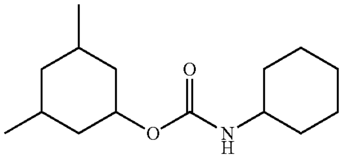
,
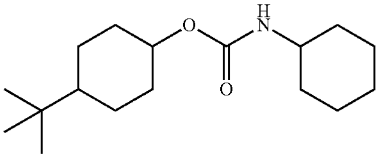
,
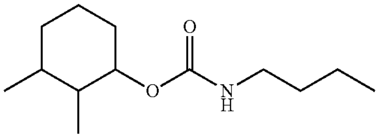
,
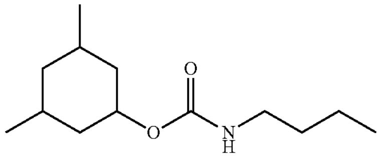
, and
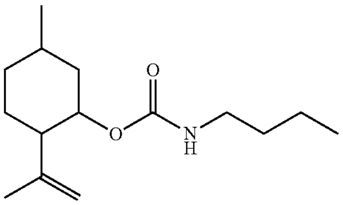
, or a cosmetically or pharmaceutically acceptable salt thereof.

16. A cosmetic or pharmaceutical composition comprising one or more compounds of claim 15, or a cosmetically or pharmaceutically acceptable salt thereof.

17. A method for treating or reducing cellulite, comprising administering to human an effective amount of a cosmetic or pharmaceutical composition of claim 16.

18. A method for reducing lipid quantity contained in subcutaneous fat tissue, comprising administering to an individual an effective amount of cosmetic or pharmaceutical composition of claim 16.

19. A compound having the following formula:

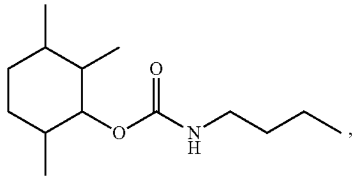 [SMILES: CCCCNC(=O)OC1C(C)CCC(C)C1C]

or a cosmetically or pharmaceutically acceptable salt thereof.

20. A cosmetic or pharmaceutical composition comprising the compound of claim 19, or a cosmetically or pharmaceutically acceptable salt thereof.

21. A method for treating or reducing cellulite, comprising administering to human an effective amount of a cosmetic or pharmaceutical composition of claim 20.

22. A method for reducing lipid quantity contained in subcutaneous fat tissue, comprising administering to an individual an effective amount of cosmetic or pharmaceutical composition of claim 20.

* * * * *